(12) United States Patent
Sieben et al.

(10) Patent No.: US 10,281,397 B2
(45) Date of Patent: May 7, 2019

(54) OPTICAL SENSORS USING SURFACE PLASMON RESONANCE TO DETERMINE AT LEAST ONE PROPERTY RELATING TO PHASE CHANGE OF A HYDROCARBON-BASED ANALYTE

(71) Applicant: SCHLUMBERGER TECHNOLOGY CORPORATION, Sugar Land, TX (US)

(72) Inventors: Vincent Joseph Sieben, Cambridge, MA (US); Kenneth John Chau, Kelowna (CA); Shahnawaz Hossain Molla, Watertown, MA (US); Cailan Libby, Kelowna (CA); Mohammed Al-Shakhs, Kelowna (CA); Farshid Mostowfi, Lexington, MA (US); Simon Ivar Andersen, Tikoeb (DK); Elizabeth Jennings Smythe, Cambridge, MA (US)

(73) Assignee: SCHLUMBERGER TECHNOLOGY CORPORATION, Sugar Land, TX (US)

( * ) Notice: Subject to any disclaimer, the term of this patent is extended or adjusted under 35 U.S.C. 154(b) by 0 days.

(21) Appl. No.: 15/348,721

(22) Filed: Nov. 10, 2016

(65) Prior Publication Data
US 2017/0131204 A1 May 11, 2017

Related U.S. Application Data

(60) Provisional application No. 62/253,251, filed on Nov. 10, 2015, provisional application No. 62/356,750, (Continued)

(51) Int. Cl.
*G01N 21/552* (2014.01)
*G01N 33/28* (2006.01)

(52) U.S. Cl.
CPC .......... *G01N 21/553* (2013.01); *G01N 33/28* (2013.01)

(58) Field of Classification Search
CPC .. G01N 21/553; G01N 21/552; G01N 21/658; G01N 21/65; G01N 33/28; G01J 3/44
(Continued)

(56) References Cited

U.S. PATENT DOCUMENTS

| 4,860,581 A | 8/1989 | Zimmerman et al. |
| 5,804,453 A * | 9/1998 | Chen ................ G01N 21/7703 356/478 |

(Continued)

OTHER PUBLICATIONS

Abudu, a. et al., "Adsorption of Crude Oil on Surfaces Using Quartz Crystal Microbalance with Dissipation (QCM-D) under Flow Conditions," Energy and Fuels, 23(3), 2009, pp. 1237-1248.
(Continued)

*Primary Examiner* — Sang H Nguyen

(57) ABSTRACT

An optical sensor and corresponding method of operation can detect a phase transition and/or related property of a hydrocarbon-based analyte. The optical sensor includes an optical element with a metallic film coupled or integral thereto, with a sample chamber holds the hydrocarbon-based analyte such that the hydrocarbon-based analyte is disposed adjacent the metallic layer. The optical sensor further includes a light source configured to direct light through the optical element such that the light is reflected by the metallic layer under conditions of surface plasmon resonance. The optical sensor analyzes the reflected light to detect a phase transition and/or related property of a hydrocarbon-based analyte.

27 Claims, 28 Drawing Sheets

Related U.S. Application Data filed on Jun. 30, 2016, provisional application No. 62/356,868, filed on Jun. 30, 2016.

(58) Field of Classification Search
IPC .......................................... G01N 21/552,33/28
See application file for complete search history.

(56) References Cited

U.S. PATENT DOCUMENTS

| | | | |
|---|---|---|---|
| 6,058,773 A | 5/2000 | Zimmerman et al. | |
| 6,330,062 B1* | 12/2001 | Corn ...................... | G01N 21/35 356/445 |
| 7,397,559 B1* | 7/2008 | Bratkovski .......... | G01N 21/658 356/301 |
| 7,473,917 B2* | 1/2009 | Singh ................... | G01N 21/553 250/492.1 |
| 8,169,617 B2* | 5/2012 | Ho ....................... | G01N 21/553 356/453 |
| 9,068,962 B2 | 6/2015 | Schneider et al. | |
| 9,249,661 B2 | 2/2016 | Harrison et al. | |
| 9,714,952 B2* | 7/2017 | Feller .................... | G01N 33/84 |
| 2003/0179379 A1* | 9/2003 | Gedig ................... | G01N 21/553 356/445 |
| 2009/0021727 A1* | 1/2009 | Sepulveda Martinez .................... | G01N 21/553 356/128 |
| 2011/0171746 A1* | 7/2011 | Fontaine .............. | G01N 21/553 436/164 |
| 2011/0188043 A1* | 8/2011 | Davidov ............... | G01N 21/553 356/445 |
| 2011/0222066 A1* | 9/2011 | Forcales ............... | G01N 21/552 356/445 |
| 2014/0111809 A1* | 4/2014 | Kang .................... | G01N 21/553 356/445 |
| 2014/0186215 A1 | 7/2014 | Shinta et al. | |
| 2015/0233823 A1* | 8/2015 | Echtermeyer ........ | G01N 21/554 356/445 |
| 2016/0097757 A1 | 4/2016 | Sieben et al. | |
| 2016/0116403 A1 | 4/2016 | Lear et al. | |

OTHER PUBLICATIONS

Adyani, W. N. et al., "A Systematic Approach to Evaluate Asphaltene Precipitation during CO2 Injection", SPE 143903, presented at the SPE Enhanced Oil Recovery Conference, Kuala Lumpur, Malaysia, 2011, 27 pages.
Akbarzadeh, K. et al., "Introduction to a Novel Approach for Modeling Wax Deposition in Fluid Flows. 1. Taylor-Couette System", Industrial and Engineering Chemistry Research, 2008, 47(3), pp. 953-963.
Akbarzadeh, K. et al., "The Importance of Wax-Deposition Measurements in the Simulation and Design of Subsea Pipelines", SPE 115131, SPE Projects, Facilities and Construction, 2010, 5(2), pp. 49-57.
Bai, C. et al., "Thermal, Macroscopic, and Microscopic Characteristics of Wax Deposits in Field Pipelines", Energy & Fuels, 2013, 27(2), pp. 752-759.
Buckley, J.S., "Predicting the Onset of Asphaltene Precipitation from Refractive Index Measurements", Energy & Fuels, 1999, 13(2), pp. 328-332.
Buckley, J.S . et al., "Asphaltene Precipitation and Solvent Properties of Crude Oils", Petroleum Science and Technology, 1998, 16(3-4), pp. 251-285.
Gonzalez, D. L. et al., "Effects of Gas Additions to Deepwater Gulf of Mexico Reservoir Oil: Experimental Investigation of Asphaltene Precipitation and Deposition", SPE 159098, presented at the SPE Annual Technical Conference and Exhibition, San Antonio, Texas, USA, Society of Petroleum Engineers, 2012, 11 pages.
Hammami, A. et al., "Asphaltene Precipitation from Live Oils: An Experimental Investigation of Onset Conditions and Reversibility", Energy & Fuels, 1999, 14(1), p. 14-18.
Huang, Z. et al., "The Effect of Operating Temperatures on Wax Deposition", Energy & Fuels, 2011, 25(11), pp. 5180-5188.
Jamaluddin, A.K.M. et al., "A Comparison of Various Laboratory Techniques to Measure Thermodynamic Asphaltene Instability", SPE-72154, presented at the SPE Asia Pacific Improved Oil Recovery Conference, Kauala Lumpur, Malaysia, Society of Petroleum Engineers, 2001, pp. 17 pp.
Jamaluddin, A.K.M. et al., "An Investigation of Asphaltene Instability Under Nitrogen Injection", SPE 74393, presented at the SPE International Petroleum Conference and Exhibition, Villahermosa, Mexico, Society of Petroleum Engineers Inc., 2012, pp. 10 pp.
Jorgenson, R. C. et al., "A fiber-optic chemical sensor based on surface plasmon resonance", Sensors and Actuators: B. Chemical, 1993, 12(3), pp. 213-220.
Joshi, N. B., et al., "Asphaltene Precipitation from Live Crude Oil", Energy & Fuels, 2001, 15(4), pp. 979-986.
Kalantari-Dahaghi, A. et al., "Formation Damage Through Asphaltene Precipitation Resulting From C02 Gas Injection in Iranian Carbonate Reservoirs" SPE Production & Operations, 2008, 23(2), pp. 210-214.
Mehfuz, R., "Improving the Excitation Efficiency of Surface Plasmon Polaritons Near Small Apertures in Metallic Films", 2013, The University of British Columbia: Okanagan, 140 pages.
Milhet, M. et al., "Liquid-solid equilibria under high pressure of tetradecane + pentadecane and tetradecane + hexadecane binary systems", Fluid Phase Equilibria, 2005, 235(2), pp. 173-181.
Ooms, M. D. et al., "Surface Plasmon Resonance for Crude Oil Characterization", Energy & Fuels, 2015, 29(5), pp. 3019-3023.
Reimhult, E. et al., "Simultaneous Surface Plasmon Resonance and Quartz Crystal Microbalance with Dissipation Monitoring Measurements of Biomolecular Adsorption Events Involving Structural Transformations and Variations in Coupled Water", Analytical Chemistry, 2004, 76(24), pp. 7211-7220.
Sarica, C. et al., "Review of Paraffin Deposition Research under Multiphase Flow Conditions", Energy & Fuels, 2012, 26(7), pp. 3968-3978.
Schneider, M. H. et al., "Measurement of Asphaltenes Using Optical Spectroscopy on a Microfluidic Platform", Analytical Chemistry, 2013, 85(10), pp. 5153-5160.
Skinner, N. G. et al. "Downhole fiber optic sensing: the oilfield service provider's perspective: from the cradle to the grave", Proc. SPIE 9098, Fiber Optic Sensors and Applications, 2014, 18 pages.
Takagi, T. et al., "Refractive Index of Liquids under High Pressure", Journal of Chemical & Engineering Data, 1982, 27(1), pp. 16-18.
Tvakkoli, M. et al., "Asphaltene Deposition in Different Depositing Environments: Part 2. Real Oil," Energy & Fuels, 2014, 28(6), pp. 3594-3603.
Tvakkoli, M. et al., "Asphaltene Deposition in Different Depositing Environments: Part 1. Model Oil", Energy & Fuels, 2014, 28(3), pp. 1617-1628;.
Wang, J. et al., "Asphaltene Deposition on Metallic Surfaces," Journal of Dispersion Science and Technology, 2004, 25(3), pp. 287-298.
Jorgenson, R. C. et al., "Control of the dynamic range and sensitivity of a surface plasmon resonance based fiber optic sensor", Sensors and Actuators: A. Physical, 1994, 43(1-3), pp. 44-48.
"Standard Test Method for Determinatoin of Asphaltenes (Heptane Insolubles) in Crude Petroleum and Petroleum Products", ASTM D6560, 2005, 6 pages.

* cited by examiner

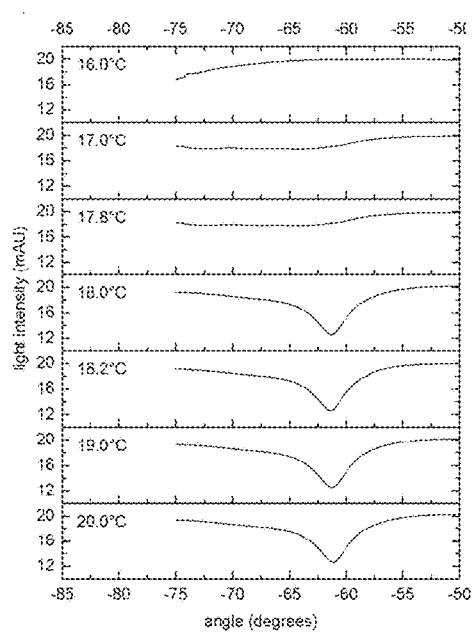
FIG. 9A
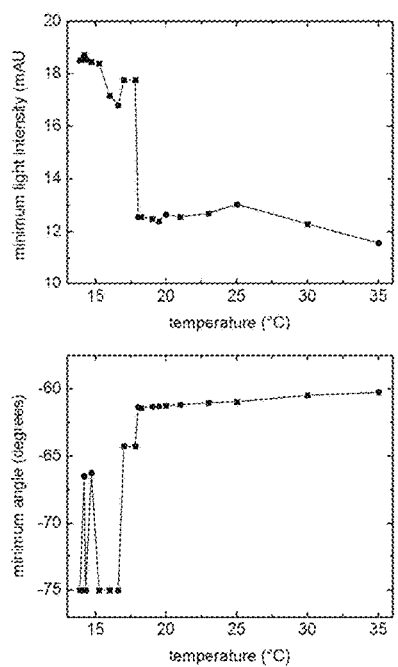
FIG. 9B
FIG. 9C

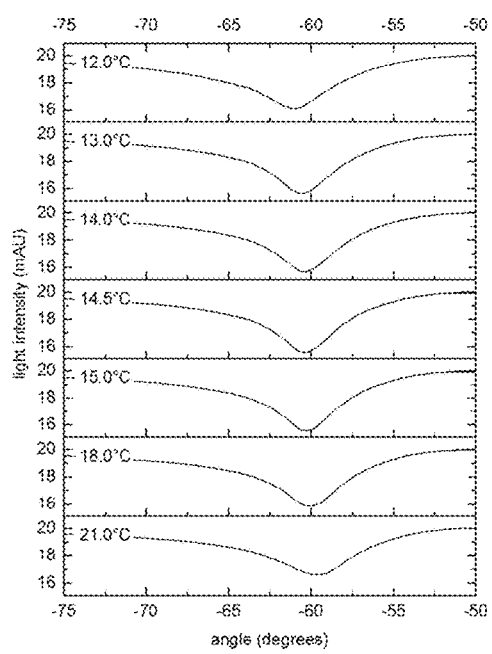
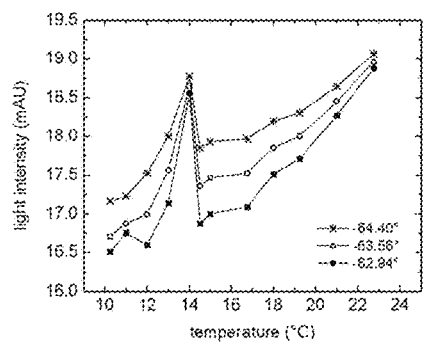
FIG. 10B
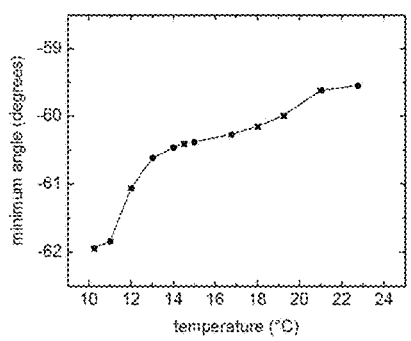
FIG. 10C
FIG. 10A

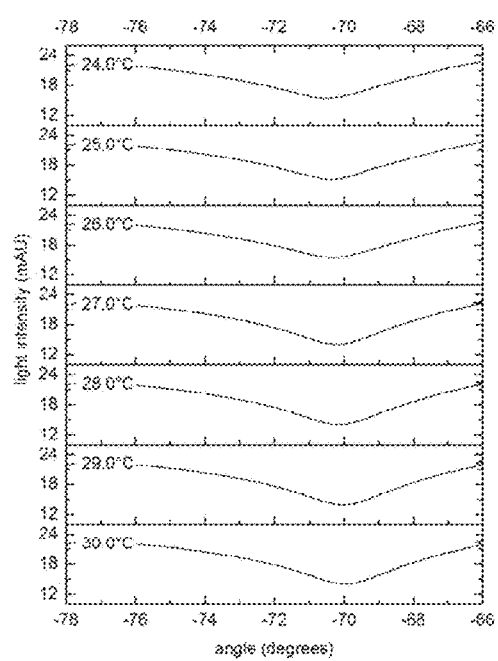
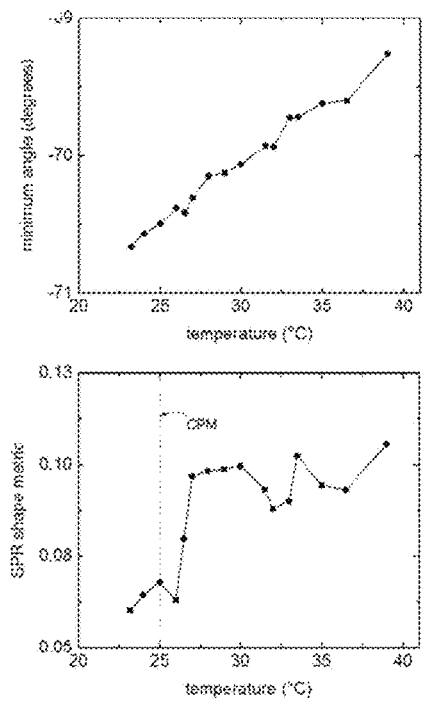
FIG. 12B
FIG. 12C
FIG. 12A

US 10,281,397 B2

OPTICAL SENSORS USING SURFACE PLASMON RESONANCE TO DETERMINE AT LEAST ONE PROPERTY RELATING TO PHASE CHANGE OF A HYDROCARBON-BASED ANALYTE

CROSS-REFERENCE TO RELATED APPLICATIONS

This application claims the benefit of the following applications, each of which is incorporated herein by reference in its entirety: U.S. Provisional Patent Application Ser. No. 62/253,251, filed Nov. 10, 2015; U.S. Provisional Patent Application Ser. No. 62/356,750, filed Jun. 30, 2016; and U.S. Provisional Patent Application Ser. No. 62/356,868, filed Jun. 30, 2016.

TECHNICAL FIELD

This disclosure relates to measurements of properties relating to phase change of hydrocarbon-based analytes induced by changes in temperature, pressure and/or composition of the hydrocarbon-based analyte.

BACKGROUND

Optical measurements on crude oils for composition analysis had been previously demonstrated by Buckley et al., "Asphaltene Precipitation and Solvent Properties of Crude Oils," Petroleum Science and Technology, 1998, Vol. 16(3-4), pgs. 251-285. Until recently, very little had been explored with regard to the use of Surface Plasmon Resonance (SPR) measurements for testing reservoir fluids (oil and natural gas). Ooms et al., "Surface Plasmon Resonance for Crude Oil Characterization," Energy & Fuels, 2015, Vol. 29(5), pgs. 3019-3023 describes Surface Plasmon Resonance in connection with oils.

SUMMARY

This summary is provided to introduce a selection of concepts that are further described below in the detailed description. This summary is not intended to identify key or essential features of the claimed subject matter, nor is it intended to be used as an aid in limiting the scope of the claimed subject matter.

In accordance with some examples, an optical sensor is provided that includes a sample chamber that is configured to hold a hydrocarbon-based analyte. The sensor can also include at least one temperature control element controlling temperature of the hydrocarbon-based analyte in the sample chamber, and at least one pressure control element for controlling pressure of the of the hydrocarbon-based analyte in the sample chamber. A thin metallic film is disposed adjacent the sample chamber. A light source and optical element cooperate to direct light produced by the light source to the metallic film under conditions of surface plasmon resonance and to direct light reflected at the interface of the metallic film for output from the optical element. The light reflected at the interface of the metallic film is sensitive to surface plasmon resonance at the interface of the metallic film. An optoelectronic device (e.g., photodetector or spectrometer) is configured to (a) receive light reflected at the interface of the metallic film as directed by the optical element and (b) generate a corresponding electrical signal. A computer processing system generates and stores data based on the electrical signal generated by the optoelectronic device for a number of test measurements at variable conditions of the hydrocarbon-based analyte in the sample chamber as controlled by the at least one temperature control element and the at least one pressure control element. The computer processing system can process the data to determine at least one property related to phase transition of the hydrocarbon-based analyte.

In some embodiments, the at least one property related to phase transition of the hydrocarbon-based analyte can be induced by at least one of: change in temperature of the hydrocarbon-based analyte, change in pressure of the hydrocarbon-based analyte, and change in composition of the hydrocarbon-based analyte.

In some embodiments, the at least one property related to phase transition of the hydrocarbon-based analyte can specify temperature and/or pressure conditions for a phase transition of the hydrocarbon-based analyte.

In some embodiments, the number of test measurements can be performed at variable temperature conditions of the hydrocarbon-based analyte in the sample chamber. In embodiments, the number of test measurements can be performed at variable pressure conditions of the hydrocarbon-based analyte in the sample chamber. In some embodiments, the number of test measurements can be performed at variable temperature and pressure conditions of the hydrocarbon-based analyte in the sample chamber.

In some embodiments, the at least one thermal control element includes at least one of a heat exchanger, a thermoelectric Peltier device, and a heat sink. A thermal controller can be operably coupled to at least one heat exchanger of the optical sensor.

In some embodiments, the optical element can be a prism that directs light produced by the light source to the metallic film and that directs light reflected at the interface of the metallic film for output from the prism.

In some embodiments, the computer processing system of the optical sensor can generate and store data based on the electrical signal generated by the optoelectronic device for test measurements of the hydrocarbon-based analyte loaded into the sample chamber (or flowing-thru the sample chamber). The computer processing system can process the data to detect a phase transition with respect to the hydrocarbon-based analyte and/or determine at least one property relating to a phase transition of the hydrocarbon-based analyte.

In some embodiments, the light source can be a monochromatic light source that produces monochromatic light. The sample chamber, the prism and the at least one thermal control element can be part of a thermally-controlled assembly that is configured for controlled rotational movement of the thermally-controlled assembly relative to the monochromatic light source in order to vary angle of incidence of monochromatic light on the interface of the metallic film. The optoelectronic device can be a photodetector that is configured for controlled linear movement along a trajectory that maintains alignment of the photodetector with center of a reflected light beam that is output from the prism during controlled rotational movement of the thermally-controlled assembly relative to the monochromatic light source. A mechanical chopper can be disposed in an optical path between the monochromatic light source and the prism, wherein the mechanical chopper is configured to modulate the monochromatic light produced by the monochromatic light source at a predetermined frequency for supply to the prism. A lock-in amplifier that processes an electrical signal output of the photodetector, wherein operation of the lock-in amplifier is coordinated with the predetermined frequency of light modulation performed by the mechanical chopper.

The computer processing system can be configured to generate and store intensity data based on the electrical signal generated by the photodetector as a function of angular position of the thermally-controlled assembly relative to the monochromatic light source during controlled rotational movement of the thermally-controlled assembly relative to the monochromatic light source for the number of test measurements at variable conditions of the hydrocarbon-based analyte in the sample chamber as controlled by the at least one temperature control element and the at least one pressure control element. The intensity data characterizes intensity of light reflected at the interface of the metallic film during controlled rotational movement of the thermally-controlled assembly relative to the monochromatic light source. The computer processing system can process the intensity data as a function of angular position of the thermally-controlled assembly relative to the monochromatic light source to determine the at least one property related to phase transition of the hydrocarbon-based analyte.

In some embodiments, the intensity data corresponding to different angular positions of the thermally-controlled assembly relative to the monochromatic light source can be evaluated to determine the at least one property related to phase transition of the hydrocarbon-based analyte. For example, the at least one property related to phase transition of the hydrocarbon-based analyte can be determined based on at least one of the following: i) a temperature condition and/or pressure condition corresponding to a local minima or dip in the intensity data as a function of the angular position of the thermally-controlled assembly relative to the monochromatic light source; ii) a temperature condition and/or pressure condition corresponding to an abrupt change to slope or shape of a local minima or dip in the intensity data as a function of the angular position of the thermally-controlled assembly relative to the monochromatic light source; iii) a temperature condition and/or pressure condition corresponding to an abrupt change in the minimum of the intensity data over the angular positions of the thermally-controlled assembly as a function of temperature or pressure; iv) a temperature condition and/or pressure condition corresponding to an abrupt change in the intensity data at a plurality of angular positions of the thermally-controlled assembly as a function of temperature or pressure; v) a temperature condition and/or pressure condition corresponding to an abrupt change in the angle of minimum intensity data over the angular positions of the thermally-controlled assembly relative to the monochromatic light as a function of temperature or pressure; and vi) a temperature condition and/or pressure condition corresponding to other signal metrics derived from the intensity data as a function of the angular position of the thermally-controlled assembly relative to the monochromatic light source as a function of temperature or pressure.

In some embodiments, the computer processing system of the optical sensor can generate and store intensity data based on the electrical signal generated by the photodetector for test measurements involving controlled rotational movement of the thermally-controlled assembly relative to the monochromatic light source with the hydrocarbon-based analyte loaded into the sample chamber (or flowing-thru the sample chamber). The computer processing system can process the intensity data as a function of angular positions of the thermally-controlled assembly relative to the monochromatic light to detect a phase transition with respect to the hydrocarbon-based analyte and/or determine at least one property relating to a phase transition of the hydrocarbon-based analyte. For example, the intensity data corresponding to different angular positions of the thermally-controlled assembly relative to the monochromatic light source can be evaluated to detect a phase change or phase transition property with respect to the hydrocarbon-based analyte based on abrupt changes or other signal metrics measured from intensity data.

In some embodiments, the light source can be a polychromatic light source that produces polychromatic light. The sample chamber, the prism and the at least one thermal control element can be part of a thermally-controlled assembly. The optoelectronic device can be a spectrometer that is configured to receive polychromatic light reflected from the metallic film.

The computer processing system can be configured to generate and store spectral data representing intensity as a function of wavelength based on the electrical signals generated by the spectrometer for the number of test measurements at variable conditions of the hydrocarbon-based analyte in the sample chamber as controlled by the at least one temperature control element and the at least one pressure control element. The computer processing system can process the spectral data as a function of wavelength to determine the at least one property related to phase transition of the hydrocarbon-based analyte.

In some embodiments, the spectral data can be evaluated to determine the at least one property related to phase transition of the hydrocarbon-based analyte. For example, the at least one property related to phase transition of the hydrocarbon-based analyte can be determined based on temperature and/or pressure conditions that produce a shift in a local minima or dip in the spectral data or based on other signal metrics derived from the spectral data.

In some embodiments, the computer processing system of the optical sensor can generate and store spectral data based on the output of the spectrometer for test measurements with the hydrocarbon-based analyte loaded into the sample chamber (or flowing-thru the sample chamber). The computer processing system can process the spectral data to detect a phase transition with respect to the hydrocarbon-based analyte and/or determine at least one property relating to a phase transition of the hydrocarbon-based analyte. For example, the spectral data can be evaluated to detect a phase change or phase transition property with respect to the hydrocarbon-based analyte based on local minima shift or other signal metric measured from spectral data.

In some embodiments, the sample chamber can have a fixed volume.

In some embodiments, the sample chamber can be part of a flow-thru cell.

In some embodiments, the metallic film can be formed as a coating or part of a multi-layer film structure on the optical element. In some embodiments, the metallic film can be formed as a coating or part of a multi-layer film structure on a substrate that is disposed adjacent the optical element.

In some embodiments, a layer of protective material covers the metallic film such that the hydrocarbon-based analyte does not directly contact the metallic film.

In some embodiments, the optical sensor can employ an electrical circuit that is electrically coupled to the metallic film for controlled resistive heating of the metallic film. The electric circuit can be configured for pulsed-mode operation including on cycles where the metallic film is heating by resistive heating and off cycles where the metallic film is not heated by resistive heating.

In some embodiments, the at least one property related to phase transition of the hydrocarbon-based analyte can be derived from test measurements with i) pressure or pressure differential of the hydrocarbon-based analyte in the sample chamber at a controlled pressure and ii) temperature of the hydrocarbon-based analyte in the sample chamber controlled over a range of set point temperatures.

In some embodiments, the at least one property related to phase transition of the hydrocarbon-based analyte can be derived from test measurements with i) temperature of the hydrocarbon-based analyte in the sample chamber at a set temperature and ii) pressure or pressure differential of the hydrocarbon-based analyte in the sample chamber controlled over a range of set point pressures.

In some embodiments, the at least one property related to phase transition of the hydrocarbon-based analyte can be derived from test measurements with pressure or pressure differential and temperature of the hydrocarbon-based analyte in the sample chamber controlled over a range of corresponding set point pressures and set point temperatures.

In some embodiments, the at least one property related to phase transition of the hydrocarbon-based analyte can be a temperature condition and/or pressure condition where components that are dissolved in the hydrocarbon-based analyte precipitate and form solids.

In some embodiments, the at least one property related to phase transition of the hydrocarbon-based analyte can be a Wax Appearance Temperature (WAT) where wax components that are dissolved in the hydrocarbon-based analyte first precipitate and form solid material.

In some embodiments, the at least one property related to phase transition of the hydrocarbon-based analyte can be a temperature condition and/or pressure condition where components of the hydrocarbon-based analyte transition from a gas phase to a liquid phase.

In some embodiments, the at least one property related to phase transition of the hydrocarbon-based analyte can be a temperature condition and/or pressure condition where components of the hydrocarbon-based analyte transition from a liquid phase to a gas phase.

In some embodiments, the at least one property related to phase transition of the hydrocarbon-based analyte can be a temperature condition and/or pressure condition vapor forms from the hydrocarbon-based analyte or where vapor dissolve into the hydrocarbon-based analyte as induced by changes in temperature, pressure and/or composition of the hydrocarbon-based analyte.

In some embodiments, the at least one property related to phase transition of the hydrocarbon-based analyte can be a temperature condition and/or pressure condition where hydrates form from the hydrocarbon-based analyte as induced by changes in temperature, pressure and/or composition of the hydrocarbon-based analyte.

In some embodiments, the at least one property related to phase transition of the hydrocarbon-based analyte can be a temperature condition and/or pressure condition where scale or other inorganic material precipitate from the hydrocarbon-based analyte as induced by changes in temperature, pressure and/or composition of the hydrocarbon-based analyte.

In some embodiments, the at least one property related to phase transition of the hydrocarbon-based analyte can be a temperature condition and/or pressure condition where asphaltenes in the hydrocarbon-based analyte deposit as a solid film as induced by changes in temperature, pressure and/or composition of the hydrocarbon-based analyte.

In some embodiments, the optical sensor can be part of a downhole tool that is conveyed in a wellbore that traverses a subterranean formation and configured to sample formation fluid obtained from the subterranean formation. In this configuration, the optical sensor of the downhole tool can be used to determine at least one property related to phase transition of the formation fluid.

In some embodiments, the optical sensor can be part of a wellsite that produces fluid obtained from a subterranean formation. In this configuration, the optical sensor of the wellsite can be used to determine at least one property related to phase transition of the produced fluid.

In some embodiments, the optical sensor includes a sample chamber that is configured to hold a hydrocarbon-based analyte. A metallic film is disposed adjacent the sample chamber. A light source and optical element (such as a prism or optical fiber) cooperate to direct light produced by the light source to the metallic film under conditions of surface plasmon resonance and to direct light reflected at the interface of the metallic film for output from the optical element. The light reflected at the interface of the metallic film is sensitive to surface plasmon resonance at the interface of the metallic film. A spectrometer can be configured to (a) receive light reflected at the interface of the metallic film as directed by the optical element and (b) generate a corresponding spectral data. A computer processing system can be configured to acquire and store the spectral data generated by the spectrometer. The computer processing system can process the spectral data to detect a phase transition of the hydrocarbon-based analyte. For example, the computer processing system can detect a phase transition of the hydrocarbon-based analyte based on a shift in a local minima or dip in the spectral data.

In another aspect, a method of optical sensing includes loading a sample chamber with a hydrocarbon-based analyte and a metallic film disposed adjacent the sample chamber. With the hydrocarbon-based analyte in the sample chamber, light produced by a light source is directed to the metallic film under conditions of surface plasmon resonance, and light reflected at the interface of the metallic film is directed to an optoelectronic device. The optoelectronic device can be configured to (a) receive the light reflected at the interface of the metallic film and (b) generate a corresponding electrical signal, wherein the light reflected at the interface of the metallic film is sensitive to surface plasmon resonance at the interface of the metallic film. A computer processing system generates and store data based on the electrical signal generated by the optoelectronic device. The computer processing system also processes the data to detect a phase transition with respect to the hydrocarbon-based analyte and/or determine at least one property related to phase transition of the hydrocarbon-based analyte.

In some embodiments, the computer processing system can be configured to generate and store data based on the electrical signal generated by the optoelectronic device for a number of test measurements at variable conditions of the hydrocarbon-based analyte in the sample chamber as controlled by at least one temperature control element and at least one pressure control element.

In some embodiments, the optoelectronic device can include a photodetector, and the computer processing system generates and stores intensity data derived from the output of the photodetector. The computer processing system can be configured to process the intensity data to detect a phase transition or related property with respect to the hydrocarbon-based analyte.

In some embodiments, the optoelectronic device can include a spectrometer, and the computer processing system acquires and stores spectral data generated by the spectrometer. The computer processing system can be configured to process the spectral data to detect a phase transition with respect to the hydrocarbon-based analyte and/or derive at least property of a phase transition of the hydrocarbon-based analyte.

BRIEF DESCRIPTION OF THE DRAWINGS

Those skilled in the art should more fully appreciate advantages of various embodiments of the present disclosure from the following "Description of Illustrative Embodiments," discussed with reference to the drawings summarized immediately below.

FIG. 8A includes plots of the nominal intensity data as function of angular position of the thermally-controlled block (prism) at various temperatures for a tetradecane (or C14) sample. FIG. 8B is a plot of the minimum nominal intensity data over the angular positions of the thermally-controlled block (prism) as a function of set point temperature. FIG. 8C is a plot of angular block position of minimum intensity over the angular positions of the thermally-controlled block (prism) as a function of set point temperature.

FIGS. 9A-9C are plots of data derived from the workflow of FIG. 7 in order to determine the WAT of hexadecane or C16. FIG. 9A includes plots of the nominal intensity data as function of angular position of the thermally-controlled block (prism) at various temperatures for a hexadecane (or C16) sample. FIG. 9B is a plot of the minimum nominal intensity data over the angular positions of the thermally-controlled block (prism) as a function of set point temperature. FIG. 9C is a plot of angular block position of minimum intensity over the angular positions of the thermally-controlled block (prism) as a function of set point temperature.

FIGS. 10A-10C are plots of data derived from the workflow of FIG. 7 in order to determine the WAT of a mixture of tetradecane (C14) and hexadecane (C16). The mixture has 0.8 molar fraction C16 and 0.2 molar fraction C14. FIG. 10A includes plots of the nominal intensity data as function of angular position of the thermally-controlled block (prism) at various temperatures for the mixture. FIG. 10B includes plots of the nominal intensity data for three particular angular positions (−64.4°, −63.56°, −62.94°) of the thermally-controlled block (prism) as a function of set point temperature. FIG. 10C is a plot of angular block position of minimum intensity over the angular positions of the thermally-controlled block (prism) as a function of set point temperature.

FIGS. 12A-12C are plots of data derived from the workflow of FIG. 7 in order to determine the WAT of a crude oil sample (referred to as "crude oil 1 sample"). FIG. 12A includes plots of the nominal intensity data as function of angular position of the thermally-controlled block (prism) at various temperatures for the mixture. FIG. 12B includes plots of the nominal intensity data over three particular angular positions (−72.95°, −71.75°, −70.87°) of the thermally-controlled block (prism) as a function of set point temperature. FIG. 12C is a plot of angular block position of minimum intensity over the angular positions of the thermally-controlled block (prism) as a function of set point temperature.

FIG. 14A is a plot of the nominal intensity data as function of angular position of the thermally-controlled block (prism) at various temperatures for the crude oil 2 sample. FIG. 14B includes plots of the nominal intensity data over three particular angular positions (−64.10°, −63.11°, −62.11°) of the thermally-controlled block (prism) as a function of set point temperature. FIG. 14C is a plot of angular block position of minimum intensity over the angular positions of the thermally-controlled block (prism) as a function of set point temperature.

FIG. 16A is a plot of the nominal intensity data as function of angular position of the thermally-controlled block (prism) at various temperatures for the crude oil 3 sample. FIG. 16B includes plots of the nominal intensity data over three particular angular positions (e.g., −75.32°, −74.10°, −73.21°) of the thermally-controlled block (prism) as a function of set point temperature. FIG. 16C is a plot of angular block position of minimum intensity over the angular positions of the thermally-controlled block (prism) as a function of set point temperature. FIG. 17 is a plot of differential nominal intensity for two particular angular positions (e.g., −75.32° and −74.10°) of the thermally-controlled block (prism) as a function of set point temperature.

DETAILED DESCRIPTION

Figure 1:
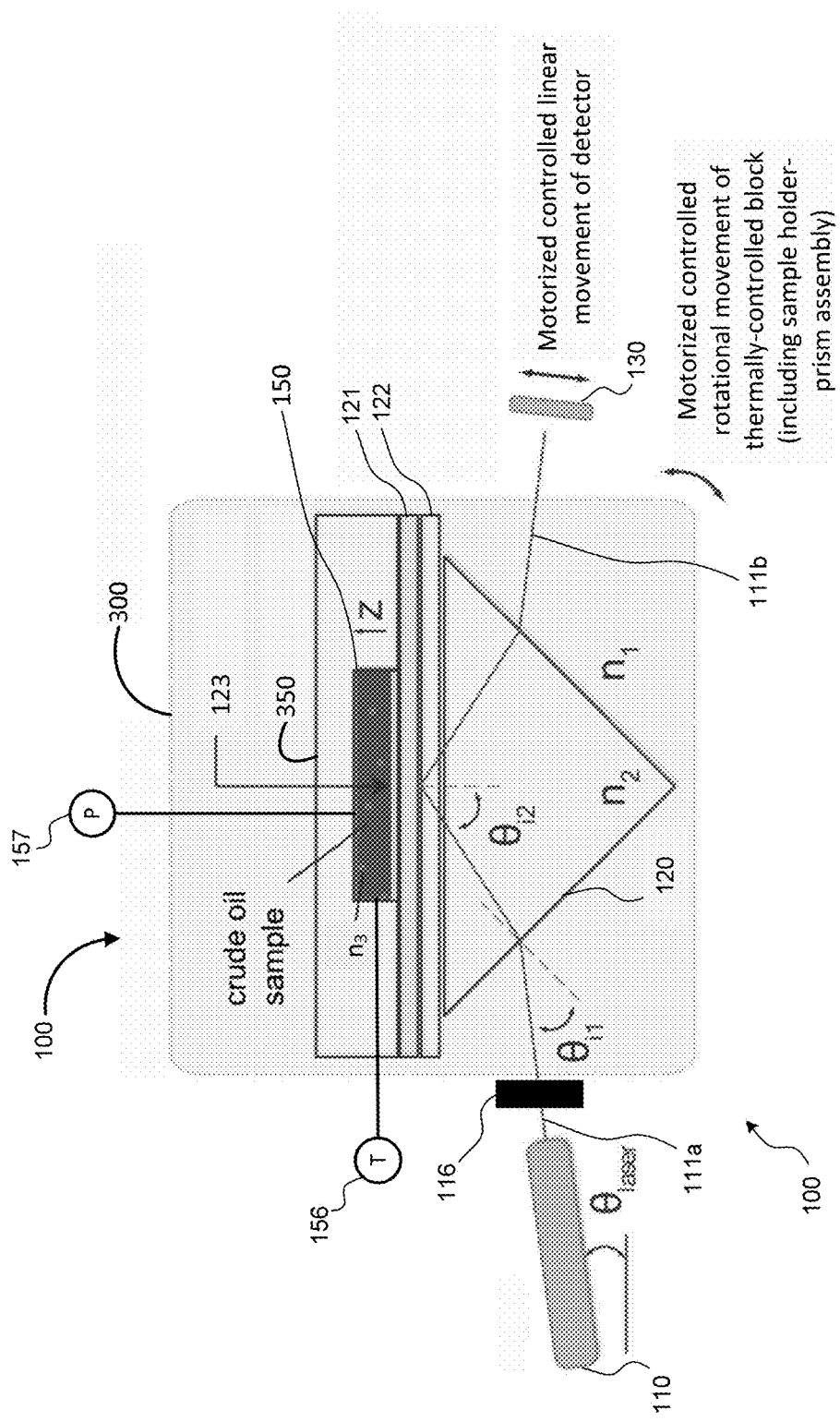
FIG. 1 is a schematic diagram illustrating a first embodiment of an SPR sensor configured to determine at least one property relating to phase change of a hydrocarbon-based analyte.

Before the present invention is described in greater detail, it is to be understood that aspects of the present disclosure are not limited to the particular embodiments described, and as such may, of course, vary. It is also to be understood that the terminology used herein is for the purpose of describing particular embodiments only, and is not intended to be limiting, since the scope of embodiments of the present disclosure will be defined only by the appended claims.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

The term "surface plasmon resonance" or "SPR" as used herein describes a condition in which light incident onto a surface of a highly conductive metallic film couples into resonant charge oscillations of the metallic film, resulting in light that is effectively trapped to the surface of the metallic film. In this trapped state, the light is sensitive to the dielectric environment in the immediate vicinity of the opposite surface of the metallic film (i.e., less than 1 μm away from the opposite surface of the metallic film). This condition is useful for detection of properties of an analyte that is deposited or located in the immediate vicinity of the opposite surface of the metallic film.

Systems/Methods

Systems and methods of the present disclosure employ an SPR (surface plasmon resonance) sensor that is configured to determine at least one property related to phase change of a hydrocarbon-based analyte induced by changes in temperature, pressure and/or composition of the hydrocarbon-based analyte. In some embodiments, the at least one property can be derived from experiments under constant pressure conditions where the temperature of the hydrocarbon-based analyte is controllably varied over a range of set point temperatures. In some embodiments, the at least one property can be derived from experiments under constant temperature conditions where the pressure of the hydrocarbon-based analyte is controllably varied over a range of set point pressures. In some embodiments, the at least one property can be derived from experiments with controlled variations in both the temperature and pressure conditions of the hydrocarbon-based analyte.

In some embodiments, the at least one property related to phase change of the hydrocarbon-based analyte can specify temperature and/or pressure conditions where components that are dissolved in the hydrocarbon-based analyte (such as wax components, asphaltenes, hydrates, scale or other inorganic material) precipitate and form solids. For example, the at least one property related to phase change of a hydrocarbon-based analyte can specify a Wax Appearance Temperature (WAT) where wax components that are dissolved in the hydrocarbon-based analyte first precipitate and form solid material. Alternatively, the at least one property related to phase change of a hydrocarbon-based analyte can specify temperature and/or pressure conditions where solid components of the hydrocarbon-based analyte (such as solid wax components, asphaltenes, hydrates, scale or other inorganic material) transition to a liquid phase.

In some embodiments, the at least one property related to phase change of the hydrocarbon-based analyte can specify temperature and/or pressure conditions where components of the hydrocarbon-based analyte (such as the heavier molecular weight components of a single phase gas condensate) transition from a gas phase to a liquid phase. In this case, the temperature and/or pressure conditions allow condensation of the heavier molecular weight components from the single phase gas condensate. Alternatively, the at least one property related to phase change of the hydrocarbon-based analyte can specify temperature and/or pressure conditions where components of the hydrocarbon-based analyte transition from a liquid phase to a gas phase.

In some embodiments, the at least one property related to phase change of the hydrocarbon-based analyte can specify bubble point temperature and/or pressure conditions where vapor forms from the hydrocarbon-based analyte or where vapor dissolve into the hydrocarbon-based analyte as induced by changes in temperature, pressure and/or composition of the hydrocarbon-based analyte. In this case, the at least one property related to phase change of the hydrocarbon-based analyte can be related to formation of vapor or liquid phases.

In some embodiments, the at least one property related to phase change of the hydrocarbon-based analyte can specify temperature and/or pressure conditions (typically referred to as ("asphaltene deposition onset conditions") where asphaltenes precipitate from the hydrocarbon-based analyte and deposit to form a solid film as induced by changes in temperature, pressure and/or composition of the hydrocarbon-based analyte. Alternatively, the at least one property related to phase change of the hydrocarbon-based analyte can be related to a phase transition of solid asphaltenes to liquid maltenes.

In some embodiments, the at least one property related to phase change of the hydrocarbon-based analyte can specify a fluid type of the hydrocarbon-based analyte when undergoing phase change.

In some embodiments, the SPR sensor can be configured to detect a phase transition or related property with respect to a hydrocarbon-based analyte where the phase transition or related property is induced by changes in temperature, pressure and/or composition of the hydrocarbon-based analyte In some embodiments, the SPR sensor can include a monochromatic light source. The monochromatic light source can be configured to direct a monochromatic light beam to a prism, which couples the incident monochromatic light beam onto an optical substrate that is coated with a thin noble metal film (metallic film) under conditions of total internal reflection. Alternatively, a face of the prism can be coated with the metallic film and the optical substrate can be omitted. At the point of reflection of the monochromatic light beam at the interface of the metallic film, surface plasmon resonance can occur where an evanescent field (standing wave) will penetrate beyond the metallic film in an SPR sensing zone that is in the immediate vicinity of the metallic film (i.e., less than 1 µm away). A sample cell is fixed in position relative to the prism and the metallic film/optical substrate as part of an assembly. The sample cell defines a sample chamber that is adjacent the metallic film. In this configuration, part of the sample chamber lies in the SPR sensing zone adjacent the metallic film. The other faces of the prism are unblocked to allow the monochromatic light beam to enter the prism and exit the prism after reflection at the interface of the metallic film.

The assembly can be mounted on a rotatable platform which is rotated by a motorized rotation stage. The operation of the rotation stage is controlled by a computer processing system to provide for controlled rotation of the platform/assembly in order to vary the angle of incidence of the monochromatic light supplied by the monochromatic light source relative to the input face of the prism, which varies the angle of incidence of the monochromatic light beam relative to the metallic film of the SPR sensor. A photodetector can be mounted to a platform which is secured to a motorized linear motion stage. The operation of the linear motion stage is controlled by the computer processing system such that as the platform/assembly rotates, the photodetector is moved along a trajectory that maintains alignment of the photodetector with the center of the reflected light beam that is output from the output face of the prism. The electrical signal output of the photodetector represents the intensity of the reflected light beam (which is sensitive to the surface plasmon resonance at the interface of the metallic film of the SPR sensor) that is output from the output face of the prism as the platform/assembly rotates. The electrical signal output of the photodetector can be processed by signal processing circuitry (such as an amplifier and analog-to-digital converter) such that the computer processing system generates and stores digital data that represents the intensity of the reflected light beam that is output from the output face of the prism as the platform/assembly rotates.

The assembly (e.g., the sample cell, prism and the metallic film/optical substrate) can include one or more temperature control elements (such as one or more heat exchangers and associated temperature controller, one or more Peltier thermal-electric elements and/or one or more heat sinks) for use in controlling the temperature of the sample cell and prism of the assembly during operation of the SPR sensor (including as the platform/assembly rotates). The assembly can include a temperature sensor (which can be integrated into the sample cell) that can interface to the computer processing system for use in monitoring and controlling the temperature of the sample cell and prism of the assembly during operation of the SPR sensor.

The SPR sensor can be configured to detect temperature and/or pressure conditions that induce phase transitions in a hydrocarbon-based analyte through experiments under constant pressure conditions where the temperature of the hydrocarbon-based analyte is controllably varied over a range of set point temperatures. In this case, the hydrocarbon-based analyte can be loaded into (or flowed through) the sample chamber of the SPR sensor at a set pressure (or set pressure differential between the inlet and outlet of the sample chamber). Pressure control of the hydrocarbon-based analyte can be established using one or more pressure control elements that control the pressure of the hydrocarbon-based analyte in the sample chamber to a set pressure (or pressure differential) as monitored by one or more pressure transducers. Such pressure control element(s) can include a pump (e.g., syringe pump) and possibly one or more isolation valves (e.g., an inlet valve and/or exhaust valve) that are in fluid communication with the sample chamber of the SPR sensor. With the hydrocarbon-based analyte at the controlled constant pressure conditions, the computer processing system can be configured to perform a sequence of test measurements over a range of set point temperatures. In each test measurement of the sequence, the computer processing system can be configured to perform a number of operations, including:

i) the computer processing system interfaces to the temperature control elements of the assembly to control the temperature of the hydrocarbon-based analyte, the sample cell and prism at the desired set point temperature of the specific test measurement as monitored by the temperature sensor of the assembly; the computer processing system can be configured to allow the temperature of the sample cell and prism to reach steady state at the set point temperature prior to acquiring the intensity measurements of the reflected light beam during controlled rotation of the platform/assembly as described in ii)-iv) below;

ii) the computer processing system controls the operation of the rotation stage to provide for controlled rotation of the platform/assembly over a predefined rotational range in order to vary the angle of incidence of the monochromatic light supplied by the monochromatic light source relative to the input face of the prism, which varies the angle of incidence of the monochromatic light beam relative to the metallic film of the SPR sensor;

iii) during such rotation, the computer processing system controls the operation of the linear motion stage such that the photodetector is moved along a trajectory that maintains alignment of the photodetector with the center of the reflected light beam that is output from the prism (which is sensitive to the surface plasmon resonance at the interface of the metallic film of the SPR sensor); and iv) during such rotation, the computer processing system processes the electrical signals output by the photodetector and signal processing circuitry in order to generate and store a record of intensity data as a function of angular position of the platform/assembly; the intensity data stored in the record represents the intensity of the reflected light beam that is output from the prism at respective angular positions of the platform/assembly as the platform/assembly rotates.

The hydrocarbon-based analyte can be loaded into the sample chamber of the sample cell by a pump (such as the pressure control syringe pump) and inlet valve. When the test measurements of the sequence are complete, the hydrocarbon-based analyte can be removed from the sample chamber of the sample cell through an exhaust valve and/or waste line. Alternatively, the hydrocarbon-based analyte can be flowed through the sample chamber of the sample cell during the test measurements by a pump (such as the pressure control syringe pump).

The record of intensity data as a function of angular position of the platform/assembly as stored by the computer processing system for the sequence of test measurements can be evaluated and/or processed in order to determine at least one property relating to phase change of the hydrocarbon-based analyte.

In some embodiments, the at least one property relating to phase change of the hydrocarbon-based analyte can detected from i) the set point temperature corresponding to a local minima or dip in the intensity data as a function of the angular position of the assembly (prism); ii) the set point temperature corresponding to an abrupt change in shape or slope of a local minima or dip in the intensity data as a function of the angular position of the assembly (prism); iii) the set point temperature corresponding to an abrupt change in the minimum of the intensity data over the angular positions of the assembly (prism) as a function of set point temperature; iv) the set point temperature corresponding to an abrupt change in the intensity data at a plurality of angular positions of the assembly (prism) as a function of set point temperature; v) the set point temperature corresponding to an abrupt change in the angle of minimum intensity data over the angular positions of the assembly (prism) as a function of set point temperature; and vi) the set point temperature corresponding to other signal metrics derived from the intensity data as a function of the angular position of the assembly (prism) as a function of set point temperature.

The SPR sensor can also be used to measure temperature and/or pressure conditions that induce phase transitions in a hydrocarbon-based analyte through experiments under constant temperature conditions where the pressure of the hydrocarbon-based analyte is controllably varied over a range of set point pressures. In this case, the temperature of the hydrocarbon-based analyte, the sample cell and prism of the SPR sensor is controlled to a desired set temperature. Temperature control can be established by using the temperature control elements of the assembly to control the temperature of the hydrocarbon-based analyte, the sample cell and prism at the desired set temperature as monitored by the temperature sensor of the assembly. With the hydrocarbon-based analyte at the controlled set temperature, the computer processing system can be configured to perform a sequence of test measurements over a range of set point pressures. In each test measurement of the sequence, the computer processing system can be configured to perform a number of operations, including:

i) the computer processing system interfaces to one or more pressure control elements that controls the pressure of the hydrocarbon-based analyte in the sample chamber at the set point pressure of the respective test measurement as monitored by one or more pressure transducers; such pressure control element(s) can include a pump (e.g., syringe pump) and possibly one or more isolation valves (e.g., an inlet valve and/or exhaust valve) that are in fluid communication with the sample chamber of the SPR sensor; the computer processing system can be configured to allow the pressure of the hydrocarbon-based analyte in the sample chamber (or the differential pressure of the hydrocarbon-based analyte flowing through the sample chamber) to reach steady state at the set point pressure prior to acquiring the intensity measurements of the reflected light beam during controlled rotation of the platform/assembly as described in ii)-iv) below;

ii) the computer processing system controls the operation of the rotation stage to provide for controlled rotation of the platform/assembly over a predefined rotational range in order to vary the angle of incidence of the monochromatic light supplied by the monochromatic light source relative to the input face of the prism, which varies the angle of incidence of the monochromatic light beam relative to the metallic film of the SPR sensor;

iii) during such rotation, the computer processing system controls the operation of the linear motion stage such that the photodetector is moved along a trajectory that maintains alignment of the photodetector with the center of the reflected light beam that is output from the prism (which is sensitive to the surface plasmon resonance at the interface of the metallic film of the SPR sensor); and iv) during such rotation, the computer processing system processes the electrical signals output by the photodetector and signal processing circuitry in order to generate and store a record of intensity data as a function of angular position of the platform/assembly; the intensity data stored in the record represents the intensity of the reflected light beam that is output from the prism at respective angular positions of the platform/assembly as the platform/assembly rotates.

The hydrocarbon-based analyte can be loaded into the sample chamber of the sample cell by a pump (such as the pressure control syringe pump) and inlet valve. When the test measurements of the sequence are complete, the hydrocarbon-based analyte can be removed from the sample chamber of the sample cell through an exhaust valve and/or waste line. Alternatively, the hydrocarbon-based analyte can be flowed through the sample chamber of the sample cell during the test measurements by a pump (such as the pressure control syringe pump).

The record of intensity data as a function of angular position of the platform/assembly as stored by the computer processing system for the sequence of test measurements can be evaluated and/or processed in order to determine at least one property relating to phase change of the hydrocarbon-based analyte.

In some embodiments, the at least one property relating to phase change of the hydrocarbon-based analyte can detected from i) the set point pressure corresponding to a local minima or dip in the intensity data as a function of the angular position of the assembly (prism); ii) the set point pressure corresponding to an abrupt change in shape or slope of a local minima or dip in the intensity data as a function of the angular position of the assembly (prism); iii) the set point pressure corresponding to an abrupt change in the minimum of the intensity data over the angular positions of the assembly (prism) as a function of set point pressure; iv) the set point pressure corresponding to an abrupt change in the intensity data for a plurality of angular positions of the assembly (prism) as a function of set point pressure; v) the set point pressure corresponding to an abrupt change in the angle of minimum intensity data over the angular positions of the assembly (prism) as a function of set point pressure; and vi) the set point pressure corresponding to other signal metrics derived from the intensity data as a function of the angular position of the assembly (prism) as a function of set point pressure.

The SPR sensor can also be used to measure temperature and pressure conditions that induce phase transitions in a hydrocarbon-based analyte through experiments with controlled variations in both the temperature and pressure conditions of the hydrocarbon-based analyte. In this case, the temperature of the hydrocarbon-based analyte, the sample cell and the prism of the SPR sensor can be controlled to a desired set temperature above the phase transition temperature—typically the sample's reservoir temperature. Temperature control can be established by using the temperature control elements of the assembly to control the temperature of the sample cell and prism at the desired set temperature as monitored by the temperature sensor of the assembly. With the hydrocarbon-based analyte at the controlled set temperature, the computer processing system can be configured to perform a sequence of test measurements over a range of set point pressures (referred to as a "pressure loop"). In each test measurement of the pressure loop, the computer processing system can be configured to perform a number of operations, including:

i) the computer processing system interfaces to one or more pressure control elements that controls the pressure of the hydrocarbon-based analyte in the sample chamber at the set point pressure of the respective test measurement as monitored by a pressure transducer; such pressure control element(s) can include a pump (e.g., syringe pump) and possibly one or more isolation valves (e.g., an inlet valve and/or exhaust valve) that are in fluid communication with the sample chamber of the SPR sensor; the computer processing system can be configured to allow the pressure of the hydrocarbon-based analyte in the sample chamber (or the differential pressure of the hydrocarbon-based analyte flowing through the sample chamber) to reach steady state at the set point pressure prior to acquiring the intensity measurements of the reflected light beam during controlled rotation of the platform/assembly as described in ii)-iv) below;

ii) the computer processing system controls the operation of the rotation stage to provide for controlled rotation of the platform/assembly over a predefined rotational range in order to vary the angle of incidence of the monochromatic light supplied by the monochromatic light source relative to the input face of the prism, which varies the angle of incidence of the monochromatic light beam relative to the metallic film of the SPR sensor;

iii) during such rotation, the computer processing system controls the operation of the linear motion stage such that the photodetector is moved along a trajectory that maintains alignment of the photodetector with the center of the reflected light beam that is output from the prism (which is sensitive to the surface plasmon resonance at the interface of the metallic film of the SPR sensor); and iv) during such rotation, the computer processing system processes the electrical signals output by the photodetector and signal processing circuitry in order to generate and store a record of intensity data as a function of angular position of the platform/assembly; the intensity data stored in the record represents the intensity of the reflected light beam that is output from the prism at respective angular positions of the platform/assembly as the platform/assembly rotates.

After the pressure loop is fully executed (or a phase transition has been detected), the computer processing system can be configured to control the pressure of the hydrocarbon-based analyte such that such pressure returns to reservoir pressure. If necessary, the computer processing system can control temperature of the sample cell and prism by decrementing such temperature by a set amount, and the pressure loop is executed again. The temperature parent loop (along with the children pressure loops) can be executed until a lower temperature limit is reached. The pressure loops and temperature loops can be executed independently or in a nested manner as required by the type of phase transition targeted.

The hydrocarbon-based analyte can be loaded into the sample chamber of the sample cell by a pump (such as the pressure control syringe pump) and inlet valve. When the pressure loops and temperature loops are complete, the hydrocarbon-based analyte can be removed from the sample chamber of the sample cell through an exhaust valve and/or waste line. Alternatively, the hydrocarbon-based analyte can be flowed through the sample chamber of the sample cell during the test measurements by a pump (such as the pressure control syringe pump).

The record of intensity data as a function of angular position of the platform/assembly as stored by the computer processing system over the test measurements of the pressure loops and temperature loops can be evaluated and/or processed in order to determine at least one property relating phase change of the hydrocarbon-based analyte.

In some embodiments, the at least one property relating to phase change of the hydrocarbon-based analyte can detected from i) the temperature and pressure corresponding to a local minima or dip in the intensity data as a function of the angular position of the assembly (prism) for a particular controlled temperature and pressure; ii) the temperature and pressure corresponding to an abrupt change in shape or slope of a local minima or dip in the intensity data as a function of the angular position of the assembly (prism); iii) the temperature and pressure corresponding to an abrupt change in the minimum of the intensity data over the angular positions of the assembly (prism) as a function of set point pressure at a particular controlled temperature; iv) the temperature and pressure corresponding to an abrupt change in the intensity data for a plurality of angular positions of the assembly (prism) as a function of set point pressure at a particular controlled temperature; v) the temperature and pressure corresponding to an abrupt change in the angle of minimum intensity data over the angular positions of the assembly (prism) as a function of set point pressure at a particular controlled temperature; and vi) the temperature and pressure corresponding to other signal metrics derived from the intensity data as a function of the angular position of the assembly (prism) as a function of set point pressure at a particular controlled temperature.

In some embodiments, the monochromatic light source of the SPR sensor can include a laser (such as a HeNe laser supplying radiation at a wavelength of 632 nm), a linear polarizer, and a mechanical chopper. The linear polarizer can be configured to polarize the monochromatic light beam generated by the laser such that the polarization of the monochromatic light beam is in the transverse-magnetic orientation relative to the metallic film of the SPR sensor. The mechanical chopper can be configured to modulate the monochromatic light beam at a predefined measurement frequency (such as a measurement frequency between 1000 and 1300 Hz). In the configuration, the signal processing circuitry that processes the electrical signals output by the photodetector can include a lock-in amplifier that is synchronized to the modulation operations of the mechanical chopper such that the lock-in amplifier isolates the detected signal at the predefined measurement frequency and eliminates the effect of ambient light.

In some embodiments, the computer processing system of the SPR sensor can generate and store intensity data based on the electrical signal generated by the photodetector for test measurements involving controlled rotational movement of the prism relative to the monochromatic light source with the hydrocarbon-based analyte loaded into the sample chamber (or flowing-thru the sample chamber). The computer processing system can process the intensity data as a function of angular positions of the prism relative to the monochromatic light to detect a phase transition with respect to the hydrocarbon-based analyte and/or determine at least one property relating to a phase transition of the hydrocarbon-based analyte. For example, the intensity data corresponding to different angular positions of the prism relative to the monochromatic light source can be evaluated to detect a phase change or related property with respect to the hydrocarbon-based analyte based on abrupt changes or other signal metrics measured from intensity data.

In some embodiments, the SPR sensor can include a polychromatic light source. The polychromatic light source can be configured to direct a polychromatic light beam to a prism, which couples the incident polychromatic light beam onto an optical substrate that is coated with a thin semi-transparent noble metal film (metallic film) under conditions of total internal reflection. Alternatively, a face of the prism can be coated with the metallic film and the optical substrate can be omitted. Similar to the embodiment that utilizes a monochromatic light source, at the point of reflection of the polychromatic light beam at the interface of the metallic film, surface plasmon resonance can occur where an evanescent field (standing wave) will penetrate beyond the metallic film in an SPR sensing zone that is in the immediate vicinity of the metallic film (i.e., less than 1 µm away). A sample cell is fixed in position relative to the prism and the metallic film/optical substrate as part of an assembly. The sample cell defines a fixed-volume sample chamber that is adjacent the metallic film. In this configuration, part of the fixed-volume sample chamber lies in the SPR sensing zone adjacent the metallic film. The other faces of the prism are unblocked to allow the polychromatic light beam to enter the prim and exit the prism after reflection at the interface of the metallic film. A spectrometer is configured to receive the reflected light beam that is output from the output face of the prism. The spectrometer measures an SPR spectrum that represents the intensity of the reflected light beam that is output from the output face of the prism as a function of wavelength. The SPR spectrum measured by the spectrometer is sensitive to the surface plasmon resonance at the interface of the metallic film of the SPR sensor.

Similar to the embodiment that utilizes a monochromatic light source and prism, the assembly (e.g., the sample cell, prism and the metallic film/optical substrate) can include one or more temperature control elements (such as one or more heat exchangers and associated temperature controller, one or more Peltier thermal-electric elements and/or one or more heat sinks) for use in controlling the temperature of the sample cell and prism of the assembly during operation of the SPR sensor. The assembly can also include a temperature sensor (which is preferably integrated into the sample cell) that can interface to the computer processing system for use in monitoring and controlling the temperature of the sample cell and prism of the assembly during operation of the SPR sensor.

Note that the SPR sensor utilizing the polychromatic light source and spectrometer avoids the use of mechanical moving parts (e.g., the rotation and linear motion stages and driving motor and positions sensors) of the SPR sensor embodiment utilizing the monochromatic light source and photodetector.

The SPR sensor utilizing the polychromatic light source and spectrometer can be used to detect temperature and/or pressure conditions that induce phase transitions in a hydrocarbon-based analyte through experiments under constant pressure conditions where the temperature of the hydrocarbon-based analyte is controllably varied over a range of set point temperatures. In this case, the hydrocarbon-based analyte can be loaded into (or flowed through) the sample chamber of the SPR sensor at a set pressure (or set pressure differential between the inlet and outlet of the sample chamber). Pressure control of the hydrocarbon-based analyte can be established using one or more pressure control elements that control the pressure of the hydrocarbon-based analyte in the sample chamber to a set pressure (or pressure differential) as monitored by one or more pressure transducers. Such pressure control element(s) can include a pump (e.g., syringe pump) and possibly one or more isolation valves (e.g., an inlet valve and/or exhaust valve) that are in fluid communication with the sample chamber of the SPR sensor. With the hydrocarbon-based analyte at the controlled constant pressure conditions, the computer processing system can be configured to perform a sequence of test measurements over a range of set point temperatures. In each test measurement of the sequence, the computer processing system can be configured to perform a number of operations, including:

i) the computer processing system interfaces to the temperature control elements of the assembly to control the temperature of the hydrocarbon-based analyte, the sample cell and the prism at the desired set point temperature of the specific test measurement as monitored by one or more temperature sensors of the assembly; the computer processing system can be configured to allow the temperature of the hydrocarbon-based analyte, the sample cell and the prism to reach steady state at the set point temperature prior to acquisition of the SPR spectrum in ii) below; and ii) the computer processing system acquires and stores the SPR spectrum output by the spectrometer; the SPR spectrum represents the intensity of the reflected light beam that is output from the output face of prism as a function of wavelength; the SPR spectrum is sensitive to the surface plasmon resonance at the interface of the metallic film of the SPR sensor).

The hydrocarbon-based analyte can be loaded into the sample chamber of the sample cell by a pump (such as the pressure control syringe pump) and inlet valve. When the test measurements of the sequence are complete, the hydrocarbon-based analyte can be removed from the sample chamber of the sample cell through an exhaust valve and/or waste line. Alternatively, the hydrocarbon-based analyte can be flowed through the sample chamber of the sample cell during the test measurements by a pump (such as the pressure control syringe pump).

The SPR spectra stored by the computer processing system for the sequence of test measurements can be evaluated and/or processed in order to determine at least one property relating to phase change of the hydrocarbon-based analyte.

In some embodiments, the at least one property relating to phase change of the hydrocarbon-based analyte can detected by identifying a temperature condition that produces a shift in a local minima or dip in the SPR spectra or by identifying a temperature condition that produces other signal metrics derived from the SPR spectra.

The SPR sensor utilizing the polychromatic light source and spectrometer can also be used to measure temperature and/or pressure conditions that induce phase transitions in a hydrocarbon-based analyte through experiments under constant temperature conditions where the pressure of the hydrocarbon-based analyte is controllably varied over a range of set point pressures. In this case, the temperature of the hydrocarbon-based analyte, the sample cell and prism of the SPR sensor is controlled to a desired set temperature. Temperature control can be established by using the temperature control elements of the assembly to control the temperature of the hydrocarbon-based analyte, the sample cell and prism at the desired set temperature as monitored by the temperature sensor of the assembly. With the hydrocarbon-based analyte at the controlled set temperature, the computer processing system can be configured to perform a sequence of test measurements over a range of set point pressures. In each test measurement of the sequence, the computer processing system can be configured to perform a number of operations, including:

i) the computer processing system interfaces to one or more pressure control elements that controls the pressure of the hydrocarbon-based analyte in the sample chamber at the set point pressure of the respective test measurement as monitored by one or more pressure transducers; such pressure control element(s) can include a pump (e.g., syringe pump) and possibly one or more isolation valves (e.g., an inlet valve and/or exhaust valve) that are in fluid communication with the sample chamber of the SPR sensor; the computer processing system can be configured to allow the pressure of the hydrocarbon-based analyte in the sample chamber (or the differential pressure of the hydrocarbon-based analyte flowing through the sample chamber) to reach steady state at the set point pressure prior to acquiring the SPR spectrum as described in ii) below; and ii) the computer processing system acquires and stores the SPR spectrum output by the spectrometer; the SPR spectrum represents the intensity of the reflected light beam that is output from the output face of prism as a function of wavelength; the SPR spectrum is sensitive to the surface plasmon resonance at the interface of the metallic film of the SPR sensor.

The hydrocarbon-based analyte can be loaded into the sample chamber of the sample cell by a pump (such as the pressure control syringe pump) and inlet valve. When the test measurements of the sequence are complete, the hydrocarbon-based analyte can be removed from the sample chamber of the sample cell through an exhaust valve and/or waste line. Alternatively, the hydrocarbon-based analyte can be flowed through the sample chamber of the sample cell during the test measurements by a pump (such as the pressure control syringe pump).

The SPR spectra stored by the computer processing system for the sequence of test measurements can be evaluated and/or processed in order to determine at least one property relating to phase change of the hydrocarbon-based analyte.

In some embodiments, the at least one property relating to phase change of the hydrocarbon-based analyte can detected by identifying a pressure condition that produces a shift in a local minima or dip in the SPR spectra or by identifying a pressure condition that produces other signal metrics derived from the SPR spectra.

The SPR sensor utilizing the polychromatic light source and spectrometer can also be used to measure temperature and pressure conditions that induce phase transitions in a hydrocarbon-based analyte through experiments with controlled variations in both the temperature and pressure conditions of the hydrocarbon-based analyte. In this case, the temperature of the hydrocarbon-based analyte, the sample cell and the prism of the SPR sensor can be controlled to a desired set temperature above the phase transition temperature—typically the sample's reservoir temperature. Temperature control can be established by using the temperature control elements of the assembly to control the temperature of the sample cell and prism at the desired set temperature as monitored by the temperature sensor of the assembly. With the hydrocarbon-based analyte at the controlled set temperature, the computer processing system can be configured to perform a sequence of test measurements over a range of set point pressures (referred to as a "pressure loop"). In each test measurement of the pressure loop, the computer processing system can be configured to perform a number of operations, including:

i) the computer processing system interfaces to one or more pressure control elements that controls the pressure of the hydrocarbon-based analyte in the sample chamber at the set point pressure of the respective test measurement as monitored by a pressure transducer; such pressure control element(s) can include a pump (e.g., syringe pump) and possibly one or more isolation valves (e.g., an inlet valve and/or exhaust valve) that are in fluid communication with the sample chamber of the SPR sensor; the computer processing system can be configured to allow the pressure of the hydrocarbon-based analyte in the sample chamber (or the differential pressure of the hydrocarbon-based analyte flowing through the sample chamber) to reach steady state at the set point pressure prior to acquiring the SPR spectrum as described in ii) below; and ii) the computer processing system acquires and stores the SPR spectrum output by the spectrometer; the SPR spectrum represents the intensity of the reflected light beam that is output from the output face of prism as a function of wavelength; the SPR spectrum is sensitive to the surface plasmon resonance at the interface of the metallic film of the SPR sensor.

After the pressure loop is fully executed (or a phase transition has been detected), the computer processing system can be configured to control the pressure of the hydrocarbon-based analyte such that such pressure returns to reservoir pressure. If necessary, the computer processing system can control temperature of the sample cell and prism by decrementing such temperature by a set amount, and the pressure loop is executed again. The temperature parent loop (along with the children pressure loops) can be executed until a lower temperature limit is reached. The pressure loops and temperature loops can be executed independently or in a nested manner as required by the type of phase transition targeted.

The hydrocarbon-based analyte can be loaded into the sample chamber of the sample cell by a pump (such as the pressure control syringe pump) and inlet valve. When the pressure loops and temperature loops are complete, the hydrocarbon-based analyte can be removed from the sample chamber of the sample cell through an exhaust valve and/or waste line. Alternatively, the hydrocarbon-based analyte can be flowed through the sample chamber of the sample cell during the test measurements by a pump (such as the pressure control syringe pump).

The SPR spectra stored by the computer processing system over the test measurements of the pressure loops and temperature loops can be evaluated and/or processed in order to determine at least one property relating to phase change of the hydrocarbon-based analyte.

In some embodiments, the at least one property relating to phase change of the hydrocarbon-based analyte can detected by identifying temperature and pressure conditions that produce a shift in a local minima or dip in the SPR spectra or by identifying temperature and pressure conditions that produces other signal metrics derived from the SPR spectra.

In some embodiments, the polychromatic light source of the SPR sensor can include a broadband light source (e.g., a broadband tungsten-halogen light source) and a collimator. The collimator can be configured to collimate the polychromatic light beam generated by the broadband light source for supply to the prism. In the configuration, the SPR sensor can employ a linear polarizer and collimator in the optical path between the output face of the prism and the spectrometer.

In some embodiments, the computer processing system of the SPR sensor can generate and store spectral data based on the output of the spectrometer for test measurements with the hydrocarbon-based analyte loaded into the sample chamber (or flowing-thru the sample chamber). The computer processing system can process the spectral data to detect a phase transition with respect to the hydrocarbon-based analyte and/or determine at least one property relating to a phase transition of the hydrocarbon-based analyte. For example, the spectral data can be evaluated to detect a phase change or phase transition property with respect to the hydrocarbon-based analyte based on local minima shift or other signal metric measured from spectral data.

In some embodiments, the SPR sensors as described herein can include a pulsed-mode electrical source (such as a pulsed-mode current source or pulsed-mode voltage source) that interfaces to the metallic film of the SPR sensor and operates to induce pulsed-mode heating of the metallic film that heats the localized hydrocarbon-based fluid in sample chamber in the vicinity of the metallic film. During the off-cycle of the pulse-mode heating, the metallic film returns to or near the set point temperature of the sample cell and prism. During the on-cycle of the pulsed-mode heating, the metallic film provides resistive heating thereby raising the temperature of the metallic film above the set point temperature of the sample cell and prism. The magnitude of the electrical driving power can be configured to provide user selectable temperature cycling. At conditions of interest, the temperature cycling provided by the pulsed-mode heating can produce a drastic change in the local refractive index within the vicinity of the metallic film and would show up as an abrupt change in the minimum intensity of the reflected light beam as detected by the photodetector. The change in the minimum intensity of the reflected light beam over time can possibly yield a square wave signal, matching the frequency of the driving current. This response can be detected in order to determine the at least one property relating to phase change of the hydrocarbon-based analyte, which improve the accuracy and signal-to-noise ratio of the measurement.

In some embodiments, the SPR sensors as described herein are integrated as part of a downhole tool or surface-located sensor that analyzes produced fluids. In this case, such SPR sensors are configured to withstand the high pressure and high temperature oilfield conditions, e.g., conditions downhole in a borehole in a subterranean formation or at the surface.

In some embodiments, the SPR sensors as described herein can be used as part of a laboratory apparatus in order to test and analyze hydrocarbon-based analytes, such as formation fluid that is collected from subterranean formations by downhole tools.

Utility

The systems and methods as disclosed herein can be used to determine at least one property relating to phase change of a hydrocarbon-based analyte where the phase change is induced by change in temperature, pressure and/or composition of the hydrocarbon-based analyte.

In some embodiments, the at least one property related to phase change of the hydrocarbon-based analyte can specify temperature and/or pressure conditions where components that are dissolved in the hydrocarbon-based analyte (such as wax components, asphaltenes, hydrates, scale or other inorganic material) precipitate and form solids. For example, the at least one property related to phase change of a hydrocarbon-based analyte can specify a Wax Appearance Temperature (WAT) where wax components that are dissolved in the hydrocarbon-based analyte first precipitate and form solid material. Alternatively, the at least one property related to phase change of a hydrocarbon-based analyte can specify temperature and/or pressure conditions where solid components of the hydrocarbon-based analyte (such as solid wax components, asphaltenes, hydrates, scale or other inorganic material) transition to a liquid phase.

In some embodiments, the at least one property related to phase change of the hydrocarbon-based analyte can specify temperature and/or pressure conditions where components of the hydrocarbon-based analyte (such as the heavier molecular weight components of a single phase gas condensate) transition from a gas phase to a liquid phase. In this case, the temperature and/or pressure conditions allow condensation of the heavier molecular weight components from the single phase gas condensate. Alternatively, the at least one property related to phase change of the hydrocarbon-based analyte can specify temperature and/or pressure conditions where components of the hydrocarbon-based analyte transition from a liquid phase to a gas phase.

In some embodiments, the at least one property related to phase change of the hydrocarbon-based analyte can specify bubble point temperature and/or pressure conditions where vapor forms from the hydrocarbon-based analyte or where vapor dissolve into the hydrocarbon-based analyte as induced by changes in temperature, pressure and/or composition of the hydrocarbon-based analyte. In this case, the at least one property related to phase change of the hydrocarbon-based analyte can be related to formation of vapor or liquid phases.

In some embodiments, the at least one property related to phase change of the hydrocarbon-based analyte can specify temperature and/or pressure conditions (typically referred to as ("asphaltene deposition onset conditions") where asphaltenes precipitate from the hydrocarbon-based analyte and deposit to form a solid film as induced by changes in temperature, pressure and/or composition of the hydrocarbon-based analyte. Alternatively, the at least one property related to phase change of the hydrocarbon-based analyte can be related to a phase transition of solid asphaltenes to liquid maltenes.

In some embodiments, the at least one property related to phase change of the hydrocarbon-based analyte can specify a fluid type of the hydrocarbon-based analyte when undergoing phase change.

In some embodiments, the systems and methods as disclosed herein can be used to detect phase change or a related property of a hydrocarbon-based analyte where the phase change or related property is induced by change in temperature, pressure and/or composition of the hydrocarbon-based analyte.

The systems and methods as disclosed herein find use in oil field and gas field applications, such as in downhole fluid analysis of formation fluids or surface-located facilities that analyze produced fluids. It also has other applications in the distribution and storage of hydrocarbon fluids for testing the hydrocarbon fluid.

EXAMPLES

There are a wide variety of issues encountered in reservoir engineering and other oilfield applications that relate to phase changes in hydrocarbon-based reservoir fluids.

For example, the deposition of waxes contained in crude oils can be a major problem during oil production, transportation, and processing, causing complications such as reduced oil extraction from the reservoir, clogging of pipelines and wellbores, adsorption onto refining equipment, and plugging during storage. These problems are exacerbated in subsea offshore environments and in colder climates, where crude oil is exposed to large temperature gradients. Such waxes or wax components are typically comprised of long-chain hydrocarbons (e.g. n-paraffins) with carbon chain lengths ranging from C17 to C90+. Such waxes are soluble in the oil liquid phase at reservoir conditions. However, when the crude oil temperature drops, the high molecular weight waxes can become less soluble in the liquid and dissolved wax molecules tend to crystallize and form solid particles. The solid particles of wax can deposit on solid surfaces. Such wax deposition is generally due to fluctuations in temperature; however, pressure and composition changes also induce deposition. Wax deposition Management of wax deposition requires rapid identification of problematic oils and accurate characterization of wax behavior. Conventional methods for wax measurement often rely on bulk analysis of subsamples—workflows involve on-site sample collection and off-site laboratory analysis by a trained operator. Oil samples are captured in specialized steel cylinders at reservoir conditions. Samples are then transported to a laboratory where wax content and deposition behavior is quantified, typically by cross-polarization microscopy (CPM), differential scanning calorimetry (DSC) and weight measurements using a conventional balance. Wax deposition can be evaluated by monitoring pressure drop and deposited wax mass/thickness from flow loop experiments or cold-finger systems. Wax deposition can also be evaluated by attenuated total reflectance (ATR) at a glass surface (for example, this approach is used by commercially available deposition detection technology developed by Teledyne Analytical Instruments of the City of Industry, California.

It is common to measure the wax appearance temperature (WAT) of a crude oil. WAT is defined as the temperature at which wax first precipitates from a crude oil sample. There are several disadvantages to these widely-used measurement strategies. First, there is a long delay (often weeks to months) between sample collection and wax analysis. Second, sample handling during collection, transportation, and testing can cause large variations in measurement. Third, wax evaluation in the laboratory provides only a proxy measure of wax deposition in the field, as testing conditions in the laboratory do not emulate conditions on-site. Many of these limitations can be overcome by developing portable sensor technologies that bypass sample collection and transportation and enable immediate on-site identification of the onset and degree of deposition.

Figure 24:
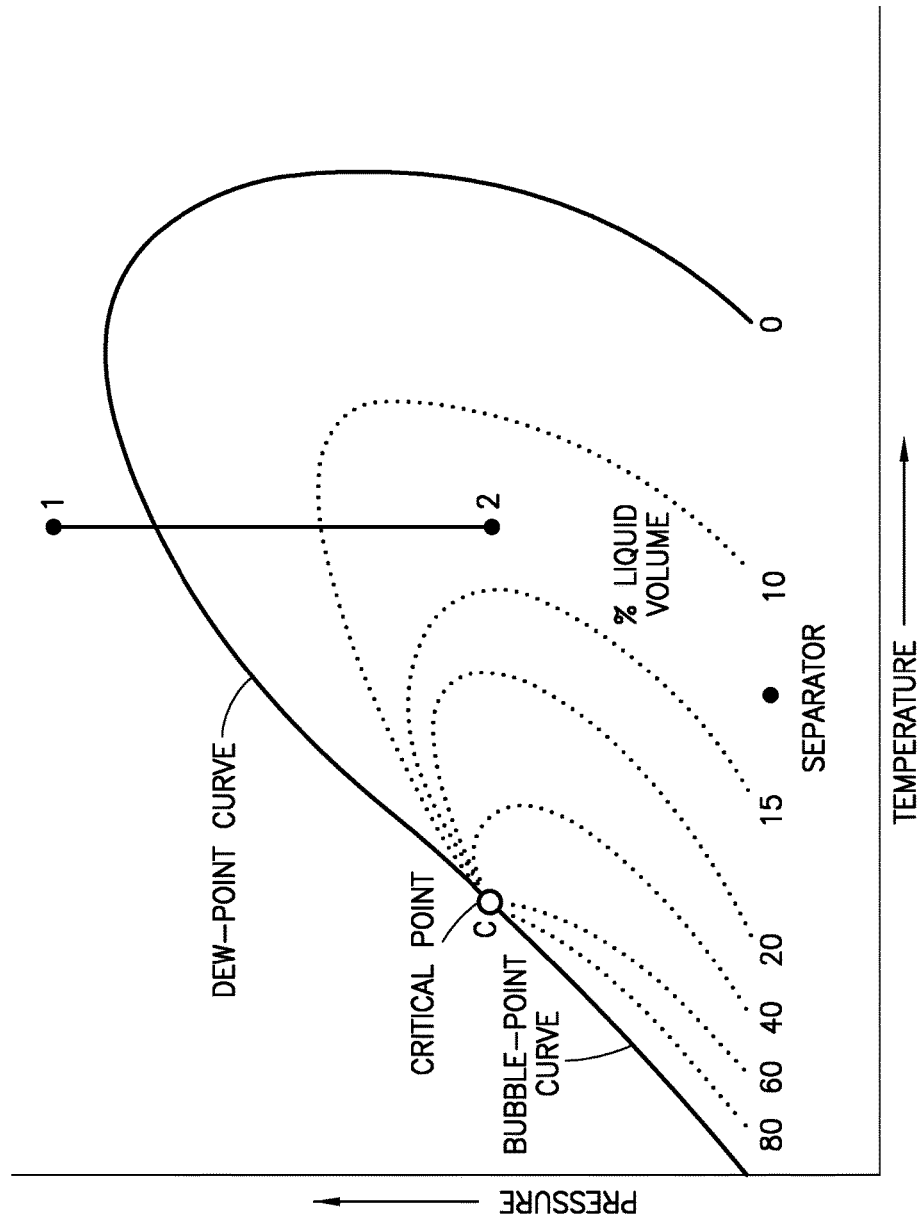
FIG. 24 is a phase diagram of a gas condensate, showing phase boundaries and conditions under which multiple phases can coexist at equilibrium.

In another example, hydrocarbon reservoir fluids can experience gas-to-liquid and liquid-to-gas phase transitions that occur as the pressure and temperature of the hydrocarbon reservoir fluids deviates from reservoir conditions. Retrograde condensates are one type of hydrocarbon fluid that exhibit a dewpoint (formation of a liquid phase from a gas phase) during isothermal depressurization at the temperature of interest. Presence of the liquid phase depends on temperature and pressure conditions in the reservoir allowing condensation of liquid from vapor. FIG. 24 shows the phase diagram of a typical gas condensate. The fluid is in gaseous form at pressures above the solid curve, while it forms liquid condensate once the pressure drops below the solid curve. Point 1 in FIG. 24 represents the gaseous state of the system at a given temperature. As the pressure drops at constant temperature, the system crosses the dew point curve (solid curve) and liquid phase forms (phase transition from gas-to-liquid). Point 2 in FIG. 24 depicts the two-phase state of the system. Formation of liquid phase in the pores during production of a gas field results in reduced liquid recovery. Condensate dropout near the wellbore can significantly reduce the productivity index of the well. In severe cases the well can prematurely die decreasing overall recovery under naturally flowing conditions. Therefore, it is imperative to measure the dew point as well as liquid drop-out of such hydrocarbon fluids at reservoir condition and plan the production accordingly.

Phase behavior studies of lean gas condensates are of growing importance in reservoir fluid analysis. Saturation pressure ($p_{sat}$) or the dew point of a gas condensate is an important thermo-physical property of such fluids. However, measurement of the dew point is usually difficult to perform in conventional Pressure-Volume-Temperature (PVT) systems. The complications stem from the difficulty in detecting and quantifying very small volumes of liquid in the gas. The dew point measurement becomes increasingly difficult as the liquid content of the gas reduces. Dead volumes in conventional PVT cells limit the minimum measurable liquid volumes. The minimum liquid volume fraction is a function of cell geometry. Conventional methods using PVT cells run into major difficulties when it comes to measuring the dew point of fluids with small volume liquid content (e.g., lean condensate). There have been attempts to increase the cell volume (e.g., 205 cc in Sanchez Gas 250-1000 cell) to increase the amount of liquid collected at and below dew point pressure. However, the increase in accuracy comes at the cost of significantly larger sample volume and operational difficulty. Furthermore, conventional techniques suffer from poor repeatability, reproducibility, and accuracy. Hence, there is a strong demand for a reliable, accurate and highly sensitive technique for dew point and phase volume measurement.

In yet another example, the determination of asphaltene onset conditions and also the amount of asphaltene precipitation under varying conditions are essential measurements for both upstream and downstream operations. It is useful to characterize asphaltene behavior to optimize flow assurance and to prevent adverse asphaltene drop out during production and processing of the oil. Asphaltenes are the most polar components in crude oil and are defined by their solubility; e.g., asphaltenes are soluble in toluene and insoluble in heptane (ASTM D6560, 2005). Asphaltenes can deposit in reservoirs, wellbore tubing, flow-lines, separators, etc. The deposits can interrupt and potentially stop production due to the formation of plugs. The first step in the deposition process is flocculation (aggregation) of molecules. During production, the solubility of the asphaltenes in the crude oil decreases as the pressure decreases as the fluid travels through the reservoir and the well bore. The asphaltene onset pressure (AOP) is the pressure at which asphaltenes first begin to precipitate at a fixed temperature. Asphaltene deposition can begin deep in the wellbore while the pressure is well above the bubble point. Asphaltenes can also precipitate during miscible flooding with CO2 and natural gases as well as due to comingling of different fluids.

Currently, the asphaltene onset condition (pressure, temperature, and composition) in crude oil is determined by systematic depressurization (at constant temperature) of the sample in PVT cell in the laboratory. In the cell, precipitation of asphaltene is detected based on visual observation and light scattering. Another approach for detecting the onset of asphaltene precipitation and yield is to measure the crude oil refractive index during temperature, pressure, or composition perturbations. Buckley, J. S., *Predicting the Onset of Asphaltene Precipitation from Refractive Index Measurements*. Energy & Fuels, 1999, 13(2): p. 328-332 presents a graph of the measured refractive index (RI) for a mixture of n-heptane and oil. The mixture RI gradually decreases as n-heptane is added to a sample crude oil. When the asphaltene onset condition is reached, the mixture RI sharply decreases indicated by a difference in slopes. Sudden changes in RI indicate a phase transition. Surface plasmon resonance (SPR) spectra can also be used to determine the refractive index of the sample, which in turn may be used to measure solubility parameters of hydrocarbon fluids.

In accordance with some example embodiments, systems and methods are provided for measuring at least one property related to phase change of a hydrocarbon-based analyte, such as wax appearance temperature, dew point, bubble point and asphaltene onset pressure (AOP). In some example embodiments, these measurements can be conducted at high pressure and high temperature reservoir conditions found in downhole environments. The systems and methods utilizes surface plasmon resonance to detect conditions when phase transitions of the hydrocarbon-based analyte are induced by pressure, temperature, or composition changes.

First Illustrative Embodiment

Figure 2:
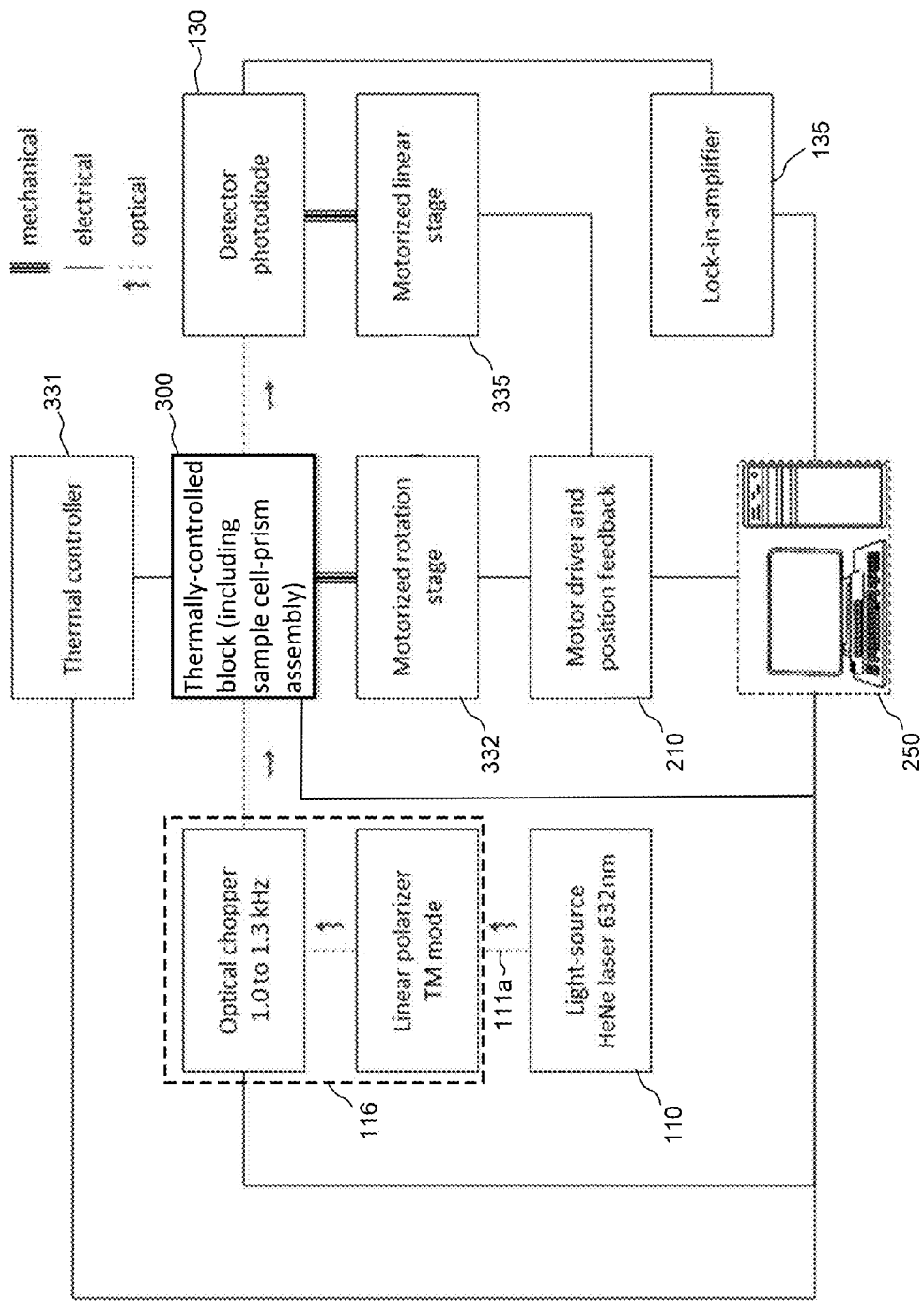
FIG. 2 is a block diagram of components of the first embodiment SPR sensor of FIG. 1.

A first illustrative embodiment of an SPR sensor is shown in FIGS. 1 and 2, which includes a sensor head 100 as shown in FIG. 1 and the associated support systems as shown in FIG. 2. The sensor head 100 includes several optical parts including a monochromatic light source 110 (e.g., laser), a linear polarizer and mechanical chopper (labeled together as block 116 in FIG. 1), a prism 120, and a photodetector 130. In the illustrative example, the monochromatic light source 110 can be a HeNe laser supplying radiation at a wavelength of 632 nm, although other light sources and/or wavelengths or combinations may be used as desired. The laser beam 111a produced by the monochromatic light source 110 is directed through the linear polarizer so that the polarization of the beam is in the transverse-magnetic orientation relative to the metallic film 121 described below. The mechanical chopper (which is also commonly referred to as an optical chopper) modulates the polarized laser beam at a predefined measurement frequency. In some embodiments, the predefined measurement frequency is between 1000 to 1300 Hz. The mechanical copper can be a mechanical chopper sold by Stanford Research Systems of Sunnyvale, Calif. The polarized modulated laser beam output from the mechanical chopper is directed into the prism 120, which couples the laser beam onto an optical substrate 122 that is coated with a thin noble metal film (metallic film 121) under conditions of total internal reflection. Alternatively, a face of the prism can be coated with a metal to form the metallic film 121 and the optical substrate can be omitted. In some embodiments, the metallic film 121 is realized from gold. In some embodiments, other suitable metals can be used for the metallic film 121. In some examples, the optical substrate 122 has a refractive index that matches the refractive index $n_2$ of the prism 120. The polarized modulated laser beam that is incident on the metallic film 121 is reflected from the interface of the metallic film 121 and then output from the output face of the prism 120 where it is captured by the photodetector 130. The electrical signal output of the photodetector 130 is supplied to a lock-in amplifier 135. The operation of the lock-in amplifier 135 is synchronized to the modulation operations of the mechanical chopper such that the lock-in amplifier 135 isolates the detected signal at the predefined measurement frequency and eliminates the effect of ambient light. The lock-in amplifier 135 can be a lock-in amplifier sold by Stanford Research Systems of Sunnyvale, Calif.

The SPR sensor head 100 operates under conditions that satisfy the surface plasmon resonance coupling condition. Specifically, at the point of reflection of the monochromatic light beam at the interface of the metallic film 121, surface plasmon resonance can occur where an evanescent field (standing wave) will penetrate beyond the metallic film 121 in an SPR sensing zone 123 that is in the immediate vicinity of the metallic film 121 (i.e., less than 1 μm away). For the configuration of FIG. 1, the surface plasmon resonance coupling condition is given by:

$$n_2 \sin\theta_{spr} = \sqrt{\frac{\varepsilon_m \varepsilon_d(T)}{\varepsilon_m + \varepsilon_d(T)}} . \qquad (1)$$

where $n_2$ is the refractive index of the prism 120, $\theta_{spr}$ is the angle of incidence ($\theta_{i2}$) of the light beam on the metallic film under SPR conditions, $\varepsilon_d(T)$ is the temperature-dependent permittivity of the hydrocarbon-based analyte in the SPR sensing zone 123 on the other side of the metallic film 121, and $\varepsilon_m$ is the permittivity of the metallic film 121. When the angle $\theta_{i2}$ satisfies the SPR condition ($\theta_{i2}=\theta_{spr}$, the reflected light beam intensity can diminish dramatically. Because the SPR condition is sensitive to environmental conditions in the SPR sensing zone 123, it is ideal for probing local surface-sensitive phenomena such as phase transitions of a hydrocarbon-based analyte in the SPR sensing zone 123 which can occur due to precipitation and/or deposition, condensation and evaporation. The permittivity of the hydrocarbon-based analyte in the SPR sensing zone 123 can be mathematically related to the angle of incidence of the light beam using Equation (1). Real-time changes in the permittivity of the hydrocarbon-based analyte in the SPR sensing zone 123 can be monitored by varying the angle of incidence of the light beam and detecting or measuring shifts in the angle of incidence of the light beam that results in minimal intensity of the reflect light that is captured by the photodetector 130. More specifically, phase transitions of the hydrocarbon-based analyte in the SPR sensing zone 123 can cause molecules to deposit onto (or evaporate from) the precipitate from the metallic film 121, causing an increase (or decrease) in the real component of the permittivity $\varepsilon_d(T)$ of the hydrocarbon-based analyte in the SPR sensing zone 123. This can lead to an abrupt decrease (or increase) in the surface plasmon resonance angle for this configuration. By sweeping the incidence angle $\theta_{i2}$, the reflected beam intensity, I, exhibits a characteristic angular-dependent profile. Because this profile is sensitive to environmental conditions in the SPR sensing zone 123, real-time changes in the permittivity of the analyte can be monitored by changes or shifts in the angular-dependent profile of the reflected beam intensity I.

A sample cell 350 is fixed in position relative to the prism 120 and the metallic film 121 and optical substrate 122 of the sensor head 100 as part of an assembly shown schematically in FIG. 1. This assembly is part of the thermally-controlled block 300 described in more detail below with the respect to FIGS. 3-5. The sample cell 350 defines a fixed-volume sample chamber 150 that is adjacent the metallic film 121. In this configuration, part of the fixed-volume sample chamber 150 lies in the SPR sensing zone 123 adjacent the metallic film 121. Note that other two faces of the prism 120 are unblocked to allow the monochromatic light beam to enter the prim 120 and exit the prism 120 after reflection at the interface of the metallic film 121 as shown in FIG. 1.

The thermally-controlled block 300 also includes two thermal stacks 325 (FIGS. 3 and 4) that sandwich the sample cell and prism assembly and operate to control the temperature of the sample cell 350 and the prism 120. Each thermal stack 325 includes a heat exchanger 320, a Peltier thermal-electric element 315 and heat sink 317. Temperature control of the heat exchangers 320 is provided by a thermal controller 331 (FIG. 2). The thermal controller 331 and the Peltier thermal-electric elements 315 can interface to a computer processing system 250 for use in controlling the temperature of the sample cell 350 and prism 120 of the thermally-controlled block 300 during operation of the SPR sensor (including as the platform/assembly rotates as described herein). The thermally-controlled block 300 can also include a temperature sensor (such as a thermocouple or other temperature sensor, which can be integrated into the sample cell 350) that can interface to the computer processing system 250 for use in monitoring and controlling the temperature of the sample cell 350 and prism 120 of the thermally-controlled block 300 during operation of the SPR sensor.

The thermally-controlled block 300 can be mounted on a rotatable platform (not shown) which is secured on top of a high-precision motorized rotation stage 332. The motorized operation of the rotation stage 332 is controlled by the computer processing system 250 to provide for controlled rotation of the platform/thermally-controlled block 300 in order to vary the angle of incidence Oil of the monochromatic light beam relative to the input face of the prism 120, which results in corresponding variation in the angle of incidence $\theta_{i2}$ of the monochromatic light beam relative to the metallic film 122. In some embodiments, the rotational axis of the platform/thermally-controlled block 300 is selected such that it is aligned (or nearly aligned) with the location of incidence of the monochromatic light beam relative to the interface of the metallic film 122. The photodetector 130 can be mounted to a platform (not shown) which is secured to a motorized linear motion stage 335. The motorized operation of the linear motion stage 335 is controlled by the computer processing system 250 such that as the thermally-controlled block 300 rotates, the photodetector 130 is moved along a trajectory that maintains alignment of the photodetector 130 with the center of the reflected light beam that is output from the output face of the prism 120, which is sensitive to the surface plasmon resonance at the metallic film 121. The electrical signal output of the photodetector 130 represents the intensity of the reflected light beam that is output from the output face of the prism 120 as the platform/thermally-controlled block 300 rotates. The electrical signal output of the photodetector 130 can be processed by signal processing circuitry (such as the lock-in amplifier 135 and analog-to-digital converter) such that the computer processing system 250 generates and stores digital data that represents the intensity of the reflected light beam that is output from the output face of the prism 120 as the platform/thermally-controlled block 300 rotates. This allows for rapid, automated, and robust acquisition of reflection measurements, which may be a useful capability, especially where there is difficulty in maintaining thermal equilibrium of the sample cell 350 over long periods. The rotational movement of the rotational motion stage 332 and the linear movement of the linear motion stage 335 are controlled through a motor driver 210 to supply power and read the positions of the respective stages (see FIG. 2). The computer processing system 250 can host a software application to communicate with and control the components of the SPR sensor during it operation. The software application can create a log of the reflected beam intensity data versus the angular position of the prism 120.

Figure 3:
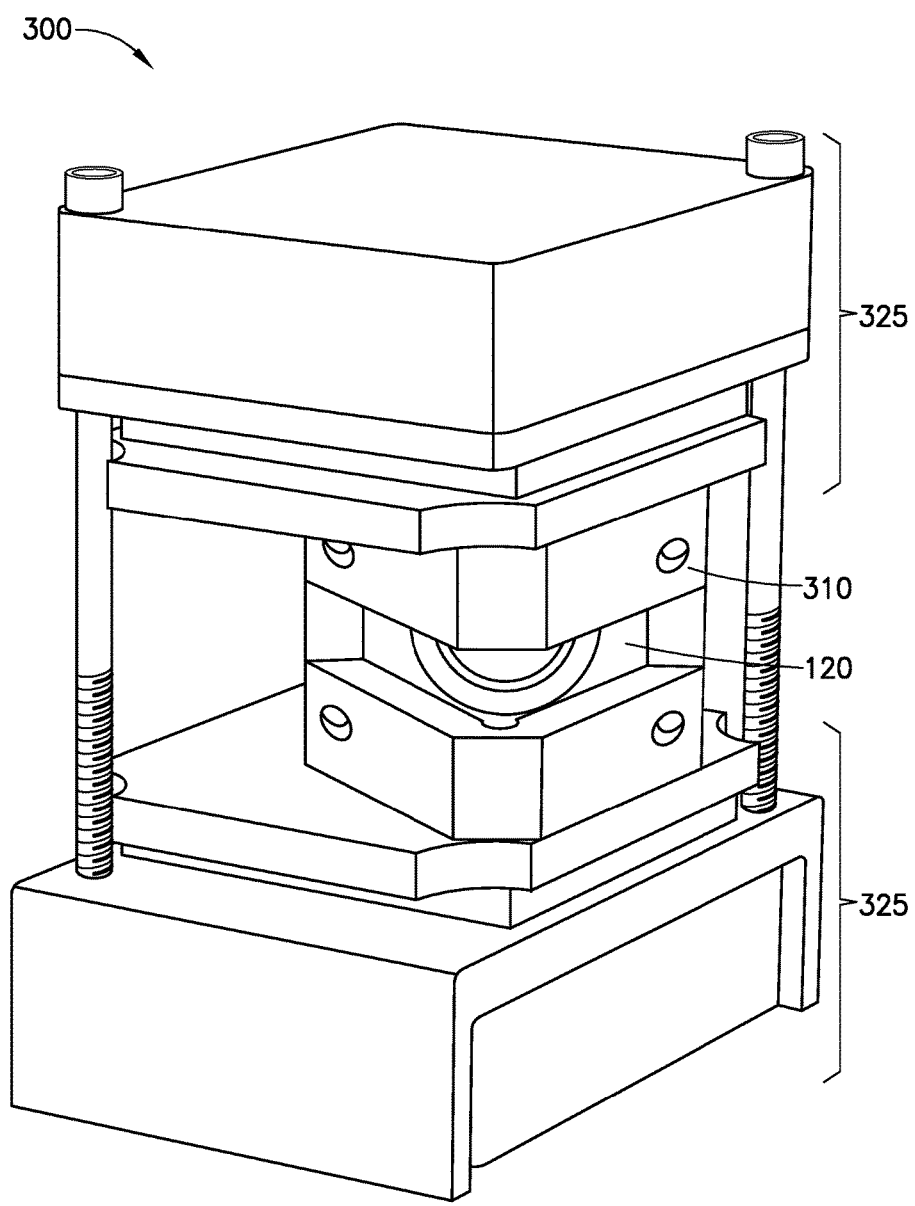
FIG. 3 is a perspective view of a thermally-controlled block (in its assembled state), which is a component of the first embodiment SPR sensor of FIGS. 1 and 2.
Figure 4:
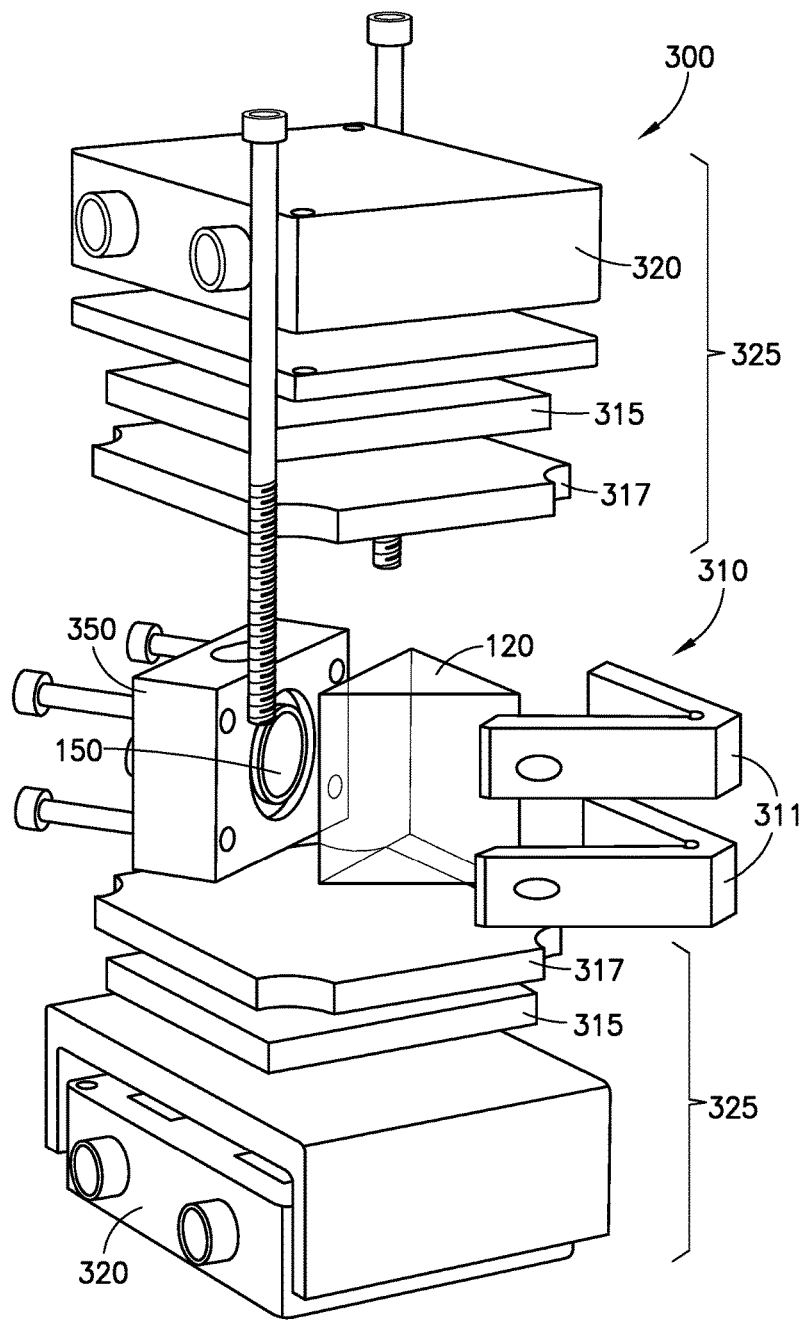
FIG. 4 is an exploded view of the thermally-controlled block of FIG. 3.
Figure 5:
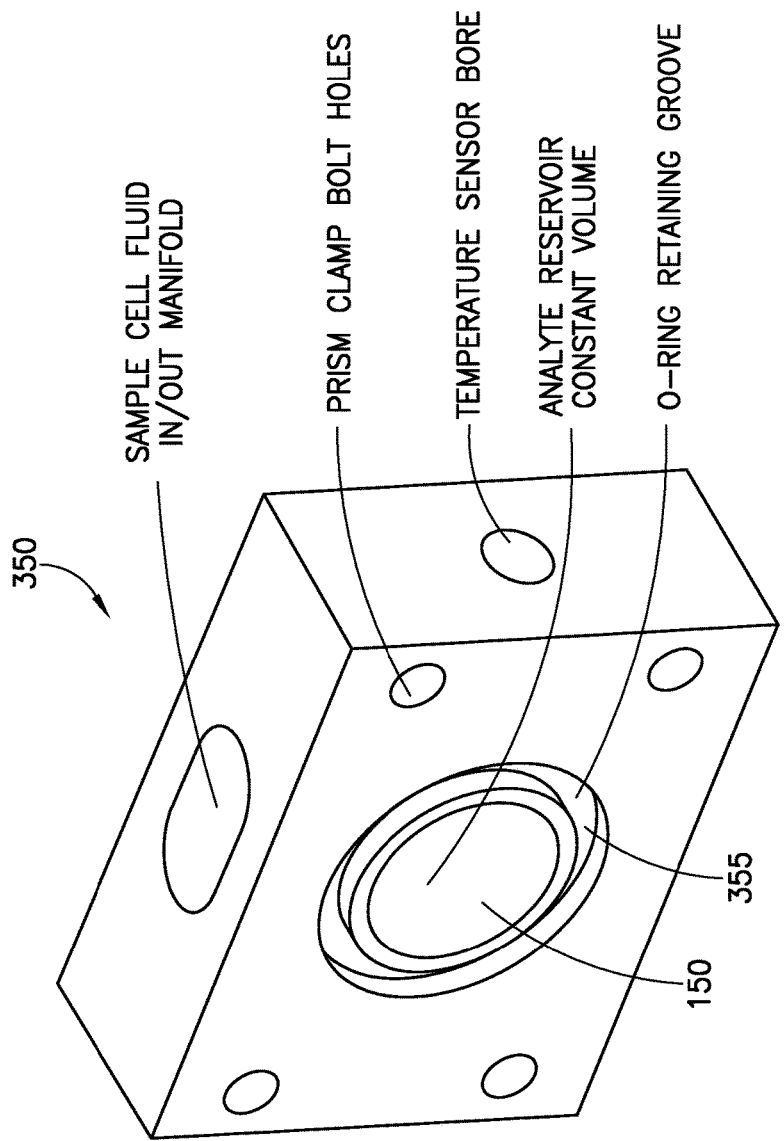
FIG. 5 is a perspective view of a sample cell, which is part of the thermally-controlled block of FIGS. 4 and 5.

FIGS. 3, 4 and 5 shows details of the thermally-controlled block 300 of the SPR sensor, which includes the sample cell 350 fixed to the metallic film 121/prism 120 by prism clamps 311. As best shown in FIG. 5, the sample cell 350 has a recessed cavity in the center, which defines the sample chamber 150 that houses the hydrocarbon-based analyte to be tested. The sample cell 350 is sealed against the metallic film 121 by an O-ring that is held in an O-ring retaining groove 355. The prism clamps 311 function to sandwich the metallic film 121 and substrate 120 in position between the sample cell 350 and the prism 120 to hold the assembly together. Note that the other two faces of the prism 120 are unblocked to allow the laser beam to enter the prism 120 and exit the prism 120 after reflection at the interface of the metallic film 121 (FIG. 1). Thermal control of the sample cell 350 and prism 120 is achieved by Peltier thermal-electric elements 315, each installed between a respective metal plate 317 (heat sink) and a heat exchanger 320, forming an assembly called the thermal stack 325. The thermal stacks 325 are mounted on the top and bottom of the sample cell 350/prism 120 assembly, creating a 3-layer assembly with the sample cell/prism assembly in the middle with one thermal stack 325 on each side. A small bore inside the sample cell 350 houses a temperature sensor (e.g., a Laird TC-NTC-1 thermistor), which for the present non-limiting example is sensitive to within 0.01° C. and operates over the range −30° C. to +90° C., for feedback control of the temperature of the sample cell 350, for example through a PID temperature control loop. In some embodiments, the thermal stacks 315 can maintain the temperature of sample cell 350 and prism 120 at a nominal temperature set point within an accuracy of 0.2° C. Insulation may be placed around the sample cell/prism assembly to increase thermal stability. In embodiments, a pump and inlet valve (similar to syringe pump 159 and inlet valve 160 of FIG. 20) can be used to convey the hydrocarbon-based analyte from a sample reservoir (similar to fluid source 158 of FIG. 20) to the sample chamber 150. Pressure control can be established by using the pump to maintain the sample chamber 150 at a set pressure monitored by a pressure transducer 157.

Figure 6:
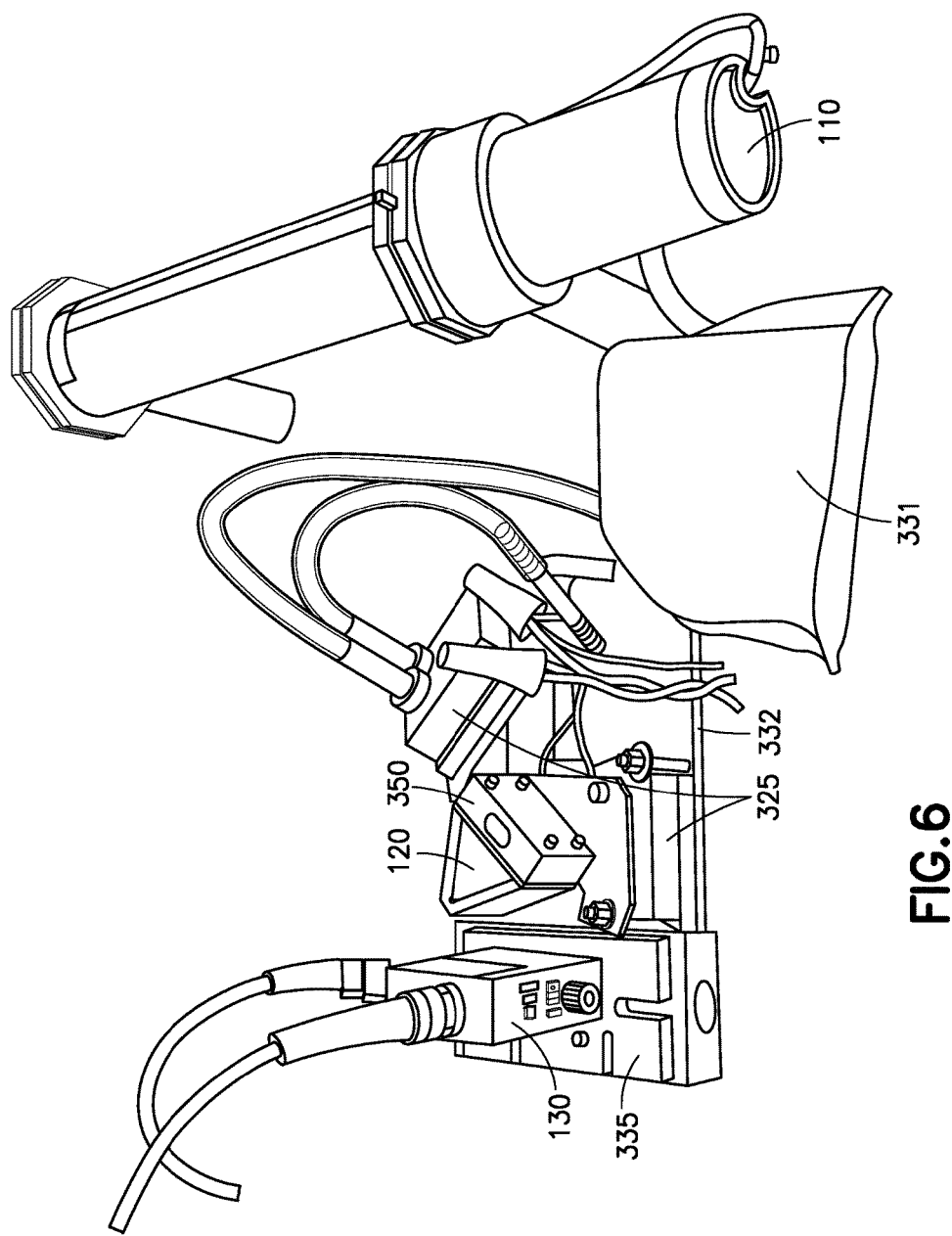
FIG. 6 is an image of the first embodiment SPR sensor of FIGS. 1 and 2.

The major components of the SPR sensor of FIGS. 1 and 2 is shown in FIG. 6.

The SPR sensor can be used to measure temperature and/or pressure conditions that correspond to a phase transition in a hydrocarbon-based analyte through experiments under constant pressure conditions where the temperature of the hydrocarbon-based analyte is controllably varied over a range of set point temperatures. An example of such phase transition measurement is wax appearance temperature (WAT) for a sample of crude oil or other reservoir fluid. In this case, the hydrocarbon-based analyte can be loaded into the fixed-volume sample chamber 150 of the SPR sensor at a set pressure. Pressure control of the hydrocarbon-based analyte can be established using one or more pressure control elements that control the pressure of the hydrocarbon-based analyte in the sample chamber 150 to a set pressure as monitored by the pressure transducer 157. Such pressure control element(s) can include a pump (e.g., syringe pump) and possibly one or more isolation valves (e.g., an inlet valve and/or exhaust valve) that are in fluid communication with the fixed-volume sample chamber 150 of the SPR sensor. With the hydrocarbon-based analyte at the controlled set pressure in the sample chamber 150, the computer processing system 250 can be configured to perform a sequence of test measurements over a range of set point temperatures. In each test measurement of the sequence, the computer processing system can be configured to perform a number of operations, including:

i) the computer processing system 250 interfaces to the temperature control elements (e.g., the thermal controller 331 and Peltier thermal-electric elements 315 of the thermally controlled block 300) of the SPR sensor to control the temperature of the sample cell 350 and prism 120 at the desired set point temperature of the specific test measurement as monitored by the temperature sensor 156; the computer processing system 250 can be configured to allow the temperature of the hydrocarbon-based analyte, the sample cell 350 and prism 120 to reach steady state at the set point temperature prior to acquiring the intensity measurements of the reflected light beam during controlled rotation of the platform/thermally controlled block 300 as described in ii)-iv) below;

ii) the computer processing system 250 controls the operation of the rotation stage 332 to provide for controlled rotation of the platform/thermally controlled block 300 over a predefined rotational range in order to vary the angle of incidence of the monochromatic light supplied by the monochromatic light source 110 relative to the input face of the prism 120, which varies the angle of incidence of the monochromatic light beam relative to the metallic film 121 of the SPR sensor;

iii) during such rotation, the computer processing system 250 controls the operation of the linear motion stage 335 such that the photodetector 130 is moved along a trajectory that maintains alignment of the photodetector 130 with the center of the reflected light beam that is output from the prism 120 (which is sensitive to the surface plasmon resonance at the interface of the metallic film 121 of the SPR sensor); and iv) during such rotation, the computer processing system 250 processes the electrical signals output by the photodetector 130 and signal processing circuitry (e.g., lock-in amplifier 135) in order to generate and store a record of intensity data as a function of angular position of the platform/thermally controlled block 300; the intensity data stored in the record represents the intensity of the reflected light beam that is output from the prism at respective angular positions of the platform/thermally controlled block 300 as the platform/thermally controlled block 300 rotates.

The hydrocarbon-based analyte can be loaded into the sample chamber 150 of the sample cell 350 by a pump (such as the pressure control syringe pump) and inlet valve. When the test measurements of the sequence are complete, the hydrocarbon-based analyte can be removed from the sample chamber 150 of the sample cell 350 through an exhaust valve and/or waste line.

The record of intensity data as a function of angular position of the platform/thermally controlled block 300 as stored by the computer processing system 250 for the sequence of test measurements can be evaluated and/or processed in order to determine at least one property relating to phase change of the hydrocarbon-based analyte.

In some embodiments, the at least one property relating to phase change of the hydrocarbon-based analyte can detected from i) the set point temperature corresponding to a local minima or dip in the intensity data as a function of the angular position of the thermally controlled block 300 (prism); ii) the set point temperature corresponding to an abrupt change in shape or slope of a local minima or dip in the intensity data as a function of the angular position of the thermally controlled block 300 (prism); iii) the set point temperature corresponding to an abrupt change in the minimum of the intensity data over the angular positions of the thermally controlled block 300 (prism) as a function of set point temperature; iv) the set point temperature corresponding to an abrupt change in the intensity data at a plurality of angular positions of the thermally controlled block 300 (prism) as a function of set point temperature; v) the set point temperature corresponding to an abrupt change in the angle of minimum intensity data over the angular positions of the thermally controlled block 300 (prism) as a function of set point temperature; and vi) the set point temperature corresponding to other signal metrics derived from the intensity data as a function of the angular position of the thermally-controlled block 300 (prism) as a function of set point temperature.

In other experiments, the SPR sensor of FIGS. 1 and 2 can be used to measure temperature and/or pressure conditions that correspond to a phase transition in a hydrocarbon-based analyte through experiments under constant temperature conditions where the pressure of the hydrocarbon-based analyte is controllably varied over a range of set point pressures. An example of such phase transition measurement is asphaltene onset pressure (where asphaltenes precipitate and form a solid film) for a sample of crude oil. In this case, the temperature of the hydrocarbon-based analyte, the sample cell 150 and prism 120 of the SPR sensor can be controlled to a desired set temperature. Temperature control can be established by using the temperature control elements (e.g., the thermal controller 331 and Peltier thermal-electric elements 315 of the thermally controlled block 300) of the SPR sensor to control the temperature of the sample cell 350 and prism 120 at the desired set temperature as monitored by the temperature sensor 156. With the hydrocarbon-based analyte in the fixed volume sample chamber 150 of the sample cell 350 at the controlled set temperature, the computer processing system 250 can be configured to perform a sequence of test measurements over a range of set point pressures. In each test measurement of the sequence, the computer processing system can be configured to perform a number of operations, including:

i) the computer processing system 250 interfaces to one or more pressure control elements that controls the pressure of the hydrocarbon-based analyte in the sample chamber 150 at the set point pressure of the respective test measurement as monitored by the pressure transducer 157; such pressure control element(s) can include a pump (e.g., syringe pump) and possibly one or more isolation valves (e.g., an inlet valve and/or exhaust valve) that are in fluid communication with the fixed-volume sample chamber 150 of the SPR sensor; the computer processing system 250 can be configured to allow the pressure of the hydrocarbon-based analyte in the sample chamber 150 to reach steady state at the set point pressure prior to acquiring the intensity measurements of the reflected light beam during controlled rotation of the platform/thermally-controlled block 300 as described in ii)-iv) below;

ii) the computer processing system 250 controls the operation of the rotation stage to provide for controlled rotation of the platform/thermally-controlled block 300 over a predefined rotational range in order to vary the angle of incidence of the monochromatic light supplied by the monochromatic light source 110 relative to the input face of the prism 120, which varies the angle of incidence of the monochromatic light beam relative to the metallic film 121 of the SPR sensor;

iii) during such rotation, the computer processing system 250 controls the operation of the linear motion stage 335 such that the photodetector 130 is moved along a trajectory that maintains alignment of the photodetector 120 with the center of the reflected light beam that is output from the prism 120 (which is sensitive to the surface plasmon resonance at the interface of the metallic film 121 of the SPR sensor); and iv) during such rotation, the computer processing system 250 processes the electrical signals output by the photodetector 130 and signal processing circuitry (e.g., lock-in amplifier) in order to generate and store a record of intensity data as a function of angular position of the platform/thermally-controlled block 300; the intensity data stored in the record represents the intensity of the reflected light beam that is output from the prism at respective angular positions of the platform/thermally-controlled block 300 as the platform/thermally-controlled block 300 rotates.

In embodiments, the hydrocarbon-based analyte can be loaded into the sample chamber 150 of the sample cell 350 by a pump (such as the pressure control syringe pump) and inlet valve. When the test measurements of the sequence are complete, the hydrocarbon-based analyte can be removed from the sample chamber 150 of the sample cell 350 through an exhaust valve and/or waste line.

The record of intensity data as a function of angular position of the platform/thermally-controlled block 300 as stored by the computer processing system for the sequence of test measurements can be evaluated and/or processed in order to determine at least one property relating to phase change of the hydrocarbon-based analyte.

In some embodiments, the at least one property relating to phase change of the hydrocarbon-based analyte can detected from i) the set point pressure corresponding to a local minima or dip in the intensity data as a function of the angular position of the thermally-controlled block 300 (prism); ii) the set point pressure corresponding to an abrupt change in shape or slope of a local minima or dip in the intensity data as a function of the angular position of the thermally controlled block 300 (prism); iii) the set point pressure corresponding to an abrupt change in the minimum of the intensity data over the angular positions of the thermally-controlled block 300 (prism) as a function of set point pressure; iv) the set point pressure corresponding to an abrupt change in the intensity data for a plurality of angular positions of the thermally-controlled block 300 (prism) as a function of set point pressure; v) the set point pressure corresponding to an abrupt change in the angle of minimum intensity data over the angular positions of the thermally-controlled block 300 (prism) as a function of set point pressure; and vi) the set point pressure corresponding to other signal metrics derived from the intensity data as a function of the angular position of the thermally-controlled block 300 (prism) as a function of set point pressure.

In still other experiments, the SPR sensor of FIGS. 1 and 2 can be used to measure temperature and pressure conditions that induce phase transitions in a hydrocarbon-based analyte through experiments with controlled variations in both the temperature and pressure conditions of the hydrocarbon-based analyte. Examples of such phase transition measurements is bubble point, dew point and other phase transitions in a sample of crude oil, condensate gas or other reservoir fluid. In this case, the temperature of the hydrocarbon-based analyte, the sample cell 350 and prism 120 of the SPR sensor can be controlled to a desired set temperature above the phase transition temperature—typically the sample's reservoir temperature. Temperature control can be established by using temperature control elements (e.g., the thermal controller 331 and Peltier thermal-electric elements 315 of the thermally controlled block 300) of the SPR sensor to control the temperature of the sample cell 350 and prism 120 at the desired set temperature as monitored by the temperature sensor 156. With the hydrocarbon-based analyte in the fixed volume sample chamber 150 of the sample cell 350 at the controlled set temperature, the computer processing system 250 can be configured to perform a sequence of test measurements over a range of set point pressures (referred to as a "pressure loop"). In each test measurement of the pressure loop, the computer processing system can be configured to perform a number of operations, including:

i) the computer processing system 250 interfaces to one or more pressure control elements that controls the pressure of the hydrocarbon-based analyte in the sample chamber 150 at the set point pressure of the respective test measurement as monitored by a pressure transducer 157; such pressure control element(s) can include a pump (e.g., syringe pump) and possibly one or more isolation valves (e.g., an inlet valve and/or exhaust valve) that are in fluid communication with the fixed-volume sample chamber 150 of the SPR sensor; the computer processing system 250 can be configured to allow the pressure of the hydrocarbon-based analyte in the sample chamber 150 to reach steady state at the set point pressure prior to acquiring the intensity measurements of the reflected light beam during controlled rotation of the platform/assembly as described in ii)-iv) below;

ii) the computer processing system 250 controls the operation of the rotation stage 332 to provide for controlled rotation of the platform/thermally-controlled block 300 over a predefined rotational range in order to vary the angle of incidence of the monochromatic light supplied by the monochromatic light source 110 relative to the input face of the prism 120, which varies the angle of incidence of the monochromatic light beam relative to the metallic film 121 of the SPR sensor;

iii) during such rotation, the computer processing system 250 controls the operation of the linear motion stage 335 such that the photodetector 130 is moved along a trajectory that maintains alignment of the photodetector 130 with the center of the reflected light beam that is output from the prism 10 (which is sensitive to the surface plasmon resonance at the interface of the metallic film 121 of the SPR sensor); and iv) during such rotation, the computer processing system 250 processes the electrical signals output by the photodetector 130 and signal processing circuitry (e.g., lock-in amplifier 135) in order to generate and store a record of intensity data as a function of angular position of the platform/thermally-controlled block 300; the intensity data stored in the record represents the intensity of the reflected light beam that is output from the prism 120 at respective angular positions of the platform/thermally-controlled block 300 as the platform/thermally-controlled block 300 rotates.

After the pressure loop is fully executed (or a phase transition has been detected), the computer processing system 250 can be configured to control the pressure of the hydrocarbon-based analyte in the sample chamber 150 such that such pressure returns to reservoir pressure. If necessary, the computer processing system 250 can control temperature of the sample cell 250 and prism 120 by decrementing such temperature by a set amount, and the pressure loop is executed again. The temperature parent loop (along with the children pressure loops) can be executed until a lower temperature limit is reached. The pressure loops and temperature loops can be executed independently or in a nested manner as required by the type of phase transition targeted.

In embodiments, the hydrocarbon-based analyte can be loaded into the sample chamber 150 of the sample cell 350 by a pump (such as the pressure control syringe pump) and inlet valve. When the pressure loops and temperature loops are complete, the hydrocarbon-based analyte can be removed from the sample chamber 150 of the sample cell 350 through an exhaust valve and/or waste line.

The record of intensity data as a function of angular position of the platform/thermally-controlled block 300 as stored by the computer processing system over the test measurements of the pressure loops and temperature loops can be evaluated and/or processed in order to determine at least one property relating phase change of the hydrocarbon-based analyte.

In some embodiments, the at least one property relating to phase change of the hydrocarbon-based analyte can detected from i) temperature and pressure conditions corresponding to a local minima or dip in the intensity data as a function of the angular position of the thermally-controlled block 300 (prism) for a particular controlled temperature and pressure; ii) temperature and pressure conditions corresponding to an abrupt change in shape or slope of a local minima or dip in the intensity data as a function of the angular position of the thermally controlled block 300 (prism); iii) temperature and pressure conditions corresponding to an abrupt change in the minimum of the intensity data over the angular positions of the thermally-controlled block 300 (prism) as a function of set point pressure at a particular controlled temperature; iv) temperature and pressure conditions corresponding to an abrupt change in the intensity data for a plurality of angular positions of the thermally-controlled block 300 (prism) as a function of set point pressure at a particular controlled temperature; v) temperature and pressure conditions corresponding to an abrupt change in the angle of minimum intensity data over the angular positions of the thermally-controlled block 300 (prism) as a function of set point pressure at a particular controlled temperature; and vi) temperature and pressure conditions corresponding to other signal metrics derived from the intensity data as a function of the angular position of the thermally-controlled block 300 (prism) as a function of set point pressure at a particular controlled temperature.

Figure 7:
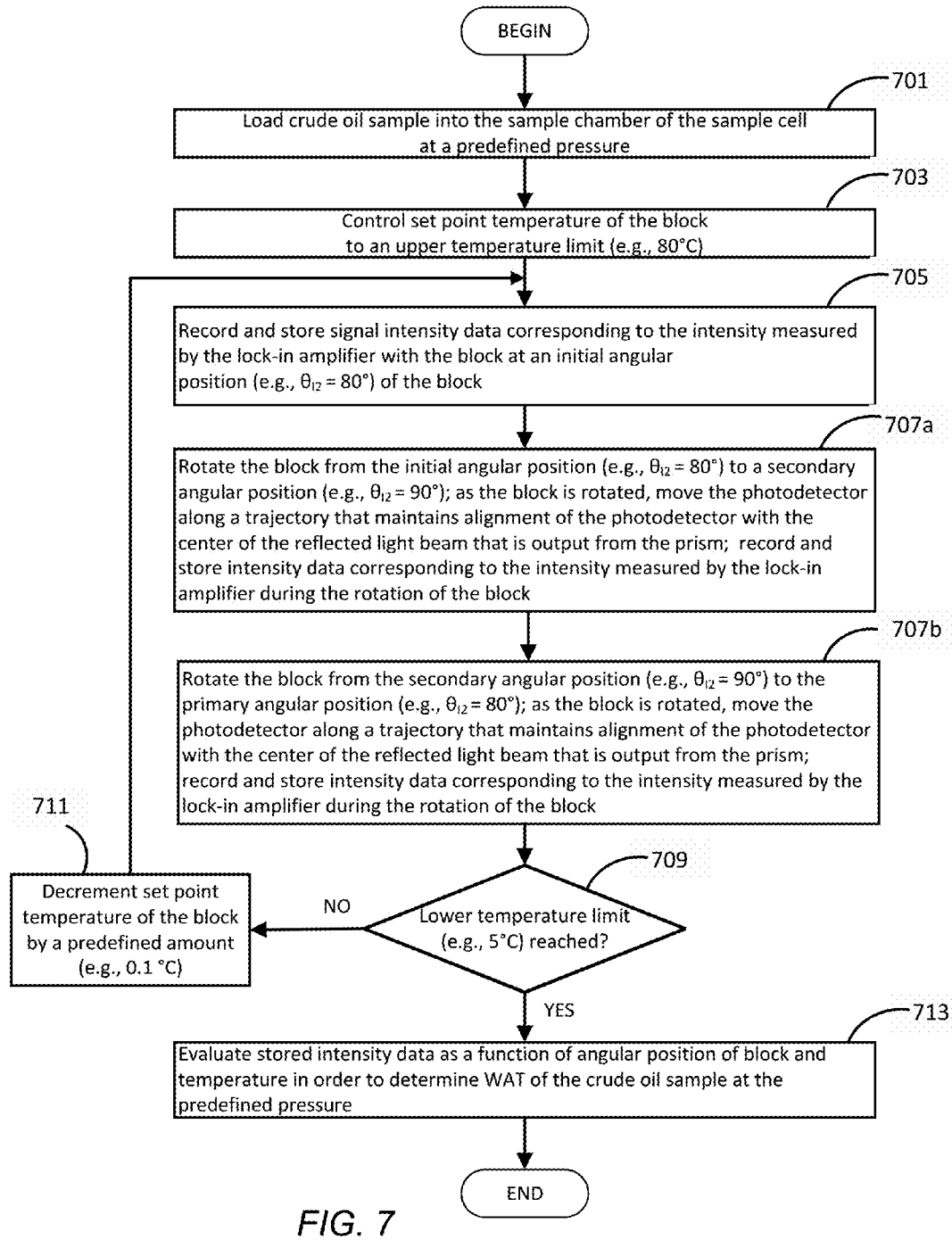
FIG. 7 is a flow chart illustrating an exemplary workflow that uses the SPR sensor of FIGS. 1 and 2 to determine WAT of a crude oil sample.

FIG. 7 illustrates an exemplary workflow that uses the SPR sensor of FIGS. 1 and 2 to determine wax appearance temperature (WAT) of a crude oil sample.

At 701, the crude oil sample (~1 ml) is loaded into the sample chamber 150 of the sample cell 350 and the system is assembled, if need be, and activated.

At 703, the computer processing system 250 interfaces to the thermal controller 331 and the Peltier thermal-electric elements 315 of the thermally-controlled block 300 to control the temperature of the sample cell 350 and prism 120 at an upper temperature limit (e.g., 80° C.). The upper temperature limit can be selected such that is well above the expected wax appearance temperature (WAT) of a crude oil sample. The computer processing system 250 can employ a PID control loop to control the temperature of the sample cell 350 and prism 120, where the temperature feedback signal is measured inside the sample cell 350. The PID control loop can be configured to allow the temperature of the sample cell 350 and prism 120 to stabilize for a thermal equilibrium time, $\tau$, before proceeding to the optical measurements (the first iteration of 705). The thermal equilibrium time is the time required for the sample cell (and therefore, the crude oil sample) to reach the set temperature of the thermal stack. It corresponds to the settling time of the PID control loop. Nominally, the thermal equilibrium time is estimated to be about 2 minutes, based on the average time taken for the temperature of the sample cell 350 to cool by 1° C. after decreasing the set temperature of the thermal stack by 1° C.

At 705, the computer processing system 250 is configured to record and store intensity data corresponding to the intensity measured by the lock-in amplifier 135 with the thermally-controlled block 300 (prism) at an initial angular position (e.g., where $\theta_{r2}=80°$).

At 707a, the computer processing system 250 controls rotational movement of the thermally-controlled block 300 (prism) from the initial angular position (e.g., where $\theta_{r2}=80°$) to a secondary angular position (e.g., where $\theta_{r2}=90°$). As the thermally-controlled block 300 (prism) is rotated, the computer processing system 250 controls linear movement of the photodetector 130 along a trajectory that maintains alignment of the photodetector 130 with the center of the reflected light beam that is output from the prism. The computer processing system 250 is also configured to store a record of intensity data as a function of angular position of the thermally-controlled block 300. The intensity data of the record represents the intensity measured by the lock-in amplifier 135 at respective angular positions of the thermally-controlled block 300 during the rotational movement of the thermally-controlled block 300.

At 707b, the computer processing system 250 controls rotational movement of the thermally-controlled block 300 (prism) from the secondary angular position (e.g., where $\theta_{r2}=90°$) to the initial angular position (e.g., where $\theta_{r2}=80°$). As the thermally-controlled block 300 (prism) is rotated, the computer processing system 250 controls linear movement of the photodetector 130 along a trajectory that maintains alignment of the photodetector 130 with the center of the reflected light beam that is output from the prism. The computer processing system 250 is also configured to store a record of intensity data as a function of angular position of the thermally-controlled block 300. The intensity data of the record represents the intensity measured by the lock-in amplifier 135 at respective angular positions of the thermally-controlled block 300 during the rotational movement of the thermally-controlled block 300.

At 709, the computer processing system 250 determines whether the set point temperature has reached a lower temperature limit (e.g., 5° C.). If so, the operations continue to 713 as described below. If not, the operations continue to 711 where the computer processing system 250 decrements the set point temperature of the thermally-controlled block 300 by a predefined amount (e.g., 0.1° C.), and the operations continue to repeat the operations of 705 to 709. In block 711, the PID control can be configured to allow the temperature of the sample cell 350 and prism 120 to stabilize for a thermal equilibrium time, τ, before proceeding to the optical measurements of blocks 705, 707a and 707b.

At 713, the intensity data as a function of angular position of the thermally-controlled block 300 stored by the computer processing system 250 over the iterations of 705, 707a and 707b is evaluated to determine the WAT of the crude oil sample at the predefined pressure. As part of such evaluation, the computer processing system 250 can calculate a nominal SPR intensity values over the angular positions of the thermally-controlled block 300 by averaging the two measurements of blocks 707a and 707b that correspond to the same angular position of the thermally-controlled block 300. The nominal SPR intensity values can be plotted and evaluated manually or processed automatically by the computer processing system 250 to determine the WAT of the crude oil sample at the predefined pressure. WAT can be detected from i) the set point temperature corresponding to a local minima or dip in the intensity data as a function of the angular position of the thermally-controlled block 300 (prism); ii) the set point temperature corresponding to an abrupt change in shape or slope of a local minima or dip in the intensity data as a function of the angular position of the thermally controlled block 300 (prism); iii) the set point temperature corresponding to an abrupt change in the minimum of the intensity data over the angular positions of the thermally-controlled block 300 (prism) as a function of set point temperature; iv) the set point temperature corresponding to an abrupt change in the intensity data for a plurality of angular positions of the thermally-controlled block 300 (prism) as a function of set point temperature; v) the set point temperature corresponding to an abrupt change in the angle of minimum intensity data over the angular positions of the thermally-controlled block 300 (prism) as a function of set point temperature; and vi) the set point temperature corresponding to other signal metrics of the intensity data over the angular positions of the thermally-controlled block 300 (prism) as a function of set point temperature.

In order to validate the effectiveness of the SPR sensors as described herein, the workflow of FIG. 7 was performed to determine the WAT for a variety of hydrocarbon-based analytes whose WAT are known from literature.

Figure 8A:
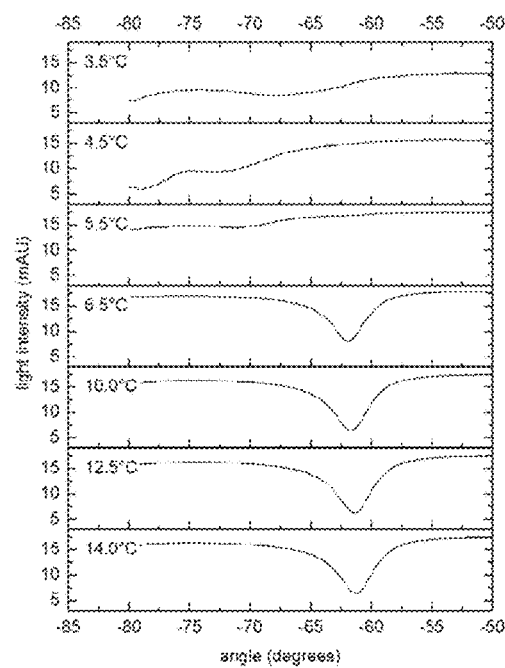
FIGS. 8A-8C are plots of data derived from the workflow of FIG. 7 in order to determine the WAT of tetradecane or C14.
Figure 8B:
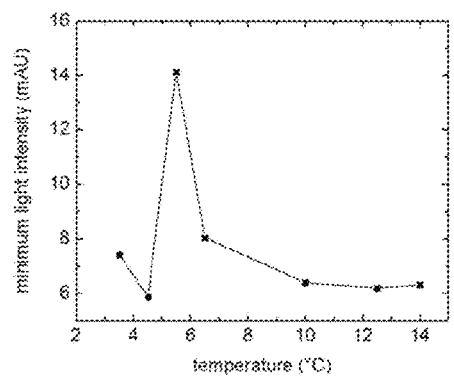
Figure 8C:
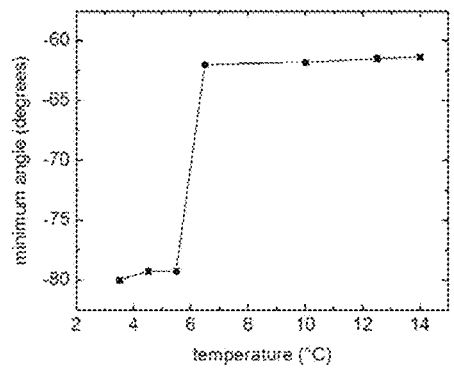

FIGS. 8A-8C are plots of data derived from the workflow of FIG. 7 in order to determine the WAT of tetradecane or C14, which has an accepted WAT of 6° C. from the literature. FIG. 8A includes plots of the nominal intensity data as function of angular position of the thermally-controlled block (prism) at various temperatures for a tetradecane (or C14) sample. The nominal intensity data is based on the light intensity output from the output face of the prism as detected by the photodetector and lock-in amplifier over the rotational movement of the thermally-controlled block (prism) at each one of the various temperatures. Note that at temperatures greater than 6° C., the nominal intensity data versus angular position of the thermally-controlled block (prism) shows a discernible peak minima (or dip or trough), as is commonly observed for typical SPR signals. As temperature decreases from 14° C. to 6° C., a slight downward shift is noted in the minimum peak angle—corresponding to an increase in density and an increase in permittivity. At 5.5° C., a steep drop in nominal intensity data near the SPR angle is noted, where it is difficult to distinguish a discernible peak minima (or dip or trough). At temperatures less than 6° C., the nominal intensity data shows a flattened profile with no discernible peak minima (or dip or trough). Note that intensity data detected by the photodetector and lock-in amplifier over the rotational movement of the thermally-controlled block (prism) at each one of the various temperatures can be plotted as minimum light intensity as a function of set point temperature as shown in FIG. 8B and as angular block position of minimum intensity over the angular positions of the thermally-controlled block (prism) as a function of set point temperature as shown in FIG. 8C. Both of these plots show a discernable abrupt change at the temperature of 6° C., which shows that WAT is clearly detected at the expected temperature of 6° C.

FIGS. 9A-9C are plots of data derived from the workflow of FIG. 7 in order to determine the WAT of hexadecane or C16, which has an accepted WAT of 18° C. from the literature. FIG. 9A includes plots of the nominal intensity data as function of angular position of the thermally-controlled block (prism) at various temperatures for a hexadecane (or C16) sample. At temperatures greater than 18° C., the nominal intensity data versus angular position of the thermally-controlled block (prism) shows a pronounced peak minima. Again, as temperature decreases from 35° C. to 18° C., a slight downward angular shift is noted in the minimum peak angle—corresponding to an increase in density and an increase in permittivity. At temperatures less than 18° C., the nominal intensity data as function of angular position of the thermally-controlled block shows a flattened profile with no discernable peak minima. Note that intensity data detected by the photodetector and lock-in amplifier over the rotational movement of the thermally-controlled block (prism) at each one of the various temperatures can be plotted as minimum light intensity as a function of set point temperature as shown in FIG. 9B and as angular block position of minimum intensity over the angular positions of the thermally-controlled block (prism) as a function of set point temperature as shown in FIG. 9C. Both of these plots show a discernable abrupt change at the temperature of 18° C., which shows that WAT is clearly detected at the expected temperature of 18° C.

FIGS. 10A-10C are plots of data derived from the workflow of FIG. 7 in order to determine the WAT of a mixture of tetradecane (C14) and hexadecane (C16). The mixture has 0.8 molar fraction C16 and 0.2 molar fraction C14, with an accepted WAT of approximately 15° C. FIG. 10A includes plots of the nominal intensity data as function of angular position of the thermally-controlled block (prism) at various temperatures for the mixture. It is not visually apparent from the nominal intensity data of FIG. 10A where the WAT occurs. Note that intensity data detected by the photodetector and lock-in amplifier at particular angular positions (e.g., −64.4°, −63.56°, −62.94°) of the thermally-controlled block (prism) at each one of the various temperatures can be plotted as a function of set point temperature as shown in FIG. 10B and as angular block position of minimum intensity over the angular positions of the thermally-controlled block (prism) as a function of set point temperature as shown in FIG. 10C. The plots of FIG. 10B show discernable abrupt changes at the temperature of 14° C., which shows that WAT is clearly detected at near the expected temperature of approximately 15° C. Note that in FIG. 10B the nominal intensity data at the particular angular positions (e.g., −64.4°, −63.56°, −62.94° decreases as temperature decreases from 23° C. to 15° C. Then, the nominal intensity data abruptly increases at 14° C. and resumes a gradual decrease. This abrupt change indicates a change in the reflected light intensity profile's shape and suggests sample on the SPR sensor surface has changed phases. There is also a notable increase in the rate of change in the minimum peak angle of FIG. 10C at 14° C., where the peak angle shift per unit temperature drop is higher.

Figure 11:
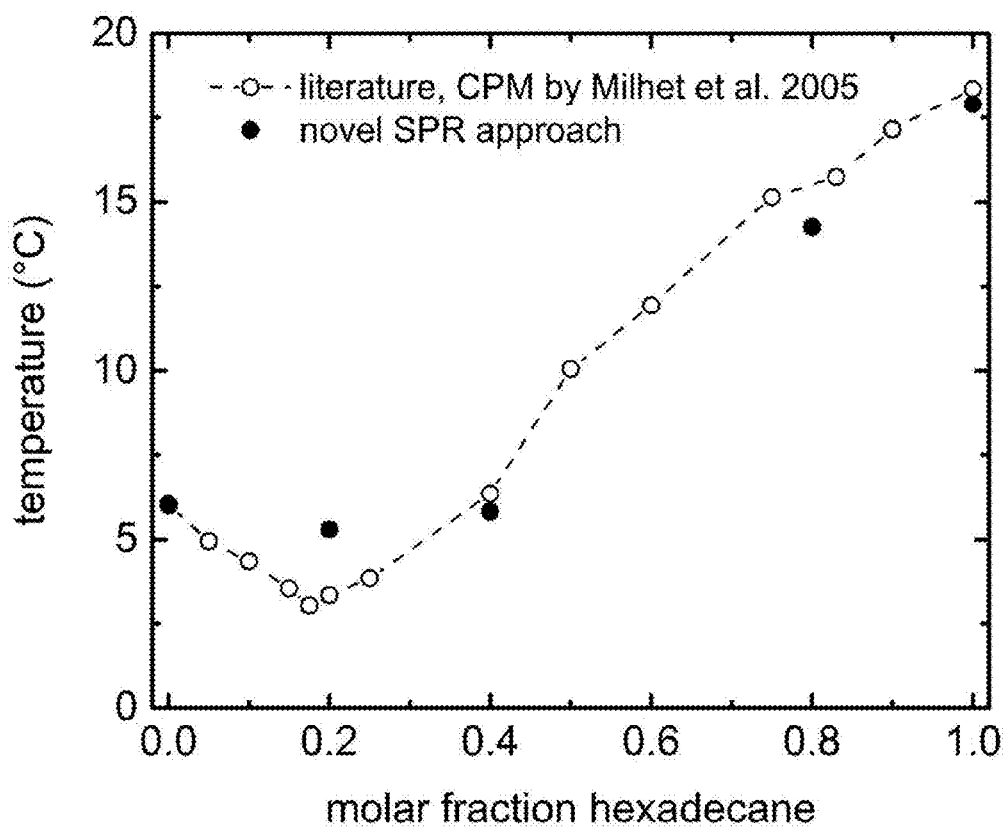
FIG. 11 is a liquidus curve for five binary mixtures of tetradecane (C14) and hexadecane (C16) at atmospheric pressure that is derived from the workflow of FIG. 7. At x=0, the WAT for pure tetradecane (C14) as derived from the workflow of FIG. 7 is 6° C., and at x=1 the WAT for pure hexadecane (C16) as derived from the workflow of FIG. 7 is 18° C. The dashed line with open circular data points shows accepted values from the literature. The solid circular data points are the WAT measurements for pure C14, pure C16, and three other binary mixtures (0.2 molar fraction C16 and 0.8 molar fraction C14, 0.4 molar fraction C16 and 0.6 molar fraction C14, and 0.8 molar fraction C16 and 0.2 molar fraction C14) as derived from the workflow of FIG. 7.

FIG. 11 is a liquidus curve for five binary mixtures of tetradecane (C14) and hexadecane (C16) at atmospheric pressure that is derived from the workflow of FIG. 7. At x=0, the WAT for pure tetradecane (C14) as derived from the workflow of FIG. 7 is 6° C., and at x=1 the WAT for pure hexadecane (C16) as derived from the workflow of FIG. 7 is 18° C. The dashed line with open circular data points shows accepted values from the literature. The solid circular data points are the WAT measurements for pure C14, pure C16, and three other binary mixtures (0.2 molar fraction C16 and 0.8 molar fraction C14, 0.4 molar fraction C16 and 0.6 molar fraction C14, and 0.8 molar fraction C16 and 0.2 molar fraction C14) as derived from the workflow of FIG. 7. The WATs match reasonably well between the two techniques, CPM from the literature and SPR described in the present disclosure.

Figure 13:
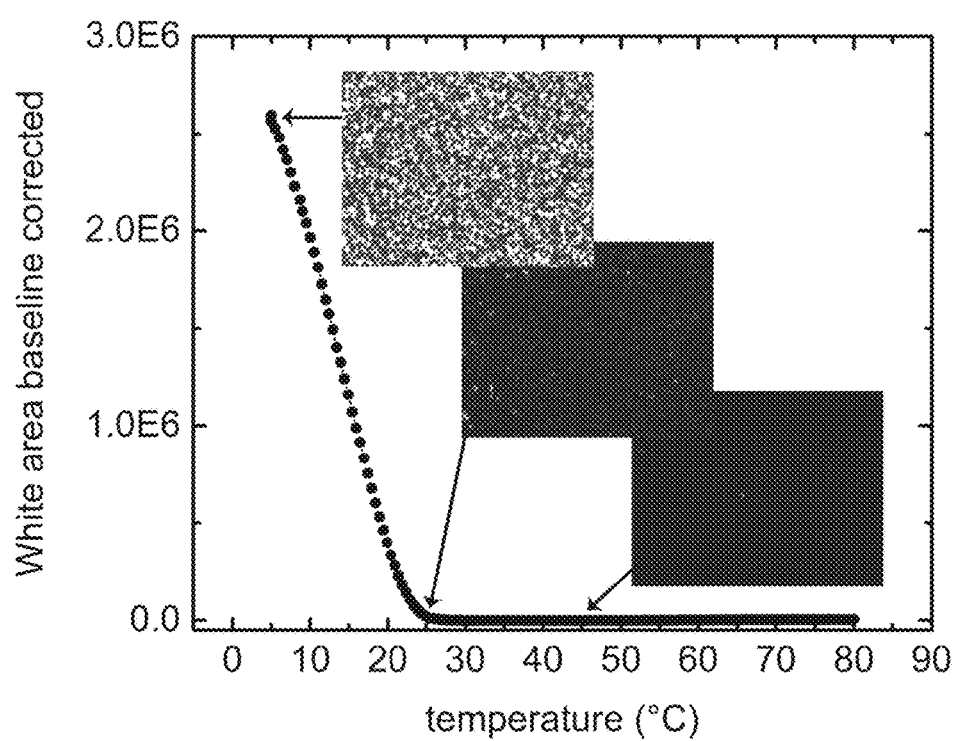
FIG. 13 are CPM images and data corresponding to the measurement of WAT for the crude oil sample 1 of FIGS. 12A-12C.

FIGS. 12A-12C are plots of data derived from the workflow of FIG. 7 in order to determine the WAT of a crude oil sample (referred to as "crude oil 1 sample"), with a measured WAT of 25° C. using CPM. The CPM images and data are shown in FIG. 13. FIG. 12A includes plots of the nominal intensity data as function of angular position of the thermally-controlled block (prism) at various temperatures for the crude oil 1 sample. Similar to the case of the binary mixtures of n-alkanes, it is not visually apparent from the nominal intensity data of FIG. 12A where the WAT occurs. Note that intensity data detected by the photodetector and lock-in amplifier over the angular positions of the thermally-controlled block (prism) at each one of the various temperatures can be plotted as angular block position of minimum intensity over the angular positions of the thermally-controlled block (prism) as a function of set point temperature as shown in FIG. 12B and as values of an SPR shape metric as a function of set point temperature as shown in FIG. 12C.

Note that careful examination of the SPR intensity data reveals that the shape or slope of the local minima or dip in the SPR intensity data as a function of angular position of the thermally-controlled block (prism) undergoes changes near the WAT. In order to quantify this change, an SPR shape metric can be empirically derived from the SPR intensity data as follows:

$$\Gamma = \int_{\theta_{spr}}^{\theta_{spr}+\Delta\theta} \left|\frac{dI}{d\theta}\right|^2 d\theta, \quad (2)$$

where $$\frac{dI}{d\theta}$$

is the derivative of the SPR intensity data and $\Delta\theta=3°$ C. is a small angular offset of the thermally-controlled block (prism) which samples the leading edge of the local minima or dip in the SPR intensity data. By referencing $\theta_{spr}$, this metric is insensitive to baseline shifts in the effective permittivity (refractive index) of the hydrocarbon-based analyte.

This SPR shape metric is plotted as a function of set point temperature in FIG. 12C. Note that plot of the SPR shape metric values versus temperature of FIG. 12C show discernable abrupt changes at the temperature of 27° C., which shows that WAT is clearly detected at near the expected temperature of approximately 25° C. Note that the plot of SPR minimum peak angle versus temperature of FIG. 12B for crude oil sample 1 shows only minor variation near the WAT.

Figures 14A, 14B, 14C:
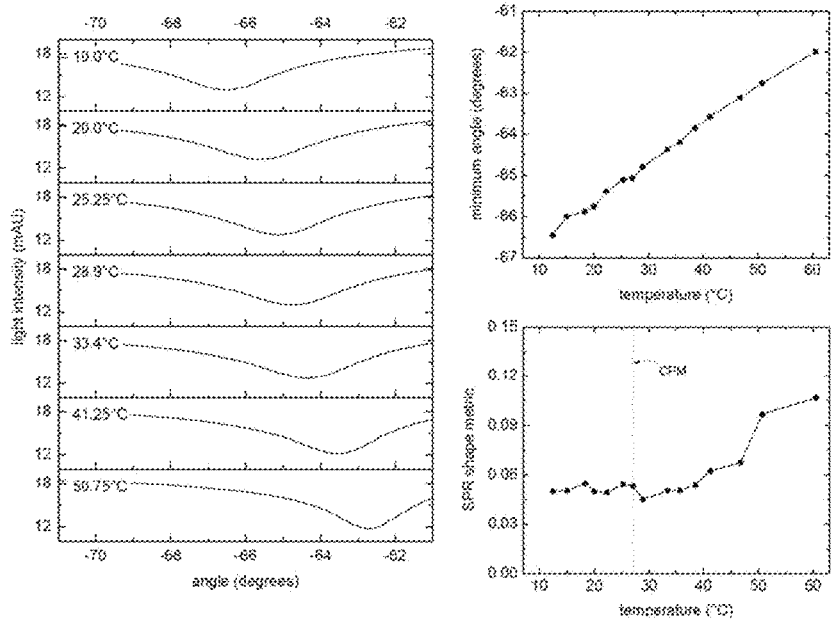
FIGS. 14A-14C are plots of data derived from the workflow of FIG. 7 in order to determine the WAT of a crude oil sample (referred to as "crude oil 2 sample").
Figure 15:
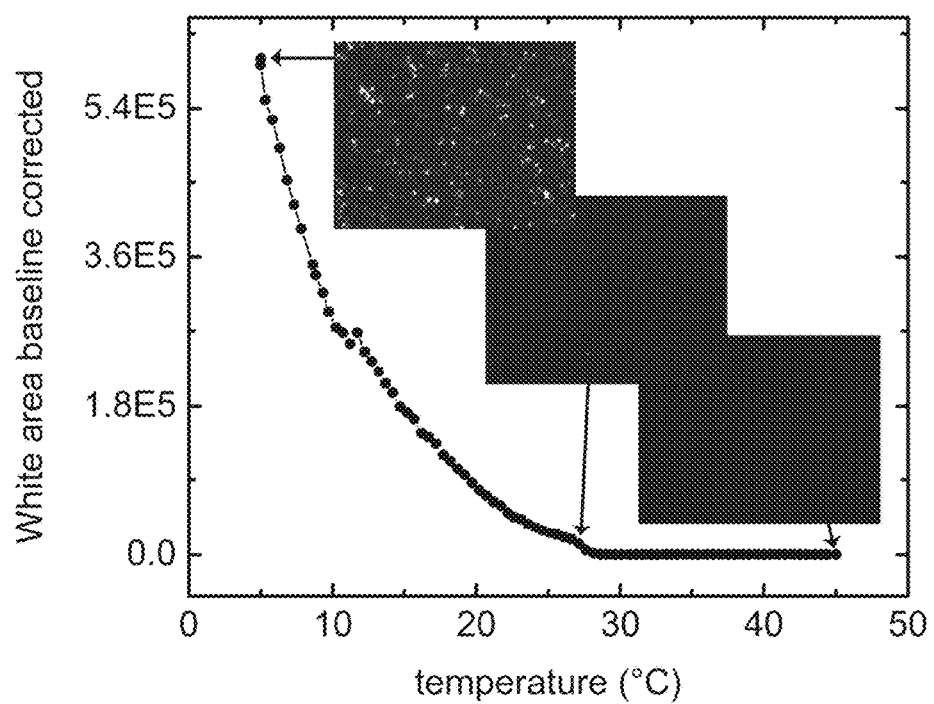
FIG. 15 are CPM images and data corresponding to the measurement of WAT for the crude oil sample 2 of FIGS. 14A-14C.

FIGS. 14A-14C are plots of data derived from the workflow of FIG. 7 in order to determine the WAT of a crude oil sample (referred to as "crude oil 2 sample"), with a measured WAT of 27° C. using CPM. The CPM images and data are shown in FIG. 15. FIG. 14A includes plots of the nominal intensity data as function of angular position of the thermally-controlled block (prism) at various temperatures for the crude oil 2 sample. Similar to the case of the binary mixtures of n-alkanes and the crude oil 1 sample, it is not visually apparent from the nominal intensity data of FIG. 14A where the WAT occurs. Note that intensity data detected by the photodetector and lock-in amplifier over the angular positions of the thermally-controlled block (prism) at each one of the various temperatures can be plotted as angular block position of minimum intensity over the angular positions of the thermally-controlled block (prism) as a function of set point temperature as shown in FIG. 14B and as values of the SPR shape metric of Eqn. (2) as a function of set point temperature as shown in FIG. 14C. The plot of the SPR shape metric values versus temperature of FIG. 14C show discernable abrupt changes at the temperature of 27° C., which shows that WAT can be detected at near the expected temperature of approximately 27° C. Note that the SPR minimum peak angle versus temperature plot of FIG. 14B for crude oil sample 2 shows only minor variation near the WAT.

The repeatable and clear step changes observed near the WATs of crude oils 1 and 2 suggest that the SPR sensor and workflow of FIG. 7 is capable of detecting precipitation and deposition events near the metallic surface of the SPR sensor.

Figures 16A, 16B, 16C:
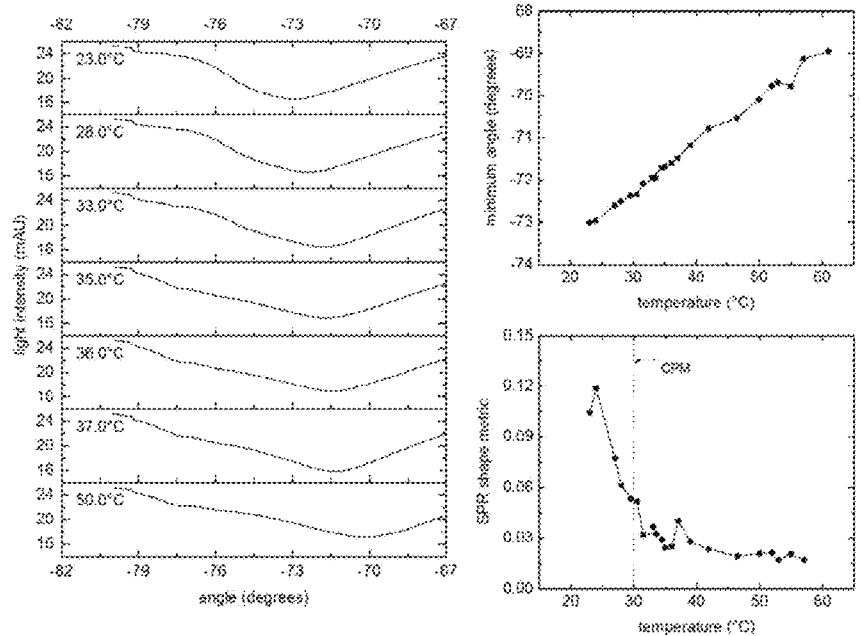
FIGS. 16A-16C and 17 are plots of data derived from the workflow of FIG. 7 in order to determine the WAT of a crude oil sample (referred to as "crude oil 3 sample").
Figure 18:
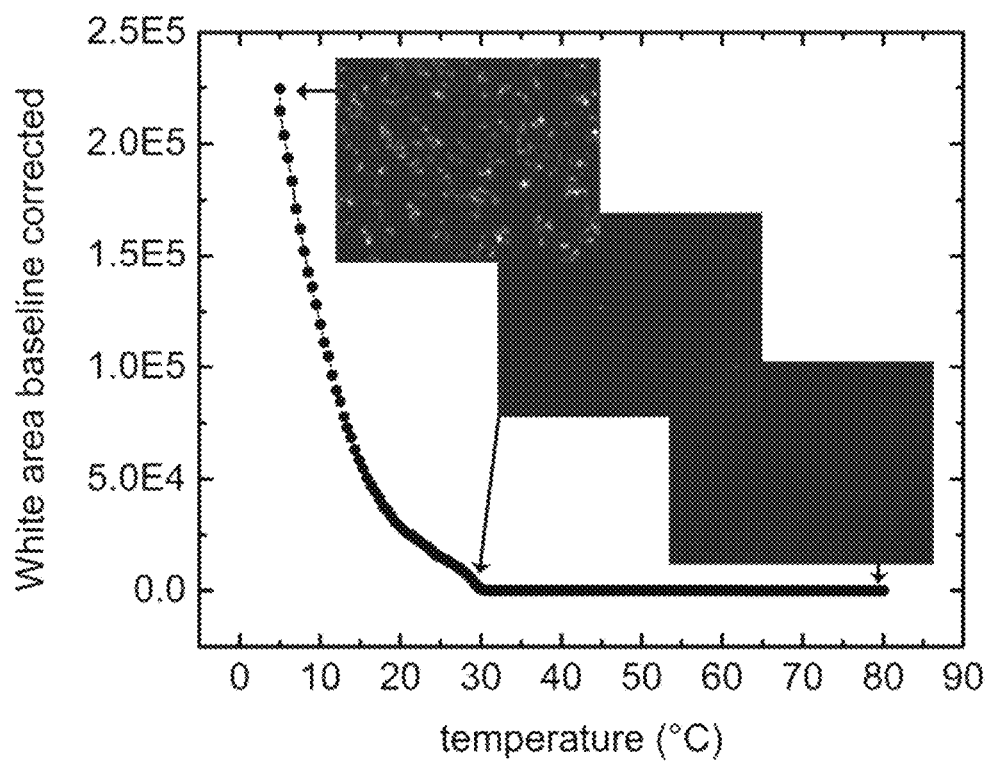
FIG. 18 are CPM images and data corresponding to the measurement of WAT for the crude oil sample 3 of FIGS. 16A-16C and 17.

FIGS. 16A-16C are plots of data derived from the workflow of FIG. 7 in order to determine the WAT of a crude oil sample (referred to as "crude oil 3 sample"), with a measured WAT of 30° C. using CPM. The CPM images and data are shown in FIG. 18. The crude oil 3 sample is known for its asphaltene deposition tendency and thus was tested to evaluate measurement robustness. FIG. 16A includes plots of the nominal intensity data as function of angular position of the thermally-controlled block (prism) at various temperatures for the crude oil 3 sample. Similar to the case of the binary mixtures of n-alkanes, the crude oil 1 sample, and the crude oil sample 2, it is not visually apparent from the nominal intensity data of FIG. 16A where the WAT occurs. Note that intensity data detected by the photodetector and lock-in amplifier over the angular positions of the thermally-controlled block (prism) at each one of the various temperatures can be plotted as angular block position of minimum intensity over the angular positions of the thermally-controlled block (prism) as a function of set point temperature as shown in FIG. 16B and as values of the SPR shape metric of Eqn. (2) as a function of set point temperature as shown in FIG. 16C. It is difficult to identify discernable abrupt changes in the plots of the FIGS. 16B and 16C. Note that the SPR minimum peak angle versus temperature plot of FIG. 16B for crude oil sample 3 shows only minor variation near the WAT.

Figure 17:
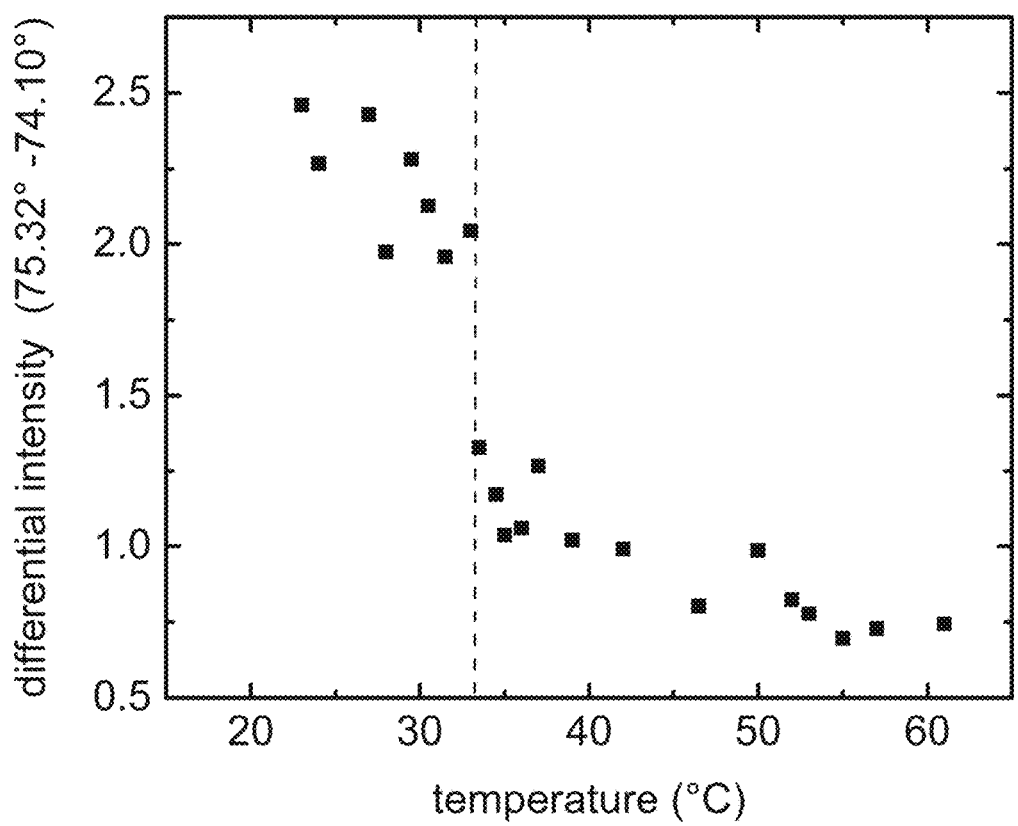

To determine WAT for the crude oil sample 3, a differential approach may be used, where the light intensity at one fixed angle is subtracted from the light intensity at another nearby fixed angle. This, in effect, baseline corrects the SPR data for any unwanted noise that may result from co-precipitation/deposition events. FIG. 17 shows the results of this approach where the nominal intensity data at −74.10° is subtracted from the nominal intensity data at −75.32° for each set point temperature and the resultant values are plotted as a function of temperature. The resultant plot shows an abrupt change in differential intensity data at approximately 33° C. This is 3° C. above the CPM measured WAT, and may suggest that the SPR sensing technique can possibly be able to detect sub-micron deposition events not visible with current microscopy based wax detection methodologies.

Thus, the results of FIGS. 9A-17 demonstrate that the SPR sensor of FIGS. 1 and 2 and workflow of FIG. 7 is capable of determining WAT for a wide range of hydrocarbon fluids.

In some embodiments, the computer processing system 250 of the SPR sensor can generate and store intensity data based on the electrical signal generated by the photodetector 130 and lock-in amplifier 111 for test measurements involving controlled rotational movement of the prism 120 relative to the monochromatic light source 110 with the hydrocarbon-based analyte loaded into the sample chamber 150 (or flowing-thru the sample chamber 150). The computer processing system 250 can process the intensity data as a function of angular positions of the prism 120 relative to the monochromatic light 110 to detect a phase transition with respect to the hydrocarbon-based analyte and/or determine at least one property relating to a phase transition of the hydrocarbon-based analyte. For example, the intensity data corresponding to different angular positions of the prism 120 relative to the monochromatic light source 110 can be evaluated to detect a phase change or related property with respect to the hydrocarbon-based analyte based on abrupt changes or other signal metrics measured from intensity data. In this embodiment, automated control of the temperature and pressure of the hydrocarbon-based analyte in the sample chamber is optional and thus the temperature control elements and pressure control elements of the SPR sensor can be omitted from the design, if desired.

Second Illustrative Embodiment

Figure 19:
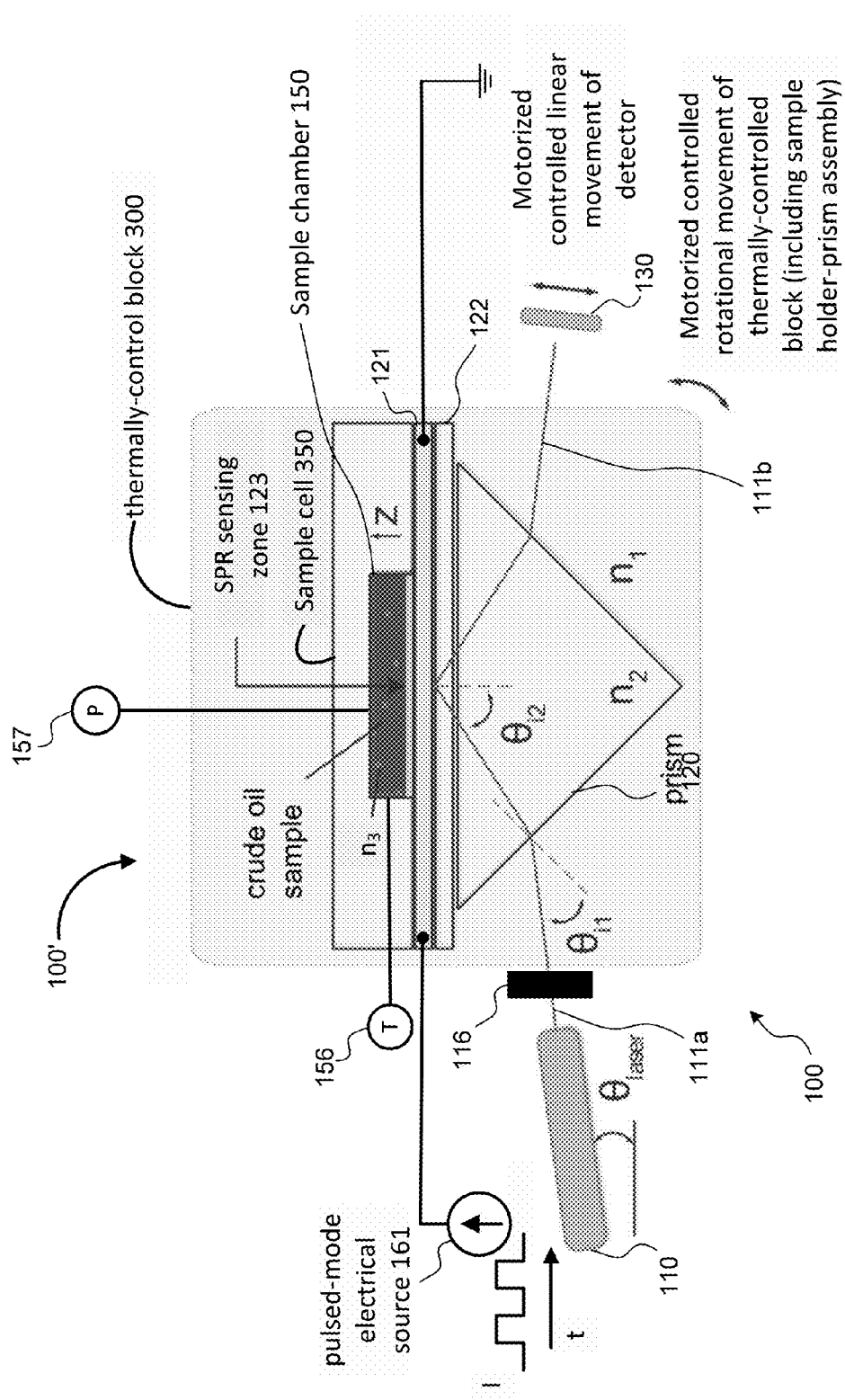
FIG. 19 is a schematic diagram illustrating a second embodiment of an SPR sensor configured to determine at least one property relating to phase change of a hydrocarbon-based analyte.

A second illustrative embodiment of an SPR sensor is shown in FIG. 19, which includes a sensor head 100' similar to the sensor head 100 of FIG. 1 and the associated support systems shown in FIG. 2. In this second illustrative embodiment, an electrical square waveform is applied to metallic film 121 in order to induce heating of the metallic film 121 and thus heating of the localized hydrocarbon fluid (in sample chamber 150) in the SPR sensing zone 123 in the vicinity of the metallic film 121. The electrical square waveform can be supplied by a pulsed-mode electrical source 161 that is electrically connected to one side of the metallic film 121 with the opposite side of the metallic film 121 electrically connected to ground potential. The pulsed-mode electrical source 161 can be a pulsed-mode current source or a pulsed mode voltage source. During the off-cycle of pulsed-mode electrical source 161, the metallic film 121 returns to the sample chamber 150 temperature. During the on-cycle of pulsed-mode electrical source 161, the metallic film 121 is heated via resistive heating thereby raising the temperature of the metallic film (for example, by 2-4° C. above the temperature of the sample chamber 150).

The operations of the SPR sensor of FIG. 19 are similar to the operations of first embodiment SPR sensor of FIGS. 1 and 2 as described above. Moreover, during such operations, the magnitude of the electrical driving power of the pulsed-mode electrical source 161 can be configured to provide user selectable temperature cycling. At conditions of interest, the temperature cycling provided by the pulsed-mode heating can produce a drastic change in the local permittivity within the vicinity of the metallic film 121 and would show up as an abrupt change in the minimum intensity of the reflected light beam as detected by the photodetector 130. The change in the minimum intensity of the reflected light beam over time can possibly yield a square wave signal, matching the frequency of the driving current. This response can be detected in order to determine the at least one property relating to phase change of the hydrocarbon-based analyte, which improve the accuracy and signal-to-noise ratio of the measurement.

For example, by applying power cycling to the thin metallic film 121, it is possible to repeatedly cross the phase transition boundary. For example, if the sample chamber 150 was at a temperature slightly below the dewpoint of a hydrocarbon fluid sample, the off-cycle would produce a hydrocarbon liquid film in the SPR sensing zone 123, and the on-cycle would subsequently vaporize the liquid hydrocarbon film. This would produce a drastic change in the local permittivity within the vicinity of the metallic film 121 (liquid-to-vapor) and would show up as a dramatic shift in SPR minimum peak angle. The SPR minimum angle versus time can yield a square wave signal, matching the frequency of the driving current. By repeatedly crossing the phase transition boundary, liquid-to-gas then gas-to-liquid, etc., both accuracy and signal-to-noise ratio in determining phase transitions can be greatly improved.

Third Illustrative Embodiment

Figure 20:
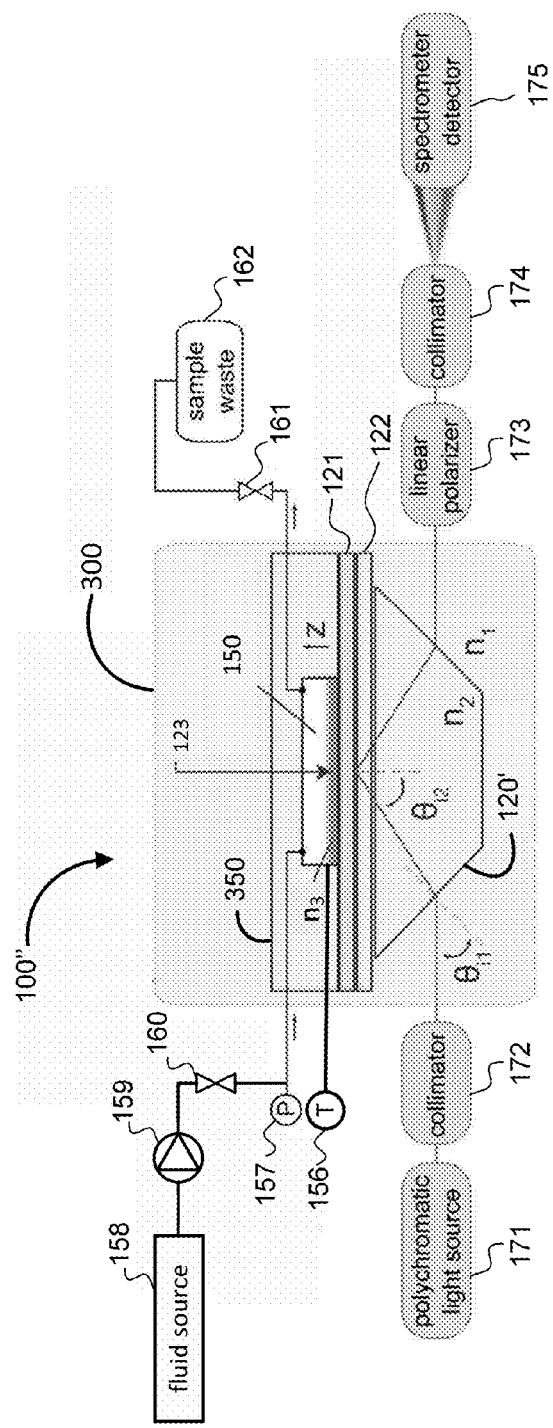
FIG. 20 is a schematic diagram illustrating a third embodiment of an SPR sensor configured to determine at least one property relating to phase change of a hydrocarbon-based analyte.
Figure 21:
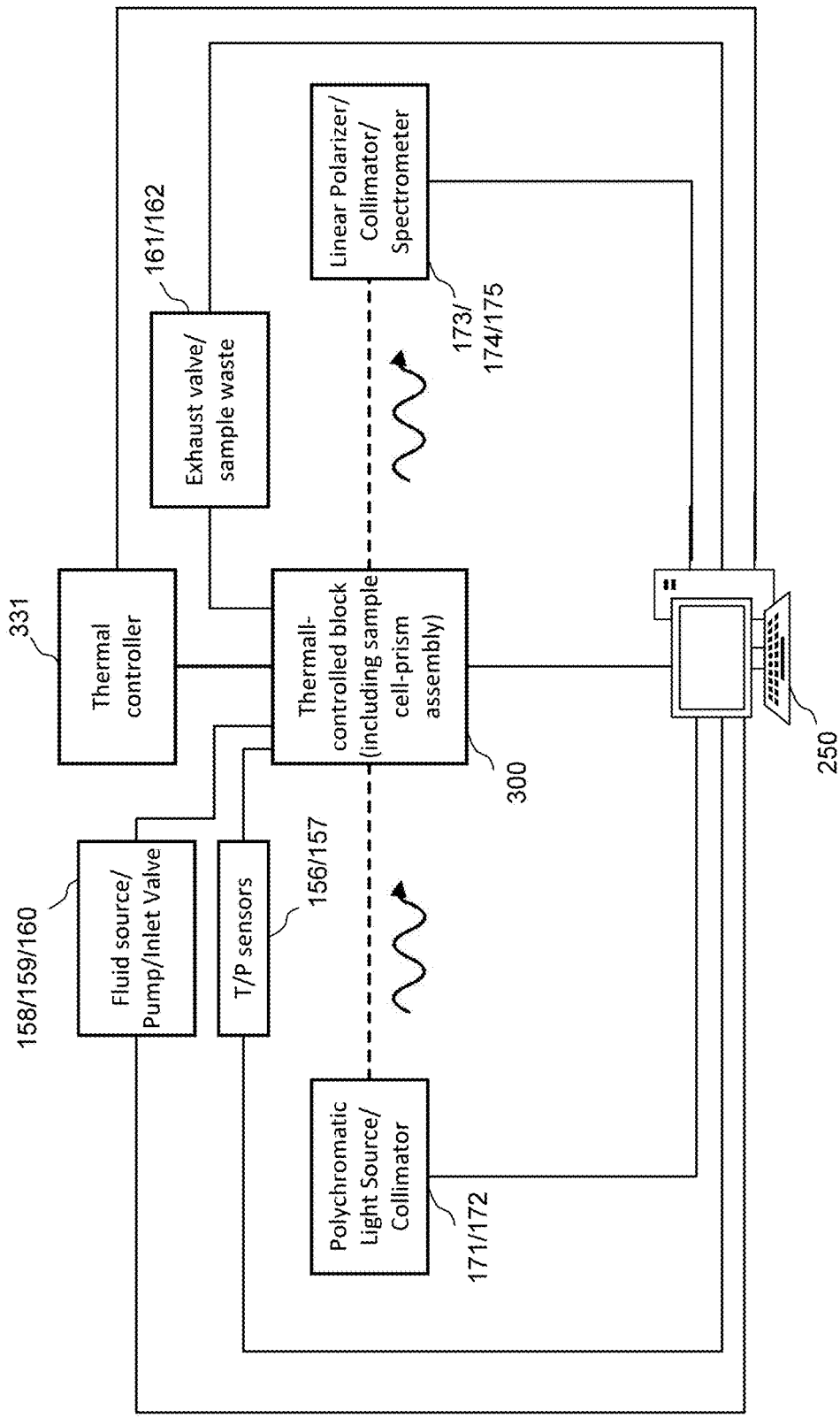
FIG. 21 is a block diagram of components of the second embodiment SPR sensor of FIG. 20.

A third illustrative embodiment of an SPR sensor is shown in FIG. 20, which includes a sensor head 100" similar in some aspects to the sensor head 100 of FIGS. 1 and 19 and associated support systems shown in FIG. 21. In this third illustrative embodiment, a polychromatic light source 171 with collimating optics 172 replaces the monochromatic light source 110 and polarizer and mechanical chopper (labeled 116) of the first and second illustrative embodiments. Furthermore, a linear polarizer 173, collimating optics 174 and a spectrometer 175 replaces the photodetector 130 and lock-in amplifier 135 of the first and second illustrative embodiments. The polychromatic light source 171 can be a tungsten halogen light supplying polychromatic radiation at wavelengths from 400-2400 nm, although other wavelengths or light source types may be used as per application.

Note that there are no moving parts to this system such that motorized rotational stage 332, the motorized linear stage 335 and the motor driver and feedback elements 210 of FIG. 2 can be omitted. It is further noted that the example of FIG. 20A utilizes a dove prism 120' as opposed to the triangular prism 120 of the first and second illustrative embodiments. It should be understood that prisms differing in geometry from those shown in FIGS. 1, 19 and 20A may be provided in other examples.

In the third illustrative embodiment, the polychromatic light source 171 can be configured to direct a polychromatic light beam to the prism 120', which couples the incident polychromatic light beam onto the optical substrate 122 that is coated with a thin semitransparent noble metal film (metallic film 121) under conditions of total internal reflection. Alternatively, a face of the prism 120' can be coated with the metallic film 121 and the optical substrate 122 can be omitted. Similar to the embodiments that utilize a monochromatic light source, at the point of reflection of the polychromatic light beam at the interface of the metallic film 121, surface plasmon resonance can occur where an evanescent field (standing wave) will penetrate beyond the metallic film 121 in an SPR sensing zone 123 hat is in the immediate vicinity of the metallic film 121 (i.e., less than 1

μm away). A sample cell 350 is fixed in position relative to the prism 120' and the metallic film 121/optical substrate 122 as part of an assembly. The sample cell 350 defines a fixed-volume sample chamber 150 that is adjacent the metallic film. In this configuration, part of the fixed-volume sample chamber 150 lies in the SPR sensing zone 123 adjacent the metallic film 121. The other faces of the prism 120' are unblocked to allow the polychromatic light beam to enter the prism 120' and exit the prism 120' after reflection at the interface of the metallic film 121. The linear polarizer 173, collimating optics 174 and spectrometer 175 are configured along an optical path such that the spectrometer 175 is configured to receive the reflected light beam that is output from the output face of the prism 120'. The spectrometer 175 measures an SPR spectrum that represents the intensity of the reflected light beam that is output from the output face of the prism 120' as a function of wavelength.

Similar to the embodiments that utilizes a monochromatic light source and prism, the assembly (e.g., the sample cell 350, prism 120' and the metallic film 121/optical substrate 122) can include one or more temperature control elements (such as one or more heat exchangers 320 and associated temperature controller 331, one or more Peltier thermal-electric elements 315 and/or one or more heat sinks 317 as described above with respect to FIGS. 3-5) for use in controlling the temperature of the sample cell 350 and prism 120' of the assembly during operation of the SPR sensor. The assembly can also include a temperature sensor 156 (which is preferably integrated into the sample cell 350) that can interface to the computer processing system 250 for use in monitoring and controlling the temperature of the sample cell 350 and prism 120' of the assembly during operation of the SPR sensor as well as a pressure sensor 157 (which is preferably integrated into the sample cell 350) that can interface to the computer processing system 250 for use in monitoring and controlling the pressure of analyte fluid in the sample chamber 150 of the sample cell 350 during operation of the SPR sensor.

The SPR sensor of FIGS. 20 and 21 can be used to measure temperature and/or pressure conditions that correspond to a phase transition in a hydrocarbon-based analyte through experiments under constant pressure conditions where the temperature of the hydrocarbon-based analyte is controllably varied over a range of set point temperatures. An example of such phase transition measurement is wax appearance temperature (WAT) for a sample of crude oil or other reservoir fluid. In this case, the hydrocarbon-based analyte can be loaded into the fixed-volume sample chamber 150 of the SPR sensor at a set pressure. Pressure control of the hydrocarbon-based analyte can be established using one or more pressure control elements that control the pressure of the hydrocarbon-based analyte in the sample chamber 150 to a set pressure as monitored by the pressure transducer 157. Such pressure control element(s) can include a pump 159 (e.g., syringe pump) and possibly one or more isolation valves (e.g., an inlet valve 160 and/or exhaust valve 161) that are in fluid communication with the fixed-volume sample chamber 150 as shown in FIG. 20. With the hydrocarbon-based analyte at the controlled set pressure in the sample chamber 150, the computer processing system 250 can be configured to perform a sequence of test measurements over a range of set point temperatures. In each test measurement of the sequence, the computer processing system 250 can be configured to perform a number of operations, including:

i) the computer processing system 250 interfaces to the temperature control elements (e.g., temperature controller 331 and one or more Peltier thermal-electric elements 315 of the thermally-controlled block 330) of the SPR sensor to control the temperature of the sample cell 350 and prism 120' at the desired set point temperature of the specific test measurement as monitored by the temperature sensor 156; the computer processing system 250 can be configured to allow the temperature of the sample cell 250 and prism 120' to reach steady state at the set point temperature prior to acquiring the intensity measurements of the reflected light beam during acquisition of the SPR spectrum in ii) below; and ii) the computer processing system 250 acquires and stores the SPR spectrum output by the spectrometer 175; the SPR spectrum represents the intensity of the reflected light beam that is output from the output face of prism 120' as a function of wavelength; the SPR spectrum is sensitive to the surface plasmon resonance at the interface of the metallic film 121 of the SPR sensor.

The hydrocarbon-based analyte can be loaded into the sample chamber 150 of the sample cell 350 by the pump 159 (such as a syringe pump) and inlet valve 160. When the test measurements of the sequence are complete, the hydrocarbon-based analyte can be removed from the sample chamber 150 of the sample cell 350 through the exhaust valve 161 and/or waste line 162.

The SPR spectra stored by the computer processing system 250 for the sequence of test measurements can be evaluated and/or processed in order to determine at least one property relating to a phase change of the hydrocarbon-based analyte.

In some embodiments, the at least one property relating to phase change of the hydrocarbon-based analyte can detected by identifying temperature conditions (i.e., one or more set point temperatures) that produce a shift in a local minima or dip in the SPR spectra as measured by the spectrometer 175 over the range of set point temperatures, or by identifying temperature conditions (i.e., one or more set point temperatures) that produce other signal metrics in the SPR spectra as measured by the spectrometer 175 over the range of set point pressures.

Figure 22:
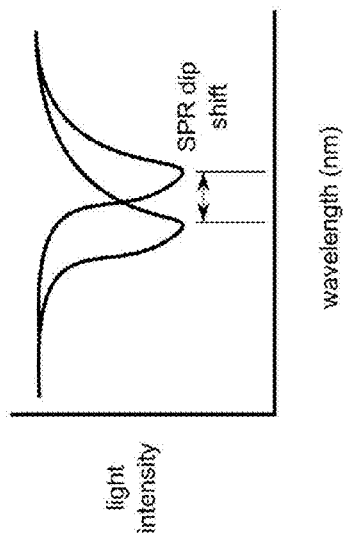
FIG. 22 is a plot of SPR spectra acquired by the SPR sensor of FIG. 20, which show a shift in a local minimum or trough or dip in the SPR spectra that can be used to determine at least one property relating to phase change of a hydrocarbon-based analyte.

An example of such a shift in a local minima or dip in the SPR spectra as measured by the spectrometer 175 is depicted graphically in FIG. 22.

The SPR sensor of FIGS. 20 and 21 can also be used to measure temperature and/or pressure conditions that correspond to a phase transition in a hydrocarbon-based analyte through experiments under constant temperature conditions where the pressure of the hydrocarbon-based analyte is controllably varied over a range of set point pressures. An example of such phase transition measurement is asphaltene onset pressure (where asphaltenes precipitate and form a solid film) for a sample of crude oil. In this case, the temperature of the hydrocarbon-based analyte, the sample cell 150 and prism 120 of the SPR sensor can be controlled to a desired set temperature. Temperature control can be established by using the temperature control elements (e.g., temperature controller 331 and one or more Peltier thermal-electric elements 315 of the thermally-controlled block 330) of the SPR sensor to control the temperature of the sample cell 350 and prism 120' at the desired set temperature as monitored by the temperature sensor 156. With the hydrocarbon-based analyte in the fixed volume sample chamber 150 of the sample cell 350 at the controlled set temperature, the computer processing system 250 can be configured to perform a sequence of test measurements over a range of set point pressures. In each test measurement of the sequence, the computer processing system 250 can be configured to perform a number of operations, including:

i) the computer processing system interfaces to one or more pressure control elements that controls the pressure of the hydrocarbon-based analyte in the sample chamber 150 at the set point pressure of the respective test measurement as monitored by the pressure transducer 157; such pressure control element(s) can include pump 159 (e.g., syringe pump) and possibly one or more isolation valves (e.g., an inlet valve 160 and/or exhaust valve 161) that are in fluid communication with the fixed-volume sample chamber 150 of the SPR sensor; the computer processing system 250 can be configured to allow the pressure of the hydrocarbon-based analyte in the sample chamber 150 to reach steady state at the set point pressure prior to acquiring the SPR spectrum as described in ii) below; and ii) the computer processing system 250 acquires and stores the SPR spectrum output by the spectrometer 175; the SPR spectrum represents the intensity of the reflected light beam that is output from the output face of prism 120' as a function of wavelength; the SPR spectrum is sensitive to the surface plasmon resonance at the interface of the metallic film 121 of the SPR sensor.

The hydrocarbon-based analyte can be loaded into the sample chamber 150 of the sample cell by pump 159 (such as a syringe pump) and inlet valve 160. When the test measurements of the sequence are complete, the hydrocarbon-based analyte can be removed from the sample chamber 150 of the sample cell 350 through an exhaust valve 161 and/or waste line 162.

The SPR spectra stored by the computer processing system 250 for the sequence of test measurements can be evaluated and/or processed in order to determine at least one property relating to phase change of the hydrocarbon-based analyte.

In some embodiments, the at least one property relating to phase change of the hydrocarbon-based analyte can detected by identifying pressure conditions (i.e., one or more set point pressures) that produce a shift in a local minima or dip in the SPR spectra as measured by the spectrometer 175 over the range of set point pressures, or by identifying pressure conditions (i.e., one or more set point pressures) that produce other signal metrics in the SPR spectra as measured by the spectrometer 175 over the range of set point pressures.

An example of such a shift in a local minima or dip in the SPR spectra as measured by the spectrometer 175 is depicted graphically in FIG. 20B.

The SPR sensor of FIGS. 20 and 21 can also be used to measure temperature and pressure conditions that induce phase transitions in a hydrocarbon-based analyte through experiments with controlled variations in both the temperature and pressure conditions of the hydrocarbon-based analyte. Examples of such phase transition measurements is bubble point, dew point and other phase transitions in a sample of crude oil, condensate gas or other reservoir fluid. In this case, the temperature of the hydrocarbon-based analyte, the sample cell 350 and prism 120 of the SPR sensor can be controlled to a desired set temperature above the phase transition temperature—typically the sample's reservoir temperature. Temperature control can be established by using the temperature control elements (e.g., temperature controller 331 and one or more Peltier thermal-electric elements 315 of the thermally-controlled block 330) of the SPR sensor to control the temperature of the sample cell 350 and prism 120' at the desired set temperature as monitored by the temperature sensor 156. With the hydrocarbon-based analyte in the fixed volume sample chamber 150 of the sample cell 350 at the controlled set temperature, the computer processing system 250 can be configured to perform a sequence of test measurements over a range of set point pressures (referred to as a "pressure loop"). In each test measurement of the pressure loop, the computer processing system 250 can be configured to perform a number of operations, including:

i) the computer processing system 250 interfaces to one or more pressure control elements that controls the pressure of the hydrocarbon-based analyte in the sample chamber 150 at the set point pressure of the respective test measurement as monitored by the pressure transducer 157; such pressure control element(s) can include pump 159 and possibly one or more isolation valves (e.g., an inlet valve 160 and/or exhaust valve 161) that are in fluid communication with the fixed-volume sample chamber 150 of the SPR sensor; the computer processing system 250 can be configured to allow the pressure of the hydrocarbon-based analyte in the sample chamber 150 to reach steady state at the set point pressure prior to acquiring the SPR spectrum as described in ii) below; and ii) the computer processing system 250 acquires and stores the SPR spectrum output by the spectrometer 175; the SPR spectrum represents the intensity of the reflected light beam that is output from the output face of prism 120' as a function of wavelength; the SPR spectrum is sensitive to the surface plasmon resonance at the interface of the metallic film 121 of the SPR sensor.

After the pressure loop is fully executed (or a phase transition has been detected), the computer processing system 250 can be configured to control the pressure of the hydrocarbon-based analyte in the sample chamber 150 such that such pressure returns to reservoir pressure. If necessary, the computer processing system 250 can control temperature of the sample cell 350 and prism 120' by decrementing such temperature by a set amount, and the pressure loop is executed again. The temperature parent loop (along with the children pressure loops) can be executed until a lower temperature limit is reached. The pressure loops and temperature loops can be executed independently or in a nested manner as required by the type of phase transition targeted.

The hydrocarbon-based analyte can be loaded into the sample chamber 150 of the sample cell 350 by pump 159 (such as a syringe pump) and inlet valve 160. When the pressure loops and temperature loops are complete, the hydrocarbon-based analyte can be removed from the sample chamber 150 of the sample cell 350 through an exhaust valve 161 and/or waste line 162.

The SPR spectra stored by the computer processing system 250 over the test measurements of the pressure loops and temperature loops can be evaluated and/or processed in order to determine at least one property relating to phase change of the hydrocarbon-based analyte.

In some embodiments, the at least one property relating to phase change of the hydrocarbon-based analyte can detected by identifying temperature and pressure conditions (i.e., one or more set point temperatures and pressures) that produce a shift in a local minima or dip in the SPR spectra as measured by the spectrometer over the range of controlled temperatures and pressures, or by identifying temperature and pressure conditions (i.e., one or more set point temperatures and pressures) that produce other signal metrics in the SPR spectra as measured by the spectrometer over the range of controlled temperatures and pressures.

An example of such a shift in a local minima or dip in the SPR spectra as measured by the spectrometer 175 is depicted graphically in FIG. 20B.

Note that the mechanisms that supply electrical square waveform to the metallic film of the SPT sensor in FIG. 19 can readily be adapted for use in the SPR sensor of FIGS. 20 and 21 as described herein.

In some embodiments, the computer processing system 250 of the SPR sensor of FIG. 20 can acquire and store the SPR spectra (spectra data) output by the spectrometer 175 for test measurements with the hydrocarbon-based analyte loaded into the sample chamber 150 (or flowing-thru the sample chamber 150). The computer processing system 250 can process the SPR spectra to detect a phase transition with respect to the hydrocarbon-based analyte and/or determine at least one property relating to a phase transition of the hydrocarbon-based analyte. For example, the SPR spectra can be evaluated to detect a phase change or related property with respect to the hydrocarbon-based analyte based on a shift in a local minima or dip in the SPR spectra or other signal metrics measured from SPR spectra. In this embodiment, automated control of the temperature and pressure of the hydrocarbon-based analyte in the sample chamber is optional and thus the temperature control elements and pressure control elements of the SPR sensor can be omitted from the design, if desired.

Fourth Illustrative Embodiment

Figure 23A:
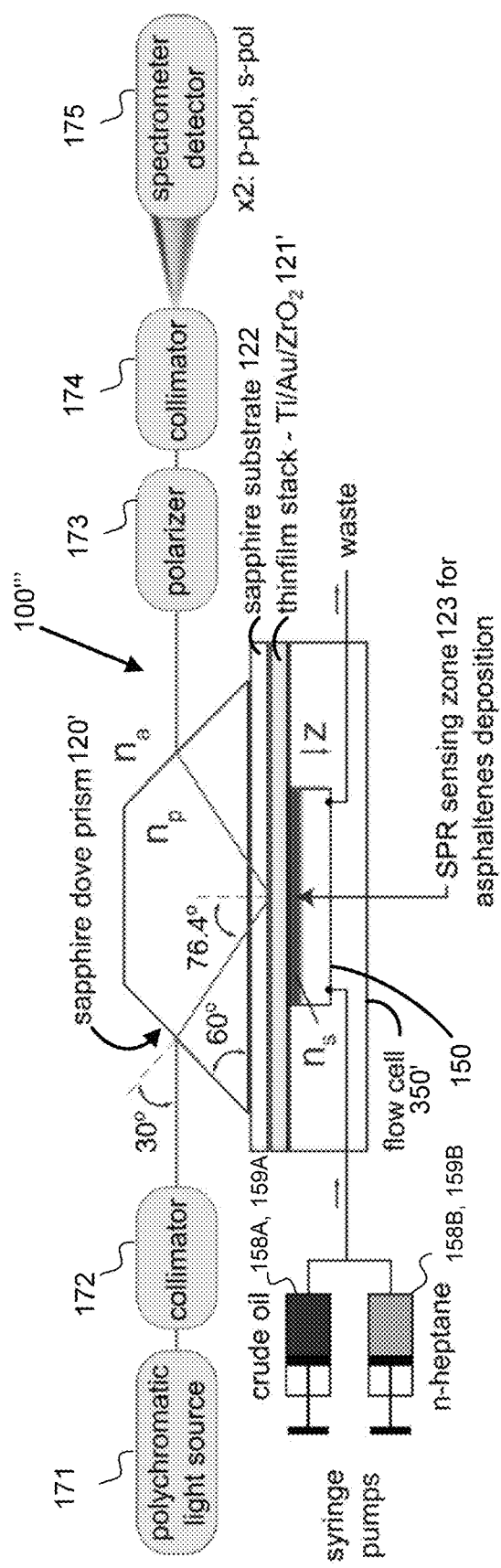
FIG. 23A is a is a schematic diagram illustrating a fourth embodiment of an SPR sensor configured to determine at least one property relating to phase change of a hydrocarbon-based analyte.

A fourth illustrative embodiment of an SPR sensor is shown in FIG. 23A, which includes a sensor head 100''' similar in some aspects to the sensor head 100'' of FIG. 20 and associated support systems shown in FIG. 21. In this fourth illustrative embodiment, a polychromatic light source 171 with collimating optics 172 directs a polychromatic light beam to the prism 120', which couples the incident polychromatic light beam onto the optical substrate 122 that is coated with a thin film stack 121' under conditions of total internal reflection. The polychromatic light source 171 can be a tungsten halogen light supplying polychromatic radiation at wavelengths from 400-2400 nm, although other wavelengths or light source types may be used as per application. The thin film stack 121' includes a layer of titanium (Ti) that interfaces to the optical substrate 122, a layer of gold (Au) formed on the Ti layer, and a layer of zirconium oxide ($ZrO_2$) formed on the intermediate Au layer. The $ZrO_2$ layer functions as a barrier layer to protect the underlying metal layers from possible reactants (such as hydrogen sulfide and mercury) commonly found in hydrocarbon fluids. It can also function to shift the dynamic range (wavelengths) of the SPR peaks measured by the SPR sensor and thus can provide the capability to tune the operational wavelengths measured by the SPR sensor over a limited range if desired. Alternatively, a face of the prism 120' can be coated with the thin film stack 121' and the optical substrate 122 can be omitted. Similar to the third embodiment SPR sensor, at the point of reflection of the polychromatic light beam at the interface of the thin film stack 121', surface plasmon resonance can occur where an evanescent field (standing wave) will penetrate beyond the thin film stack 121' in an SPR sensing zone 123 that is in the immediate vicinity of the thin film stack 121' (i.e., less than 1 μm away). A flow-thru cell 350' is fixed in position relative to the prism 120' and the thin film stack 121'/optical substrate 122 as part of an assembly. The flow-thru cell 350 defines a sample chamber 150 that is adjacent the thin film stack 121'. In this configuration, part of the sample chamber 150 lies in the SPR sensing zone 123 adjacent the thin film stack 121'. The other faces of the prism 120' are unblocked to allow the polychromatic light beam to enter the prism 120' and exit the prism 120' after reflection at the interface of the thin film stack 121' The linear polarizer 173, collimating optics 174 and spectrometer 175 are configured along an optical path such that the spectrometer 175 is configured to receive the reflected light beam that is output from the output face of the prism 120'. The spectrometer 175 measures an SPR spectrum that represents the intensity of the reflected light beam that is output from the output face of the prism 120' as a function of wavelength.

Similar to the third embodiment, the assembly (e.g., the flow-thru cell 350', prism 120' and the thin film stack 151'/optical substrate 122) can include one or more temperature control elements (such as one or more heat exchangers 320 and associated temperature controller 331, one or more Peltier thermal-electric elements 315 and/or one or more heat sinks 317 as described above with respect to FIGS. 3-5) for use in controlling the temperature of the flow-thru cell 350' and prism 120' of the assembly during operation of the SPR sensor. The assembly can also include a temperature sensor (which is preferably integrated into the flow-thru cell 350') that can interface to the computer processing system 250 for use in monitoring and controlling the temperature of the flow-thru cell 350' and prism 120' of the assembly during operation of the SPR sensor as well as pressure sensors (which are preferably integrated into the flow-thru cell 350') that can interface to the computer processing system 250 for use in monitoring and controlling the pressure of analyte fluid in the sample chamber 150 of the flow-thru cell 350' during operation of the SPR sensor.

The SPR sensor of FIG. 23A can be used to measure temperature and/or pressure conditions that correspond to a phase transition in a hydrocarbon-based analyte through a variety of experiments similar to those described above for the third embodiment. In this configuration, the measurement (test sequences) can be carried out with hydrocarbon-based analyte flowing through the flow-thru cell under constant pressure conditions with a constant differential pressure between the inlet (supply) side and exhaust (waste) side of the flow-thru cell.

Note that the mechanisms that supply electrical square waveform to the metallic film of the SPT sensor in FIG. 19 can readily be adapted for use in the SPR sensor of FIG. 23A as described herein.

Also, note that the thin film stack 151' of the SPR sensor of FIG. 23A can replace the metallic film 151 in the SPR sensors of the embodiments of FIGS. 1, 19 and 20. Furthermore, the flow-thru cell 350' of the SPR sensor of FIG. 23A can replace the sample cell 250 in the SPR sensors of the embodiments of FIGS. 1, 19 and 20.

The SPR sensor of FIG. 23A can also be used to measure the onset and deposition of asphaltenes from a titration experiment. In this experiment, the hydrocarbon-based analyte (such as a crude oil sample) can be stored in the reservoir 158A of a first syringe pump 159A with a diluent (such as n-heptane) stored in the reservoir 158B of a second syringe pump 159B. The syringe pumps 159A, 159B are controlled to vary the ratio of the hydrocarbon-based analyte and the diluent that flows through the flow-thru cell 350' over a sequence of test measurements. In each test measurement, as the fluid flow provided by the syringe pumps 159A, 159B flows through the flow-thru cell 350', the spectrometer 175 acquires and stores the SPR spectrum output by the spectrometer 175. This SPR spectrum represents the intensity of the reflected light beam that is output from the output face of prism 120' as a function of wavelength, and this SPR spectrum is sensitive to the surface plasmon resonance at the interface of the thin film stack 121' of the SPR sensor. The SPR spectra stored by the computer processing system 250 for the sequence of test measurements can be evaluated and/or processed in order to determine at least one property relating to a phase change of the hydrocarbon-based analyte. In some embodiments, the at least one property relating to phase change of the hydrocarbon-based analyte can detected by identifying shift in a local minima or dip in the SPR spectra as measured by the spectrometer 175 over the sequence of test measurements.

In some embodiments, other fluid handling elements (such as reservoirs, tanks, pumps, valves and flow lines), which can be computer controlled or manually controlled, can be used to control the ratio of the hydrocarbon-based analyte and the diluent that flows through the flow-thru cell 350' over the sequence of test measurements.

Figure 23B:
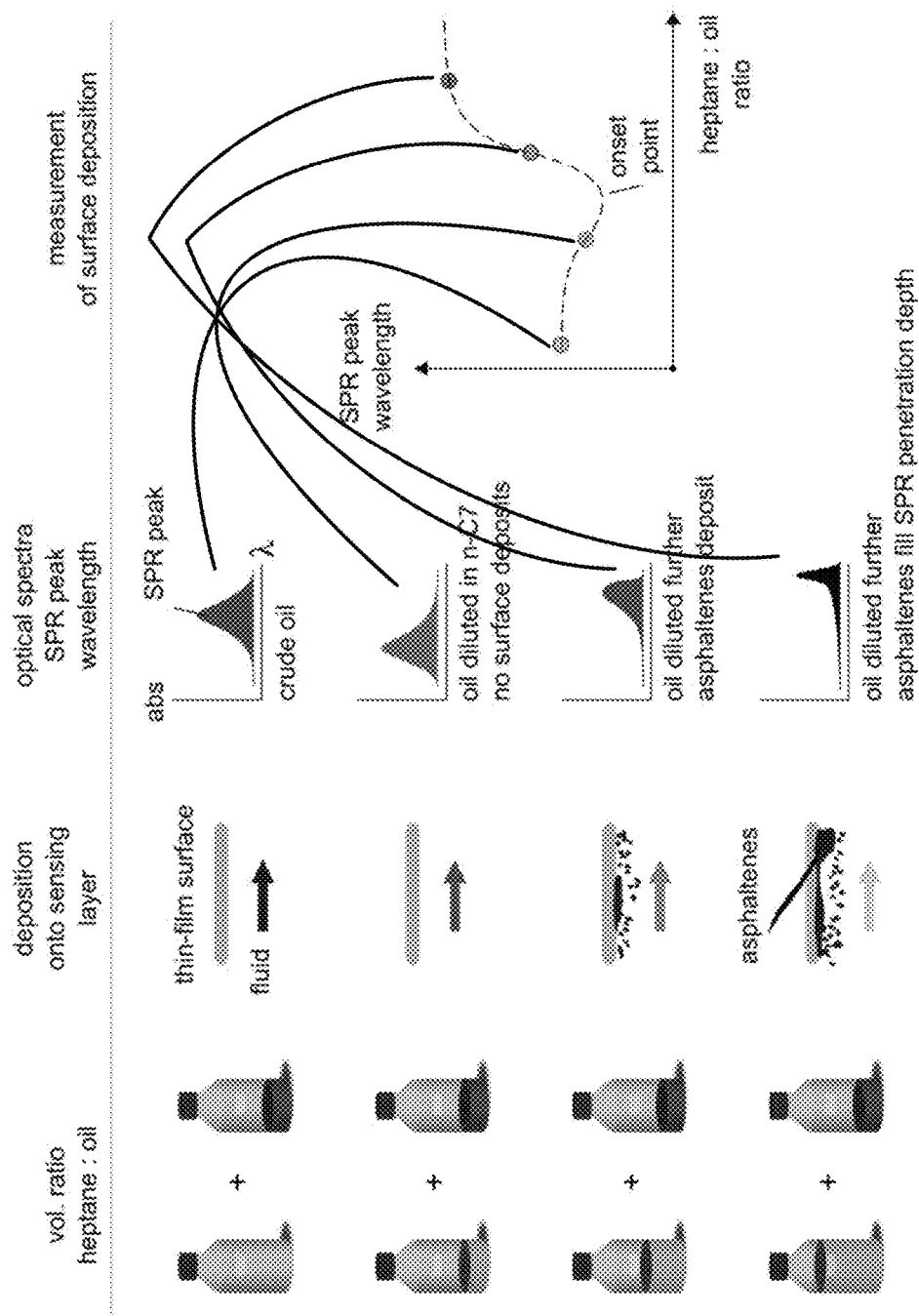
FIG. 23B is a schematic illustration which shows SPR spectra acquired by the spectrometer of the SPR sensor of FIG. 23A over a sequence of test measurements for an exemplary titration experiment.

FIG. 23B which shows SPR spectra acquired by the spectrometer 175 of the SPR sensor of FIG. 23A over a sequence of test measurements for an exemplary titration experiment. Initially, the SPR spectrum (and corresponding peak wavelength) of the neat crude oil sample (without any diluent) is measured. Next, the gradual addition of the diluent (n-heptane) dilutes the crude oil and the SPR spectra (and corresponding peak wavelength) for a number of resultant diluted mixtures are measured. Note that the SPR spectra for the resultant diluted mixtures produces a lower SPR peak wavelength, which results from the lower refractive index of the mixture. When the amount of added n-heptane as part of the resultant diluted mixture approaches the onset point, asphaltenes precipitate and are deposited onto the thin film stack 121' of the SPR sensor. Note that the SPR peak wavelength increases as the deposit is formed on the thin film stack 121' of the SPR sensor. With the amount of added n-heptane as part of the resultant diluted mixture increasing further beyond the ratio of the onset point, the asphaltenes continue to deposit on the thin film stack 121' until a deposit thicker than the SPR field penetration depth is reached. Even though the crude oil has been substantially diluted in n-heptane, the final SPR peak wavelength exceeds that of the native crude oil due to the dense asphaltene deposit on the surface.

These operations show that the SPR sensor of FIG. 23A can be used to perform real-time measurement of asphaltene/organic deposition under live conditions. Therefore, this SPR sensor can be used in a variety of oilfield applications, including detection of flow assurance as well as monitoring stability for operations like solvent dilution, sample depressurization, and commingling of different crude oils.

In some embodiments, the computer processing system 250 of the SPR sensor of FIG. 23A can acquire and store the SPR spectra (spectra data) output by the spectrometer 175 for test measurements with the hydrocarbon-based analyte flowing-thru the sample chamber 150. The computer processing system 250 can process the SPR spectra to detect a phase transition with respect to the hydrocarbon-based analyte and/or determine at least one property relating to a phase transition of the hydrocarbon-based analyte. For example, the SPR spectra can be evaluated to detect a phase change or related property with respect to the hydrocarbon-based analyte based on a shift in a local minima or dip in the SPR spectra or other signal metrics measured from SPR spectra. In this embodiment, automated control of pressure of the hydrocarbon-based analyte in the sample chamber is optional and thus the pressure control elements of the SPR sensor can be omitted from the design, if desired.

Oilfield Systems

FIG. 22 depicts a rig 10 suitable for employing certain downhole tool embodiments disclosed herein. In the depiction, rig 10 is positioned over (or in the vicinity of) a subterranean oil or gas formation (not shown). The rig may include, for example, a derrick and a hoisting apparatus for lowering and raising various components into and out of the wellbore 40. A downhole tool 51 is deployed in the wellbore 40. The downhole tool 51 may be connected to the surface, for example, via coiled tubing 50 which is in turn coupled to a coiled tubing truck 55.

During operation, the downhole tool 51 may be lowered into the wellbore 40. In a highly deviated borehole, the downhole tool 51 may alternatively or additionally be driven or drawn into the borehole, for example, using a downhole tractor or other conveyance means. The disclosed embodiments are not limited in this regard. For example, the downhole tool 51 may also be conveyed into the borehole 40 using drill pipe, a wireline cable or other conveyance methodologies.

The example downhole tool 51 described herein may be used to obtain and analyze samples of formation fluids in situ. For example, the formation fluid samples can include natural gas, various gas mixtures, oil or various oil mixtures. The downhole tool 51 can include a probe assembly 52 for establishing fluid communication between the downhole tool 51 and the subsurface formation. During operation, the probe assembly 52 may be extended into contact with the borehole wall 42 (e.g., through a mud cake layer). Formation fluid samples may enter the downhole tool 51 through the probe assembly 52 (e.g., via a pumping or via formation pressure). The downhole tool 51 also includes an SPR sensor 2640 (FIG. 26) for measuring at least one property relating to phase change of formation fluid sample that enters the downhole tool 51 through the probe assembly 52.

The probe assembly 52 may include a probe mounted in a frame (the individual probe assembly components are not shown). The frame may be configured to extend and retract radially outward and inward with respect to the sampling tool body. Moreover, the probe may be configured to extend and retract radially outward and inward with respect to the frame. Such extension and retraction may be initiated via an uphole or downhole controller. Extension of the frame into contact with the borehole wall 42 may further support the sampling tool in the borehole as well as position the probe adjacent the borehole wall 42.

In some embodiments, such as those used in low permeability formations, the probe assembly 52 may be replaced by packer assembly (not shown). The disclosed embodiments are not limited in this regard. As is known to those of ordinary skill in the art, a packer assembly, when inflated, is intended to seal and/or isolate a section of the borehole wall to provide a flow area with which to induce fluid flow from the surrounding formation.

The downhole tool 51 can also include a downhole telemetry subsystem (not shown) that communicates data signals and control signals between the downhole tool 51 and a surface-located data acquisition and control system, which can be part of the truck 55 or other surface-located system. The downhole telemetry subsystem can employ a variety of telemetry methods, such as wired telemetry methods that employ telemetry cables, drill pipe that incorporate telemetry cables, or fiber optic cables, and wireless telemetry methods, such as mud-pulse telemetry methods, electromagnetic telemetry methods, and acoustic telemetry methods. The downhole telemetry subsystem can also supply electrical power supply signals generated by a surface-located power source for supply to the downhole tool 51. The surface-located power source can be part of the truck 55 or other surface-located system. The downhole tool 51 can also include a power supply transformer/regulator for transforming the electric power supply signals supplied by the surface-located power source to appropriate levels suitable for use by the electrical components of the downhole tool 100. In alternate embodiments, the downhole tool 51 can include a downhole power source supply (such as a battery or turbine generator and/or energy harvester for logging while drilling tools) that supplies electrical power supply signals to the downhole tool 51.

Figure 25:
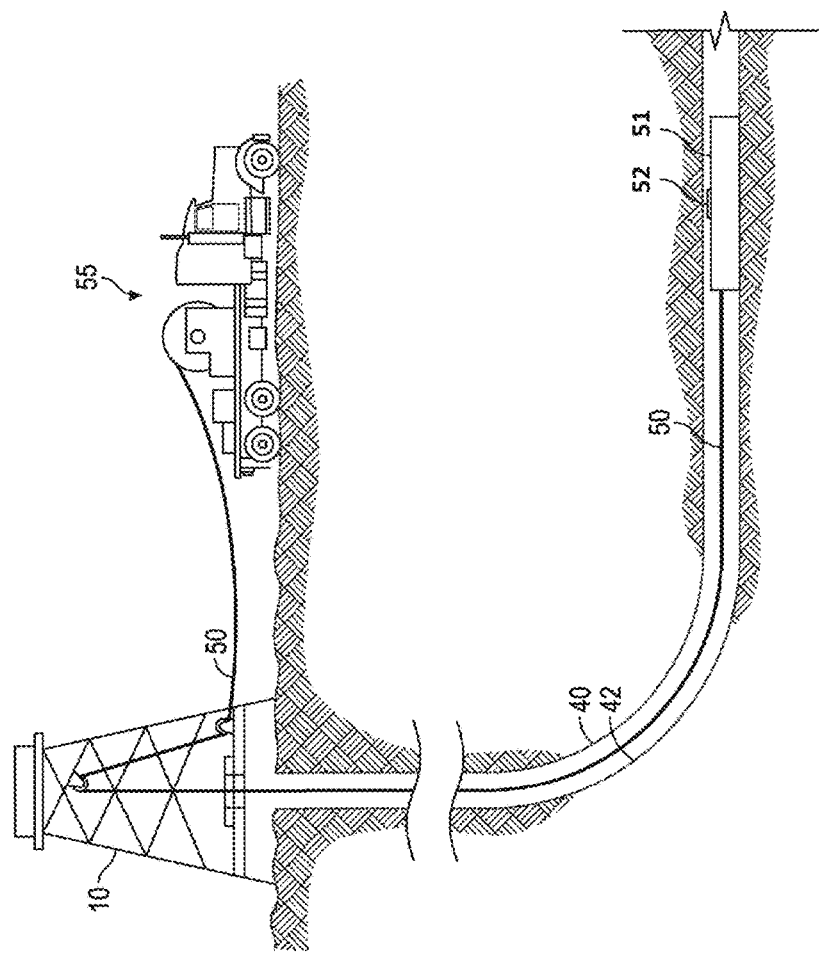
FIG. 25 is a schematic diagram showing one example of a rig on which disclosed downhole tool embodiments may be utilized.

While FIG. 25 depicts a particular downhole tool 51, it will be understood that the disclosed embodiments are not so limited. For example, downhole tool 51 may include a drilling tool such as a measurement while drilling or logging while drilling tool configured for deployment on a drill string. The disclosed embodiments are not limited in these regards.

Figure 26:
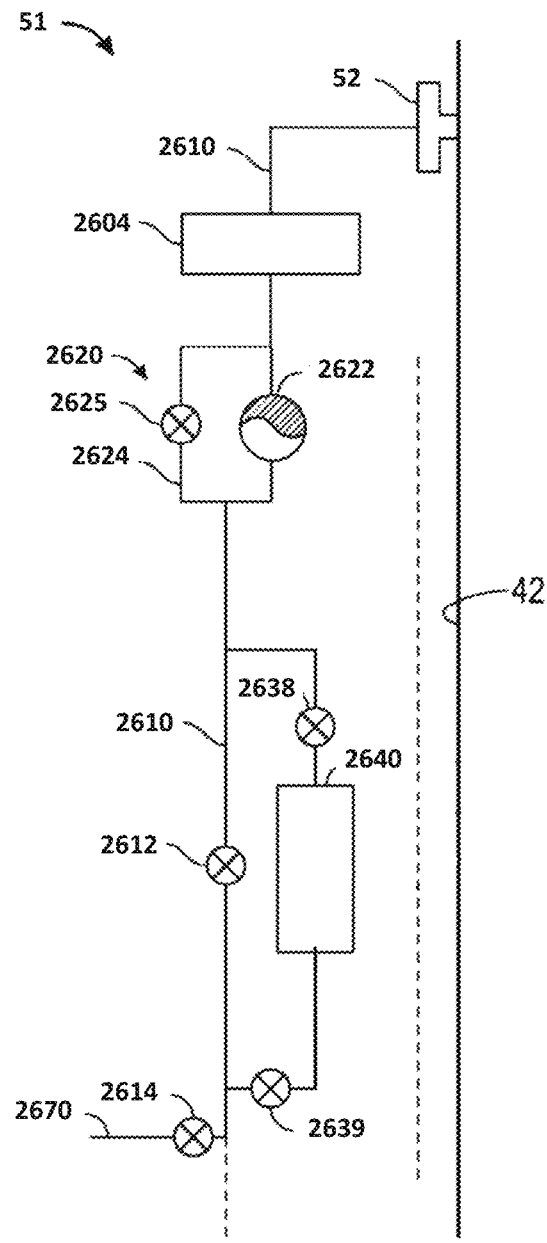
FIG. 26 is a schematic fluid flow circuit diagram of the downhole tool of FIG. 25 in which disclosed SPR sensor embodiments may be utilized.

FIG. 26 shows the fluid flow circuit of the downhole tool 51 of FIG. 24. The probe assembly 52 is depicted as being in contact with borehole wall 42 for obtaining a formation fluid sample. In the depicted embodiment, probe assembly 52 is in fluid communication with a primary flow line 2610 including a fluid analysis module 26104 and a fluid pumping module 2620. The fluid pumping module 2620 is in fluid communication with the probe 52 and includes a pump 2622 and a bypass flow line 2624 with bypass valve 2625 that are coupled in parallel with one another as depicted. The SPR sensor 2640 is in fluid communication with primary flow line 2610 and may be configured to receive a formation fluid sample. The downhole tool 51 can further include an isolation valve 2612 that is part of the primary flow line 2610 as well as a discharge valve 2614 and a fluid outlet line 2670 that are fluidly coupled to the primary flow line 2610 as shown. The discharge valve 2614 and the fluid outlet line 2670 can be configured for discharging unwanted formation fluid into the annulus or into the subterranean formation. The downhole tool 51 may further include one or more sample bottles (not shown on FIG. 26) that are fluidly coupled to the primary flow line 2610 by associated valves and have various functionality, such as, for example, zero dead volume (flashing line), self-sealing functionality, and/or being nitrogen-charged as is well known.

The probe assembly 52 may be engaged with the borehole wall 42 as depicted so as to establish fluid communication between the subterranean formation and the primary flow line 2610 (those of ordinary skill will readily appreciate that the probe assembly may penetrate a mud cake layer on the borehole wall so as to obtain fluid directly from the formation). Examples of probes suitable for use in the in the disclosed embodiments include the Single-Probe Module or Dual-Probe Module included in the Schlumberger MDT® or described in U.S. Pat. Nos. 4,860,581 and 6,058,773, which are fully incorporated by reference herein. While not depicted it will be understood that the probe assembly may include or more probes coupled to a frame that may be extended and retracted relative to a tool body. In the depicted embodiment, probe assembly 52 is an inlet probe that provides a flow channel from the subterranean formation to the primary flow line 2610. The downhole tool 51 may further include one or more outlet probes (e.g., at the downstream end of the fluid outlet line 2670) so as to provide a channel through which fluid may flow from the primary flow line 2610 out of the tool 51 and back into the formation. In such an embodiment, fluid may be circulated from the formation into the primary flow line 2610 and back into the formation.

Fluid analysis module 2604 may include substantially any suitable fluid analysis sensors and/or instrumentation, for example, including chemical sensors, optical fluid analyzers, optical spectrometers, nuclear magnetic resonance devices, a conductivity sensor, a temperature sensor, a pressure sensor. More generally, fluid analysis module 104 may include substantially any suitable device that yields information relating to the composition of the formation fluid such as the thermodynamic properties of the fluid, conductivity, density, viscosity, surface tension, pressure, temperature, and phase composition (e.g., liquid versus gas composition or the gas content) of the fluid. While not depicted, it will be understood that fluid analysis sensors may alternatively and/or additionally be deployed on the downstream side of the fluid pumping module, for example, to sense fluid property changes that may be induced via pumping.

Fluid pumping module 2620 may include substantially any suitable pump 2622. For example, the pump 2622 may include a reciprocating piston pump, a retractable piston pump, or a hydraulic powered pump.

The SPR sensor 2640 is fluidly coupled to the primary flow line 1610 by an intake valve 2638 and an exhaust valve 2639. The SPR sensor 2640 can be embodied by any one of the SPR sensors described herein and configured to measure at least one property relating to phase change of formation fluid sample obtained via the probe 52 and the primary flow line 2610.

Figure 27:
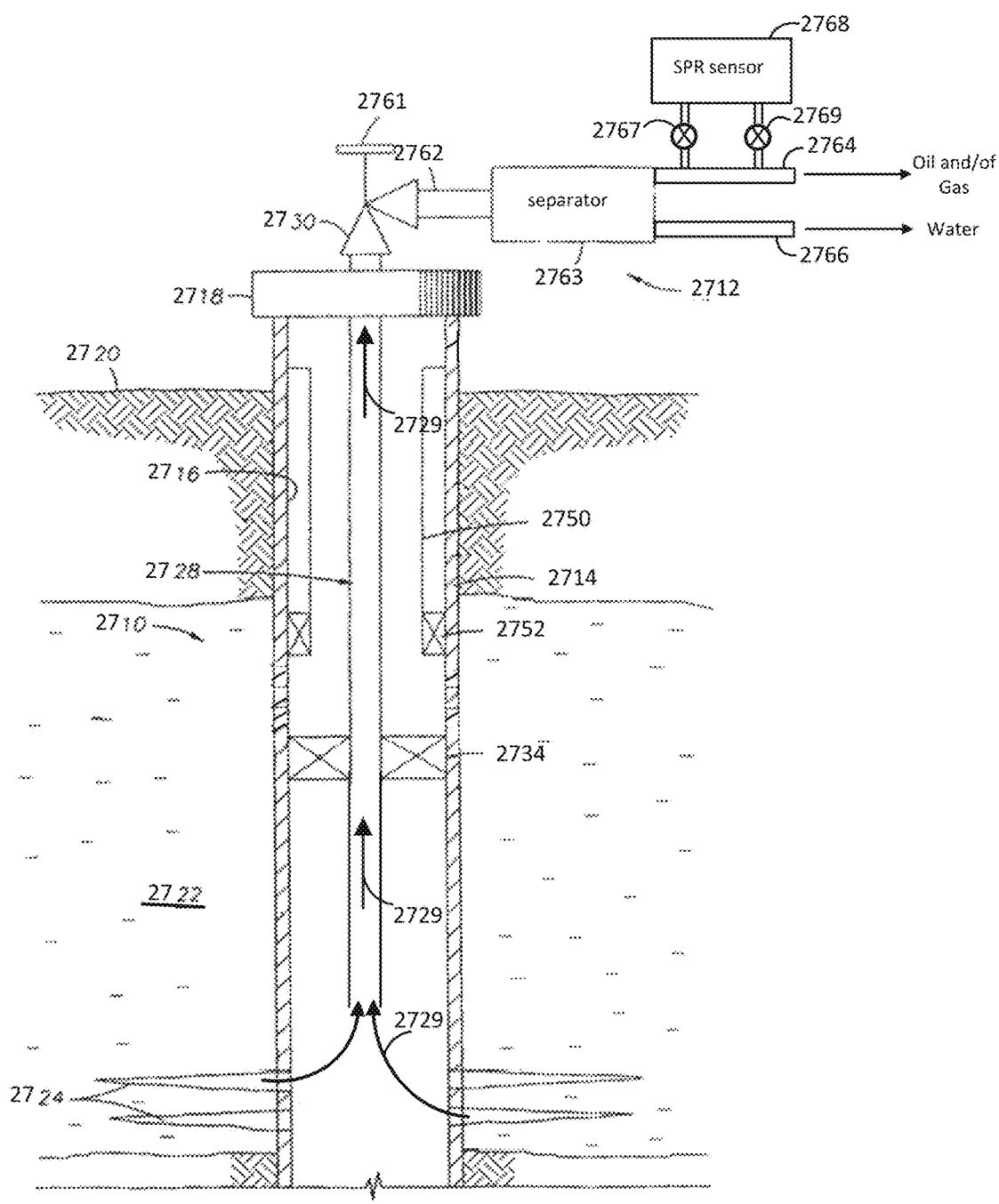
FIG. 27 is a schematic diagram showing one example of a production well in which disclosed SPR sensor embodiments may be utilized.

Referring to FIG. 27, an exemplary hydrocarbon production well 2710 is shown, which includes a wellbore casing 2714, which typically includes a number of concentric casing strings (not shown). The casing 2714 defines an annulus 2716 that extends downward from a wellbore opening or entrance 2718 at the surface 2720. It is noted that the surface 2720 may be either the surface of the earth, or, in the case of a subsea well, the seabed. The casing 2714 extends through a hydrocarbon production zone 2722 from which it is desired to acquire production fluid. The casing 2714 has perforations 2724 disposed therethrough so that production fluid may enter the annulus 2716 from the production zone 2722.

Production tubing 2728 is disposed downward within the annulus 2716 supported from a wellhead 2730 at the surface 2720. A production tubing packer 2734 is set above the perforations 2724 to establish a fluid seal between the production tubing 2728 and the casing 2714. The production tubing 2728 includes at least one fluid inlet below the packer 2734 which permits fluid communication from the annulus 2716 into the interior of the production tubing 2728 to allow production fluid to flow to the wellhead 2730 (indicates as arrows 2729) due to the formation pressure. In some embodiments, artificial lift (such sucker-rod (beam) pumping, electrical submersible pumping (ESP), gas lift and intermittent gas lift, reciprocating and jet hydraulic pumping systems, plunger lift, and progressive cavity pumps (PCP)), can be used to generate or assist in flowing the production fluid through the interior of the production tubing 2728 to the wellhead 2730.

The upper portion of the production tubing 1728 may optionally be surrounded by liner or sleeve 2750 which extends from the well opening 2718 downward within the annulus 2716. A packer 2752 can be set at the lower end of the sleeve 2750 to establish a fluid seal between the sleeve 2750 and the casing 2714. The sleeve 2750 can provide additional isolation between the annulus 2716 and any fresh water aquifers.

The wellhead 2730 can include an adjustable choke 2761 of a type known in the art which is used to control the flow of production fluids through the wellhead 2730. A lateral fluid flowline 2762 extends from the wellhead 2730 to the separator assembly 2763.

The separator assembly 2763 separates the gas/oil and water components of the production fluids supplied thereto, which are output by corresponding flowlines 2764, 2766 as shown. The flowlines 2764 and 2766 carry the respective gas/oil and water components of the production fluids to other surface-located facilities (not shown). Such surface-located facilities can include fluid collection systems (such as tanks), fluid processing devices and/or pipelines.

An SPR sensor 2768 is fluidly coupled to the flow line 2764 by an intake valve 2767 and an exhaust valve 2769. The mercury detector 2764 can be configured to receive a sample of the gas/oil components of the production fluids that is output by the separator 2763 and carried by the flowline 2664. The SPR sensor 2640 can be embodied by any one of the SPR sensors described herein and configured to measure at least one property relating to phase change of production fluid sample obtained via the flowline 2664.

Computer Systems

Note that control logic of the SPR sensors and systems as described above can be implemented as computer program executed by a computer processing platform (e.g., the computer processing system 250 of FIGS. 2 and 21). The computer program may be embodied in various forms, including a source code form or a computer executable form. Source code may include a series of computer program instructions in a variety of programming languages (e.g., an object code, an assembly language, or a high-level language such as C, C++, or JAVA). Such computer instructions can be stored in a non-transitory computer readable medium (e.g., memory) and executed by the computer processing platform. The computer instructions may be distributed in any form as a removable storage medium with accompanying printed or electronic documentation (e.g., shrink wrapped software), preloaded with a computer system (e.g., on system ROM or fixed disk), or distributed from a server over a communication system (e.g., the Internet or World Wide Web).

The computer processing platform may include a CPU, other integrated circuitry (e.g., Application Specific Integrated Circuits (ASIC)), programmable logic devices (e.g., a Field Programmable Gate Arrays (FPGA) and/or discrete electronic components coupled to a printed circuit board. Any of the methods and processes described above can be implemented using such logic devices.

Figure 28:
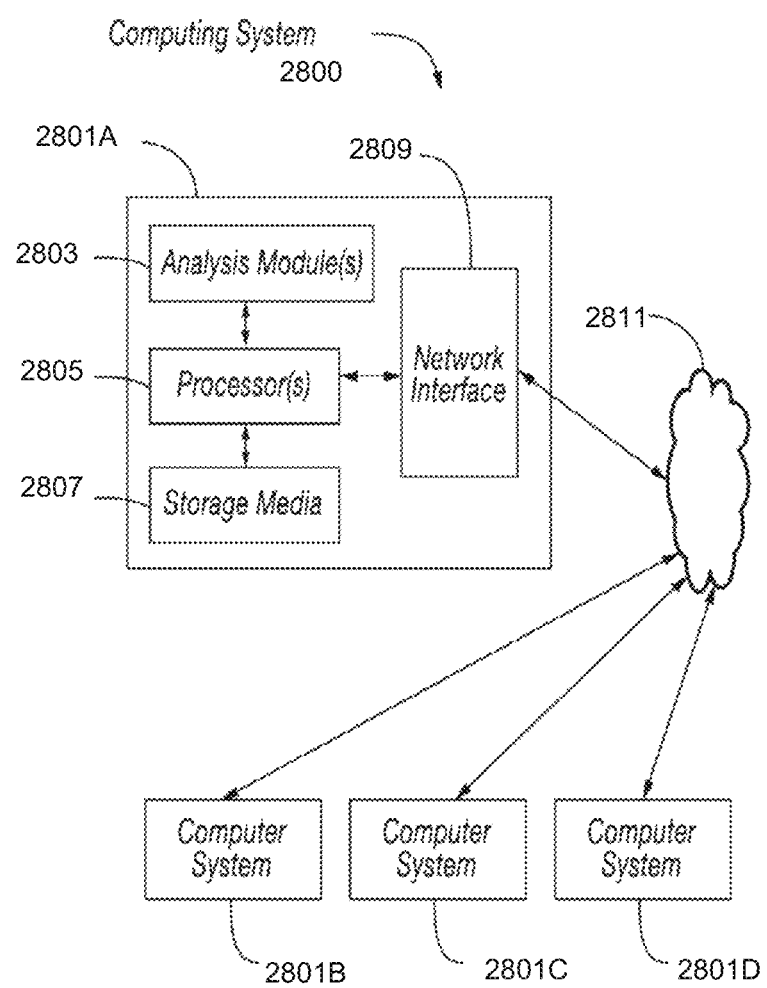
FIG. 28 is a schematic block diagram of a computer processing platform that can be used as part of the disclosed SPR sensor embodiments.

FIG. 28 shows an example computing system 2800 that can be used to implement the computer processing platforms of the SPR sensors as described herein (e.g., the computer processing system 250 of FIGS. 2 and 21). The computing system 2800 can be an individual computer system 2801A or an arrangement of distributed computer systems. The computer system 2801A includes one or more analysis modules 2803 (a program of computer-executable instructions and associated data) that can be configured to perform various tasks according to some embodiments, such as the tasks described herein. To perform these various tasks, an analysis module 2803 executes on one or more processors 2805, which is (or are) connected to one or more storage media 2807. The processor(s) 2805 can be connected to a network interface 2809 to allow the computer system 2801A to communicate over a data network 2811 with one or more additional computer systems and/or computing systems, such as 2801B, 2801C, and/or 2801D. Note that computer systems 2801B, 2801C and/or 2801D may or may not share the same architecture as computer system 2801A, and may be located in different physical locations.

The processor 2805 can include at least a microprocessor, microcontroller, processor module or subsystem, programmable integrated circuit, programmable gate array, digital signal processor (DSP), or another control or computing device.

The storage media 2807 can be implemented as one or more non-transitory computer-readable or machine-readable storage media. Note that while in the embodiment of FIG. 28, the storage media 2807 is depicted as within computer system 2801A, in some embodiments, storage media 2807 may be distributed within and/or across multiple internal and/or external enclosures of computing system 2801A and/or additional computing systems. Storage media 2807 may include one or more different forms of memory including semiconductor memory devices such as dynamic or static random access memories (DRAMs or SRAMs), erasable and programmable read-only memories (EPROMs), electrically erasable and programmable read-only memories (EEPROMs) and flash memories; magnetic disks such as fixed, floppy and removable disks; other magnetic media including tape; optical media such as compact disks (CDs) or digital video disks (DVDs); or other types of storage devices. Note that the computer-executable instructions and associated data of the analysis module(s) 2803 can be provided on one computer-readable or machine-readable storage medium of the storage media 2807, or alternatively, can be provided on multiple computer-readable or machine-readable storage media distributed in a large system having possibly plural nodes. Such computer-readable or machine-readable storage medium or media is (are) considered to be part of an article (or article of manufacture). An article or article of manufacture can refer to any manufactured single component or multiple components. The storage medium or media can be located either in the machine running the machine-readable instructions, or located at a remote site from which machine-readable instructions can be downloaded over a network for execution.

The computing system 2800 can also include one or more display devices that are configured to display information produced by the various tasks according to some embodiments, such as the tasks described herein. For example, the display device can display plots or other visual representations of the intensity data or spectra produced by the various SPR sensor embodiments for human evaluation of the data as desired.

It should be appreciated that computing system 2800 is only one example of a computing system, and that computing system 2800 may have more or fewer components than shown, may combine additional components not depicted in the embodiment of FIG. 28, and/or computing system 2800 may have a different configuration or arrangement of the components depicted in FIG. 28. The various components shown in FIG. 28 may be implemented in hardware, software, or a combination of both hardware and software, including one or more signal processing and/or application specific integrated circuits.

Modifications

Although only a few examples have been described in detail above, those skilled in the art will readily appreciate that many modifications are possible in the examples without materially departing from this subject disclosure.

In alternate embodiments, the light guiding function of the prism of the SPR sensors as described herein can be replaced with one or more optical elements that direct light to the metallic film and direct light reflected at the interface of the metallic film to the optoelectronic devices of the SPR sensors as described herein, e.g., the photodetector and signal processing circuitry of the SPR sensors of FIGS. 1 and 19 or the spectrometer of the SPR sensors of FIGS. 20 and 23A. For example, an optical fiber can be used to direct light (either monochromatic light or polychromatic light) to the metallic film and to direct light reflected at the interface of the metallic film to the optoelectronic devices of the SPR sensors as described herein. In this configuration, an end or intermediate portion of the optical fiber can be coated with a metallic film or thin film metallic stack as described herein. The coated portion of the optical fiber can be positioned adjacent to or within the sample chamber of the sample cell (or flow-thru cell) of the SPR sensor as described herein in order to define the SPR sensing zone that is used to detect and evaluate phase transition of a hydrocarbon-based analyte within the SPR sensing zone as described herein.

In another example, an SPR sensor can perform measurements utilizing monochromatic light at multiple wavelengths. In this case, each wavelength probes a different distance into the SPR sensing region, which can allow for determination of the thickness of solid precipitation Also, the methods and systems described herein are not limited to analyzing a set of particular fluids. Various embodiments of methods and systems described herein can be used to analyze hydrocarbons (e.g., dark oils, heavy oils, volatile oils, and black oils).

Furthermore, various embodiments of the present disclosure are not limited to oil and gas field applications.

Also, the fluid handling elements (such as reservoirs, tanks, pumps, valves and flow lines) of the SPR sensors as described herein can be computer controlled or manually controlled to provide for pressure control of the fluids flowing through the SPR sensor. Furthermore, the temperature control elements of the SPR sensors as described herein can be computer controlled or manually controlled to provide for temperature control of the fluids flowing through the SPR sensor.

Furthermore, the intensity of the light that is incident on the metallic film (or stack), which is referred to as "incident intensity") can be detected and measured. In this case, the intensity of the light that is reflected from the metallic film (or stack) as detected and measured by the photodetector and signal processing circuitry can be subtracted from the incident intensity to provide data that characterizes the absorbance of the light at the metallic film interface. This absorbance data, which can be equated to intensity data for the purposes of this patent application, can be processed as intensity data as described herein in order to detect a phase transition or related property of a hydrocarbon-based analyte. Similarly, the spectrum of the light that is incident on the metallic film (or stack), which is referred to as "incident spectrum") can be detected and measured. In this case, the spectrum of the light that is reflected from the metallic film (or stack) as detected and measured by the spectrometer can be subtracted from the incident spectrum to provide a spectrum that characterizes the absorbance of the light at the metallic film interface. This absorbance spectrum, which can be equated to the SPR spectrum for the purposes of this patent application, can be processed as part of the SPR spectra as described herein in order to detect a phase transition or related property of a hydrocarbon-based analyte.

To the extent used in this description and in the claims, a recitation in the general form of "at least one of [a] and [b]" should be construed as disjunctive. For example, a recitation of "at least one of [a], [b], and [c]" would include [a] alone, [b] alone, [c] alone, or any combination of [a], [b], and [c].

Although several example embodiments have been described in detail above, those skilled in the art will readily appreciate that many modifications are possible in the example embodiments without materially departing from the scope of this disclosure. Moreover, the features described herein may be provided in any combination.

Accordingly, all such modifications are intended to be included within the scope of this disclosure as defined in the following claims. In the claims, means-plus-function clauses are intended to cover the structures described herein as performing the recited function and not only structural equivalents, but also equivalent structures. Thus, although a nail and a screw may not be structural equivalents in that a nail employs a cylindrical surface to secure wooden parts together, whereas a screw employs a helical surface, in the environment of fastening wooden parts, a nail and a screw may be equivalent structures. It is the express intention of the applicant not to invoke 35 U.S.C. § 112, paragraph 6 for any limitations of any of the claims herein, except for those in which the claim expressly uses the words 'means for' together with an associated function.

What is claimed is:

1. An optical sensor comprising:
a sample chamber configured to hold a hydrocarbon-based analyte;
a temperature control element configured to regulate temperature of the hydrocarbon-based analyte in the sample chamber;
a pressure control element configured to regulate pressure of the of the hydrocarbon-based analyte in the sample chamber;
a metallic film disposed adjacent the sample chamber;
a light source configured to generate light;
an optical element configured to direct light produced by the light source to the metallic film under conditions of surface plasmon resonance and to direct light reflected at the interface of the metallic film for output from the optical element, such that the light reflected at the interface of the metallic film is sensitive to surface plasmon resonance at the interface of the metallic film;
an optoelectronic device configured to (a) receive light reflected at the interface of the metallic film as directed by the optical element and (b) generate a corresponding electrical signal; and
a computer processing system configured to generate and store data based on the electrical signal generated by the optoelectronic device for a number of test measurements at variable conditions of the hydrocarbon-based analyte in the sample chamber as controlled by the temperature control element and the pressure control element, and wherein the computer processing system is configured to process the data to determine at least one property related to phase transition of the hydrocarbon-based analyte.

2. An optical sensor according to claim 1, wherein:
the at least one property related to phase transition of the hydrocarbon-based analyte is induced by at least one of: change in temperature of the hydrocarbon-based analyte, change in pressure of the hydrocarbon-based analyte, and change in composition of the hydrocarbon-based analyte; and/or
the at least one property related to phase transition of the hydrocarbon-based analyte specifies temperature and/or pressure conditions for a phase transition of the hydrocarbon-based analyte.

3. An optical sensor according to claim 1, wherein the at least one property related to phase transition of the hydrocarbon-based analyte specifies temperature and/or pressure conditions for a phase transition of the hydrocarbon-based analyte.

4. An optical sensor according to claim 1, wherein:
the temperature control element includes at least one of (a) a heat exchanger, (b) a thermo-electric Peltier device, and (c) a heat sink.

5. An optical sensor according to claim 1, wherein:
the optical element comprises a prism that directs light produced by the light source to the metallic film and that directs light reflected at the interface of the metallic film for output from the prism.

6. An optical sensor according to claim 5, wherein:
the light source comprises a monochromatic light source that produces monochromatic light;
the sample chamber, the prism and the at least one temperature control element are part of a thermally-controlled assembly that is configured for controlled rotational movement of the thermally-controlled assembly relative to the monochromatic light source in order to vary angle of incidence of monochromatic light on the interface of the metallic film; and
the optoelectronic device comprises a photodetector that is configured for controlled linear movement along a trajectory that maintains alignment of the photodetector with center of a reflected light beam that is output from the prism during controlled rotational movement of the thermally-controlled assembly relative to the monochromatic light source.

7. An optical sensor according to claim 6, further comprising:
a mechanical chopper disposed in an optical path between the monochromatic light source and the prism, wherein the mechanical chopper is configured to modulate the monochromatic light produced by the monochromatic light source at a predetermined frequency for supply to the prism; and
a lock-in amplifier that processes an electrical signal output of the photodetector, wherein operation of the lock-in amplifier is coordinated with the predetermined frequency of light modulation performed by the mechanical chopper.

8. An optical sensor according to claim 6, wherein:
the computer processing system is configured to generate and store intensity data based on the electrical signal generated by the photodetector as a function of angular position of the thermally-controlled assembly relative to the monochromatic light source during controlled rotational movement of the thermally-controlled assembly relative to the monochromatic light source for the number of test measurements at variable conditions of the hydrocarbon-based analyte in the sample chamber as controlled by the at least one temperature control element and the at least one pressure control element, wherein the intensity data characterizes intensity of light reflected at the interface of the metallic film during controlled rotational movement of the thermally-controlled assembly relative to the monochromatic light source, and wherein the computer processing system processes the intensity data as a function of angular position of the thermally-controlled assembly relative to the monochromatic light source to determine the at least one property related to phase transition of the hydrocarbon-based analyte.

9. An optical sensor according to claim 8, wherein:
the intensity data corresponding to different angular positions of the thermally-controlled assembly relative to the monochromatic light source is evaluated to determine the at least one property related to phase transition of the hydrocarbon-based analyte.

10. An optical sensor according to claim 9, wherein:
the at least one property related to phase transition of the hydrocarbon-based analyte is determined based on at least one of the following: i) a temperature condition and/or pressure condition corresponding to a local minima or dip in the intensity data as a function of the angular position of the thermally-controlled assembly relative to the monochromatic light source; ii) a temperature condition and/or pressure condition corresponding to an abrupt change to slope or shape of a local minima or dip in the intensity data as a function of the angular position of the thermally-controlled assembly relative to the monochromatic light source; iii) a temperature condition and/or pressure condition corresponding to an abrupt change in the minimum of the intensity data over the angular positions of the thermally-controlled assembly as a function of temperature or pressure; iv) a temperature condition and/or pressure condition corresponding to an abrupt change in the intensity data at a plurality of angular positions of the thermally-controlled assembly as a function of temperature or pressure; v) a temperature condition and/or pressure condition corresponding to an abrupt change in the angle of minimum intensity data over the angular positions of the thermally-controlled assembly relative to the monochromatic light as a function of temperature or pressure; and vi) a temperature condition and/or pressure condition corresponding to a signal metric derived from the intensity data over the angular positions of the thermally-controlled assembly relative to the monochromatic light as a function of temperature or pressure.

11. An optical sensor according to claim 5, wherein:
the light source comprises a polychromatic light source that produces polychromatic light;
the sample chamber, the prism and the at least one thermal control element are part of a thermally-controlled assembly; and
the optoelectronic device comprises a spectrometer that is configured to receive polychromatic light reflected from the metallic film.

12. An optical sensor according to claim 11, wherein:
the computer processing system is configured to generate and store spectral data based on the electrical signals generated by the spectrometer for the number of test measurements at variable conditions of the hydrocarbon-based analyte in the sample chamber as controlled by the at least one temperature control element and the at least one pressure control element, and wherein the computer processing system is configured to process the spectral data to determine the at least one property related to phase transition of the hydrocarbon-based analyte.

13. An optical sensor according to claim 12, wherein:
The computer processing system is configured to evaluate spectral data to determine the at least one property related to phase transition of the hydrocarbon-based analyte.

14. An optical sensor according to claim 13, wherein:
The computer processing system is configured to determine the at least one property related to phase transition of the hydrocarbon-based analyte based on temperature and/or pressure conditions that produce a shift in a local minima or dip in the spectral data or temperature and/or pressure conditions that produce a signal metric in the spectral data.

15. An optical sensor according to claim 1, wherein at least one of (a) the sample chamber has a fixed volume and (b) the sample chamber is part of a flow-thru cell.

16. An optical sensor according to claim 1, wherein:
the metallic film is formed (a) as a coating on the optical element or (b) as a coating on a substrate that is disposed adjacent the optical element.

17. An optical sensor according to claim 1, wherein:
a layer of protective material covers the metallic film such that the hydrocarbon-based analyte does not directly contact the metallic film.

18. An optical sensor according to claim 1, further comprising:
an electrical circuit that is electrically coupled to the metallic film for controlled resistive heating of the metallic film.

19. An optical sensor according to claim 18, wherein:
the electric circuit is configured to provide pulsed-mode operation including on cycles where the metallic film is heating by resistive heating and off cycles where the metallic film is not heated by resistive heating.

20. An optical sensor according to claim 1, wherein:
the at least one property related to phase transition of the hydrocarbon-based analyte is derived from test measurements with i) pressure or pressure differential of the hydrocarbon-based analyte in the sample chamber at a controlled pressure and ii) temperature of the hydrocarbon-based analyte in the sample chamber controlled over a range of set point temperatures.

21. An optical sensor according to claim 1, wherein:
the at least one property related to phase transition of the hydrocarbon-based analyte is a temperature condition and/or pressure condition where components that are dissolved in the hydrocarbon-based analyte precipitate and form liquids or solids; and/or
the at least one property related to phase transition of the hydrocarbon-based analyte is a Wax Appearance Temperature (WAT) where wax components that are dissolved in the hydrocarbon-based analyte first precipitate and form solid material; and/or
the at least one property related to phase transition of the hydrocarbon-based analyte is a temperature condition and/or pressure condition where components of the hydrocarbon-based analyte transition from a gas phase to a liquid phase; and/or
the at least one property related to phase transition of the hydrocarbon-based analyte is a temperature condition and/or pressure condition where components of the hydrocarbon-based analyte transition from a liquid phase to a gas phase; and/or
the at least one property related to phase transition of the hydrocarbon-based analyte is bubble point temperature and/or pressure conditions where vapor forms from the hydrocarbon-based analyte or where vapor dissolve into the hydrocarbon-based analyte as induced by changes in temperature, pressure and/or composition of the hydrocarbon-based analyte; and/or the at least one property related to phase transition of the hydrocarbon-based analyte is a temperature condition and/or pressure condition where hydrates form from the hydrocarbon-based analyte as induced by changes in temperature, pressure and/or composition of the hydrocarbon-based analyte; and/or
the at least one property related to phase transition of the hydrocarbon-based analyte is a temperature condition and/or pressure condition where scale or other inorganic material precipitate from the hydrocarbon-based analyte as induced by changes in temperature, pressure and/or composition of the hydrocarbon-based analyte.

22. An optical sensor according to claim 1, wherein:
the at least one property related to phase transition of the hydrocarbon-based analyte is a temperature condition and/or pressure condition where asphaltenes in the hydrocarbon-based analyte precipitate as liquid or solid, and/or deposit as a liquid or solid film as induced by changes in temperature, pressure and/or composition of the hydrocarbon-based analyte.

23. A downhole tool that can be conveyed in a wellbore that traverses a subterranean formation and configured to sample formation fluid obtained from the subterranean formation, the downhole tool comprising:
the optical sensor of claim 1 for determining at least one property related to phase transition of the formation fluid.

24. A wellsite that produces fluid obtained from a subterranean formation, wherein the wellsite includes the optical sensor of claim 1 for determining at least one property related to phase transition of the produced fluid.

25. A method of optical sensing comprising:
loading a sample chamber with a hydrocarbon-based analyte and a metallic film disposed adjacent the sample chamber;
with the hydrocarbon-based analyte in the sample chamber, directing light produced by a light source to the metallic film under conditions of surface plasmon resonance and directing light reflected at the interface of the metallic film to an optoelectronic device configured to (a) receive the light reflected at the interface of the metallic film and (b) generate a corresponding electrical signal, wherein the light reflected at the interface of the metallic film is sensitive to surface plasmon resonance at the interface of the metallic film;
using a computer processing system to generate and process data based on the electrical signal to detect a phase transition or related property with respect to the hydrocarbon-based analyte; and
wherein the computer processing system generates data based on the electrical signal generated by the optoelectronic device for a number of test measurements at variable conditions of the hydrocarbon-based analyte in the sample chamber as controlled by at least one temperature control element and at least one pressure control element.

26. A method according to claim 25, wherein:
the optoelectronic device comprises a photodetector;
the computer processing system generates and stores intensity data derived from the output of the photodetector; and
the computer processing system processes the intensity data to detect a phase transition or related property with respect to the hydrocarbon-based analyte.

27. A method according to claim 25, wherein:
the optoelectronic device comprises a spectrometer;
the computer processing system acquires and stores spectral data generated by the spectrometer; and
the computer processing system processes the spectral data to detect a phase transition or related property with respect to the hydrocarbon-based analyte.

* * * * *